US009745288B2

(12) United States Patent
Meroueh

(10) Patent No.: US 9,745,288 B2
(45) Date of Patent: Aug. 29, 2017

(54) COMPOUNDS AND METHODS FOR TREATING CANCER BY INHIBITING THE UROKINASE RECEPTOR

(75) Inventor: Samy O. Meroueh, Carmel, IN (US)

(73) Assignee: Indiana University Research and Technology Corporation, Indianapolis, IN (US)

(*) Notice: Subject to any disclaimer, the term of this patent is extended or adjusted under 35 U.S.C. 154(b) by 232 days.

(21) Appl. No.: 14/238,504

(22) PCT Filed: Aug. 16, 2012

(86) PCT No.: PCT/US2012/051211

§ 371 (c)(1),
(2), (4) Date: May 20, 2014

(87) PCT Pub. No.: WO2013/025939

PCT Pub. Date: Feb. 21, 2013

(65) Prior Publication Data

US 2015/0051247 A1 Feb. 19, 2015

Related U.S. Application Data

(60) Provisional application No. 61/524,051, filed on Aug. 16, 2011.

(51) Int. Cl.

| | |
|---|---|
| ***A61K 31/36*** | (2006.01) |
| ***C07D 405/04*** | (2006.01) |
| ***A61K 31/402*** | (2006.01) |
| ***A61K 31/445*** | (2006.01) |
| ***A61K 31/453*** | (2006.01) |
| ***A61K 31/454*** | (2006.01) |
| ***C07D 207/277*** | (2006.01) |
| ***C07D 211/94*** | (2006.01) |
| ***C07D 317/50*** | (2006.01) |
| ***C07D 401/04*** | (2006.01) |

(52) U.S. Cl.

CPC ............ *C07D 405/04* (2013.01); *A61K 31/36* (2013.01); *A61K 31/402* (2013.01); *A61K 31/445* (2013.01); *A61K 31/453* (2013.01); *A61K 31/454* (2013.01); *C07D 207/277* (2013.01); *C07D 211/94* (2013.01); *C07D 317/50* (2013.01); *C07D 401/04* (2013.01)

(58) Field of Classification Search

CPC .... A61K 31/36; A61K 31/402; A61K 31/445; A61K 31/453; A61K 31/454

See application file for complete search history.

(56) References Cited

U.S. PATENT DOCUMENTS

| | | | |
|---|---|---|---|
| 3,773,919 | A | 11/1973 | Boswell et al. |
| 4,485,045 | A | 11/1984 | Regen |
| 4,544,545 | A | 10/1985 | Ryan et al. |
| 5,521,184 | A | 5/1996 | Zimmermann |
| 5,712,291 | A | 1/1998 | D'Amato |
| 5,728,813 | A | 3/1998 | Lyman et al. |
| 5,747,498 | A | 5/1998 | Schnur et al. |
| 5,770,599 | A | 6/1998 | Gibson |
| 5,792,783 | A | 8/1998 | Tang et al. |
| 5,892,112 | A | 4/1999 | Levy et al. |
| 5,969,110 | A | 10/1999 | Beckmann et al. |
| 5,981,245 | A | 11/1999 | Fox et al. |
| 5,990,141 | A | 11/1999 | Hirth et al. |
| 6,057,124 | A | 5/2000 | Bartley et al. |
| 6,232,447 | B1 | 5/2001 | Cerretti |
| 6,235,764 | B1 | 5/2001 | Larson et al. |
| 6,258,812 | B1 | 7/2001 | Bold et al. |
| 6,413,932 | B1 | 7/2002 | Cerretti et al. |
| 6,515,004 | B1 | 2/2003 | Misra et al. |
| 6,596,852 | B2 | 7/2003 | Cerretti et al. |
| 6,630,500 | B2 | 10/2003 | Gingrich et al. |
| 6,713,485 | B2 | 3/2004 | Carter et al. |
| 6,727,225 | B2 | 4/2004 | Wiley |
| 2002/0042368 | A1 | 4/2002 | Fanslow, III et al. |
| 2003/0105091 | A1 | 6/2003 | Riedl et al. |
| 2003/0162712 | A1 | 8/2003 | Cerretti et al. |

(Continued)

FOREIGN PATENT DOCUMENTS

| | | | |
|---|---|---|---|
| EP | 0 058 481 | A1 | 8/1982 |
| EP | 0 102 324 | A2 | 3/1984 |
| EP | 0 133 988 | A2 | 3/1985 |

(Continued)

OTHER PUBLICATIONS

Wang et al 'Virtual Screening Targeting the Urokinase Receptor, Biochemical and Cell-Based Studies, Synthesis, Pharmacokinetic Characterization, and Effect on Breast Tumor Metastasis' Journal of Medicinal Chemistry, vol. 54, p. 7193-7205, 2011.*

Chen et al 'Challenges for drug discovery—a case study of urokinase receptor inhibition' Comb. Chem. High Throughput Screen. 12(10), p. 961-967, 2009.*

Sporn, M. B. The war on cancer. Lancet 1996, 347, 1377-81.

Wei, Y.; Lukashev, M.; Simon, D. I.; Bodary, S. C.; Rosenberg, S.; Doyle, M. V.; Chapman, H. A. Regulation of integrin function by the urokinase receptor.Science 1996, 273, 1551-1555.

Kiyan, J.; Kiyan, R.; Haller, H.; Dumler, I. Urokinase-induced signaling in human vascular smooth muscle cells is mediated by PDGFR-beta. Embo J 2005, 24, 1787-97.

Liu, D.; Aguirre Ghiso, J.; Estrada, Y.; Ossowski, L. EGFR is a transducer of the urokinase receptor initiated signal that is required for in vivo growth of a human carcinoma Cancer Cell 2002, 1, 445-57.

Shapiro, R. L.; Duquette, J. G.; Nunes, I.; Roses, D. F.; Harris, M. N.; Wilson,E. L.; Rifkin, D. B. Urokinase-type plasminogen activator-deficient mice are predisposed to staphylococcal botryomycosis, pleuritis, and effacement of lymphoid follicles. Am J Pathol 1997, 150, 359-69.

(Continued)

*Primary Examiner* — Craig Ricci
*Assistant Examiner* — Christopher R Stone
(74) *Attorney, Agent, or Firm* — Miles & Stockbridge P.C.; Ajay A. Jagtiani

(57) ABSTRACT

Compounds and methods for treating or preventing cancer associated with binding to the urokinase receptor are provided. Biological processes affected by the compounds include cell migration, cell growth, cell adhesion, angiogenesis, cancer cell invasion, apoptosis, tumor formation, tumor progression, metastasis, degradation of the extracellular matrix, pericellular proteolysis, activation of plasminogen, changes in the levels of an extracellular protease, and changes in the levels of a VEGF receptor.

25 Claims, 23 Drawing Sheets

(56) References Cited

U.S. PATENT DOCUMENTS

2010/0075949 A1* 3/2010 Burdack ............ C07D 207/277
514/210.18

FOREIGN PATENT DOCUMENTS

| | | | |
|---|---|---|---|
| EP | 0 407 122 | A1 | 1/1991 |
| EP | 0 770 622 | A2 | 5/1997 |
| JP | 2002-233610 | A | 8/2002 |
| WO | 99/45009 | A1 | 9/1999 |
| WO | 99/61422 | A1 | 12/1999 |
| WO | 00/02871 | A1 | 1/2000 |
| WO | 00/12089 | A1 | 3/2000 |
| WO | 00/59509 | A1 | 10/2000 |
| WO | 01/32651 | A1 | 5/2001 |
| WO | 01/37820 | A2 | 5/2001 |
| WO | 02/055501 | A2 | 7/2002 |
| WO | 02/059110 | A1 | 8/2002 |
| WO | 02/066470 | A1 | 8/2002 |
| WO | 02/068406 | A2 | 9/2002 |
| WO | 2004/005279 | A2 | 1/2004 |
| WO | 2004/007458 | A1 | 1/2004 |
| WO | 2004/007481 | A2 | 1/2004 |
| WO | 2004/009784 | A2 | 1/2004 |

OTHER PUBLICATIONS

Kirchheimer, J. C.; Wojta, J.; Christ, G.; Binder, B. R. Proliferation of a human epidermal tumor cell line stimulated by urokinase. Faseb J 1987, 1, 125-8.

Kirchheimer, J. C.; Wojta, J.; Christ, G.; Binder, B. R. Functional inhibition of endogenously produced urokinase decreases cell proliferation in a human melanoma cell line. Proc Natl Acad Sci USA 1989, 86, 5424-8.

Andreasen, P. A.; Kjoller, L.; Christensen, L.; Duffy, M. J. The urokinase-type plasminogen activator system in cancer metastasis: A review. International Journal of Cancer 1997, 72, 1-22.

Mignatti, P.; Rifkin, D. B. Plasminogen activators and matrix metalloproteinases in angiogenesis. Enzyme Protein 1996, 49, 117-37.

Rabbani, S. A.; Mazar, A. P. The role of the plasminogen activation system in angiogenesis and metastasis. Surg Oncol Clin N Am 2001, 10, 393-415.

Kim, J.; Yu, W.; Kovalski, K.; Ossowski, L. Requirement for specific proteases in cancer cell intravasation as revealed by a novel semiquantitative PCR-based assay. Cell 1998, 94, 353-62.

Berge. S. M.; Bighley, L. D.; Monkhouse, D. C. Pharmaceutical Salts. J Pharm Sci 1977, 66, 1-19.

Sidman, K. R.; Steber, W. D.; Schwope, A. D.; Schnaper, G. R. Control release of macromolecules and pharmaceuticals from synthetic polypeptides based on glutamic acid Biopolymers 1983, 22, 547-56.

Langer, R; Brem, H; Tapper, D. Biocompatibility of polymeric delivery systems for macromolecules. J Biomed Mater Res 1981, 15, 267-77.

Langer, R. Controlled release of macromolecules. Chem Tech 1982, 12, 98-105.

Eppstein, D. A.; Marsh, Y. V.; van der Pas, M.; Feigner, P. L.; Schreiber, A. B. Biological activity of liposome-encapsulated murine interferon gamma is mediated by a cell membrane receptor. Proc Natl Acad Sci USA 1985, 82, 3688-92.

Hwang, K. J.; Luk, K. F.; Beaumier, P. L. Hepatic uptake and degradation of unilamellar sphingomyelin/cholesterol liposomes: a kinetic study. Proc Natl Acad Sci USA 1980, 77, 4030-34.

Greene, T. W.; Wuts, P.G. M. Protective Groups in Organic Synthesis, 3rd ed. John Wiley & Sons 1999.

Dorfleutner, A.; Stehlik, C.; Zhang, J.; Gallick, G. E.; Flynn, D. C. AFAP-110 is required for actin stress fiber formation and cell adhesion in MDA-MB-231 breast cancer cells. J Cell Physiol 2007, 213, 740-749.

Chavakis, T.; Kanse, S. M.; Lupu, F.; Hammes, H. P.; Muller-Esterl, W.; Pixley, R. A.; Colman, R. W.; Preissner, K. T. Different mechanisms define the antiadhesive function of high molecular weight kininogen in integrin- and urokinase receptor dependent interactions. Blood 2000, 96, 514-22.

Ingram, D. A.; Mead, L. E.; Tanaka, H.; Meade, V.; Fenoglio, A.; Modell, K.; Pollok, K.; Ferkowicz, M. J.; Gilley, D.; Yoder, M. C. Identification of a novel hierarchy of endothelial progenitor cells using human peripheral and umbilical cord blood. Blood 2004, 104, 2752-60.

Hochreiter, A. E.; Xiao, H.; Goldblatt, E. M.; Gryaznov, S. M.; Miller, K. D.; Badve, S.; Sledge, G. W.; Herbert, B. S. Telomerase template antagonist GRN163L disrupts telomere maintenance, tumor growth, and metastasis of breast cancer. Clin Cancer Res 2006, 12, 3184-92.

Eldridge, M. D.; Murray, C. W.; Auton, T. R.; Paolini, G. V.; Mee, R. P. Empirical scoring functions: I. The development of a fast empirical scoring function to estimate the binding affinity of ligands in receptor complexes. J Comput Aided Mol Des 1997, 11, 425-45.

Jones, G.; Willett, P.; Glen, R. C.; Leach, A. R.; Taylor, R. Development and validation of a genetic algorithm for flexible docking. J Mol Biol 1997, 267, 727-48.

Huey, R.; Morris, G. M.; Olson, A. J.; Goodsell, D. S. A semiempirical free energy force field with charge-based desolvation. Journal of Computational Chemistry 2007, 28, 1145-1152.

Huang, N.; Kalyanaraman, C.; Irwin, J. J.; Jacobson, M. P. Physics-based scoring of protein-ligand complexes: enrichment of known inhibitors in large-scale virtual screening. J Chem Int Model 2006, 46, 243-53.

Huai, Q.; Zhou, A.; Lin, L.; Mazar, A. P.; Parry, G. C.; Callahan, J.; Shaw, D. E.; Furie, B.; Furie, B. C.; Huang, M. Crystal structures of two human vitronectin, urokinase and urokinase receptor complexes. Nat Struct Mol Biol 2008, 15, 422-3.

Chen, H. C. Boyden chamber assay. Methods Mol Biol 2005, 294, 15-22.

Khanna, M.; Chelladurai, B.; Gavini, A.; Li, L.; Shao, M.; Courtney, D.; Turchi, J. J.; Matei, D.; Meroueh, S. Targeting ovarian tumor cell adhesion mediated by tissue transglutaminase. Mol Cancer Ther 2011, 10, 626-36.

Simon, D. I.; Wei, Y.; Zhang, L.; Rao, N. K.; Xu, H.; Chen, Z. P.; Liu, Q. M.; Rosenberg, S.; Chapman, H. A. Identification of a urokinase receptor-integrin interaction site—Promiscuous regulator of integrin function. Journal of Biological Chemistry 2000, 275, 10228-10234.

Wei, Y.; Eble, J. A.; Wang, Z. M.; Kreidberg, J. A.; Chapman, H. A. Urokinase receptors promote beta 1 integrin function through interactions with integrin alpha 3 beta 1. Molecular Biology of the Cell 2001, 12, 2975-2986.

Wei, Y.; Tang, C. H.; Kim, Y.; Robillard, L.; Zhang, F.; Kugler, M. C.; Chapman, H. A. Urokinase receptors are required for alpha 5 beta 1 integrin-mediated signaling in tumor cells. J Biol Chem 2007, 282, 3929-39.

Folkman, J. Angiogenesis in Cancer, Vascular, Rheumatoid and Other Disease. Nature Medicine 1995, 1, 27-31.

Brown, S.; Meroueh, S. O.; Fridman, R.; Mobashery, S. Quest for selectivity in inhibition of matrix metalloproteinases. Curr Top Med Chem 2004, 4, 1227-38.

Wang, A. X.; Xie, Q.; Lane, B.; Mollison, K. W.; Hsieh, G. C.; Marsh, K.; Sheets, M. P.; Luly, J. R.; Coghlan, M. J. Synthesis and immunosuppressant activity of pyrazole carboxamides. Bioorg Med Chem Lett 1998, 8, 2787-92.

Bashford, K. E.; Burton, M. B.; Cameron, S.; Cooper, A. L.; Hogg, R. D.; Kane, P. D.; MacManus, D. A.; Matrunola, C. A.; Moody, C. J.; Robertson, A. A. B.; Warne, M. R. The Bohlmann-Rahtz route to functionalised pyridine scaffolds and their use in library synthesis. Tetrahedron Letters 2003, 44, 1627-1629.

Clay, R. J.; Collom, T. A.; Karrick, G. L.; Wemple, J. A Safe, Economical Method for the Preparation of Beta-Oxo Esters. Synthesis-Stuttgart 1993, 290-292.

Piper, D. R.; Duff, S. R.; Eliason, H. C.; Frazee, W. J.; Frey, E. A.; Fuerstenau-Sharp, M.; Jachec, C.; Marks, B. D.; Pollok, B. A.; Shekhani, M. S.; Thompson, D. V.; Whitney, P.; Vogel, K. W.; Hess, S. D. Development of the predictor HERG fluorescence polarization assay using a membrane protein enrichment approach. Assay Drug Dev Technol 2008, 6, 213-23.

(56) References Cited

OTHER PUBLICATIONS

Kim, I.; Boyle, K. M.; Carroll, J. L. Postnatal development of E-4031-sensitive potassium current in rat carotid chemoreceptor cells. J Appl Physiol 2005, 98, 1469-77.
Guengerich, F. P. Common and uncommon cytochrome P450 reactions related to metabolism and chemical toxicity. Chem Res Toxicol 2001, 14, 611-50.
Cohen, L. H.; Remley, M. J.; Raunig, D.; Vaz, A. D. In vitro drug interactions of cytochrome p450: an evaluation of fluorogenic to conventional substrates. Drug Metab Dispos 2003, 31, 1005-15.
Li, L.; Li, J.; Khanna M.; Jo, I.; Baird, J. P.; Meroueh, S. O. Docking to Erlotinib Off-Targets Leads to Inhibitors of Lung Cancer Cell Proliferation with Suitable Pharmacokinetics. ACS Med. Chem. Lett. 2010, 1, 229-233.
Tse, W. C.; Boger, D. L. A fluorescent intercalator displacement assay for establishing DNA binding selectivity and affinity. Curr Protoc Nucleic Acid Chem 2005, Chapter 8, Unit 8 5.
Bateman, K. P.; Castonguay, G.; Xu, L.; Rowland, S.; Nicoll-Griffith, D. A.; Kelly, N.; Chan, C. C. Reduction of animal usage by serial bleeding of mice for pharmacokinetic studies: application of robotic sample preparation and fast liquid chromatography-mass spectrometry. J Chromatogr B Biomed Sci Appl 2001, 754, 245-51.

* cited by examiner

| p.o. (mg/kg) | $C_{max}$ (ng/mL) | $t_{max}$ (hours) |
|---|---|---|
| 100 | 4,414 | 1 |

| $t_{1/2}$ (hours) | $AUC_{[illegible]}$ ( ng*mL$^{-1}$*hr) | Cl/F (L/hr) |
|---|---|---|
| 2.18 | 47,158 | 0.042 |

IC50=3.9 uM

IC50=30.7 uM

IC50=13.34 uM

IC50=9.67uM

IC50=13.11 uM $EC_{50}$ = 13.17

$EC_{50}$ = 24.98

COMPOUNDS AND METHODS FOR TREATING CANCER BY INHIBITING THE UROKINASE RECEPTOR

CROSS-REFERENCE TO RELATED APPLICATIONS

This application is a 35 U.S.C. §371 National Stage Application of International Patent Application No. PCT/US2012/051211, filed Aug. 16, 2012, which application claims benefit of priority to U.S. Provisional Patent Application No. 61/524,051 filed Aug. 16, 2011, which are incorporated herein by reference in their entireties.

FEDERALLY SPONSORED RESEARCH OR DEVELOPMENT

This invention was made with government support under CA135380 awarded by the National Institutes of Health. The government has certain rights in the invention.

BACKGROUND

Field of the Invention

The present invention relates generally to compounds and methods for treating cancer. More specifically, the present invention relates to the inhibition mechanism of the urokinase receptor to treat cancer.

Background of the Invention

When a primary tumor metastasizes, the prospects for survival become substantially worse, resulting in approximately 90% death in patients.[1] Metastasis occurs when cells from the primary tumor travel to distant sites and form new colonies. Cells escape from the primary tumors primarily through the circulatory system. These cells gain access to the vasculature as a result of multiple complex processes that involve invasion, migration, adhesion, and angiogenesis. A small number of cells that survive the voyage through the circulatory system arrive at new organ sites. Adhesion to and recognition of those sites in the endothelium is followed by re-entry through a process known as extravasation and result in the formation of a new tumor colony.

The urokinase receptor (uPAR) is a cell surface GPI-anchored protein that has been widely implicated with promoting metastasis. The receptor enhances pericellular proteolysis by serving as a docking site to the urokinase-type plasminogen activator (uPA), triggering a cascade of proteolytic events that include activation of plasminogen and matrix metalloproteinase (MMPs). The receptor also activates other cell signaling through lateral interactions with cell surface receptors that include integrins,[2] receptor tyrosine kinases (RTKs).[3,4]

The dual roles of the urokinase system in promoting degradation of the ECM and signaling have implicated the receptor with almost every step of tumor formation and progression, including tumorigenesis.[5-11]

SUMMARY

According to a first broad aspect, the presently disclosed subject matter provides a method for treating, inhibiting, delaying or preventing cancer in a subject, the method comprising administering to the subject a therapeutically effective amount of a compound of Formulae (I), (II), (III), or (IV):

Formula (I)

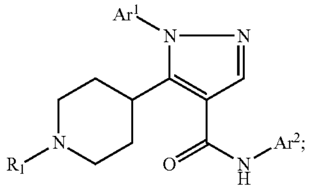

Formula (II)

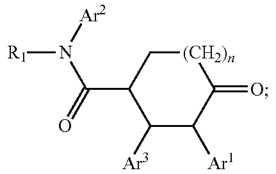

Formula (III)

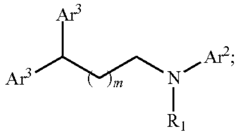

Formula (IV)

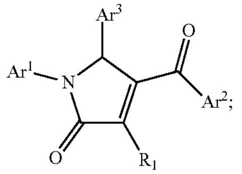

wherein: n is an integer selected from the group consisting of 0 and 1; m is an integer selected from the group consisting of 1, 2, 3, 4, 5, 6, 7, and 8; Ar1, Ar2, and Ar3 are each independently selected from the group consisting of substituted or unsubstituted cycloalkyl, substituted or unsubstituted cycloheteroalkyl, substituted or unsubstituted aryl, substituted or unsubstituted arylalkyl, substituted or unsubstituted heteroarylalkyl, and substituted or unsubstituted fused ring cycloalkyl or cycloheteroalkyl systems, substituted or unsubstituted fused ring aryl or heteroaryl systems, and substituted or unsubstituted fused ring cycloalkyl or cycloheteroalkyl/aryl or heteroaryl systems; each R1 is independently selected from the group consisting of H, alkyl, cycloalkyl, and hydroxyl; and pharmaceutically acceptable salts thereof. In certain aspects, the compound of Formulae (I-IV) inhibits binding of uPA to uPAR.

According to a second broad aspect, the presently disclosed subject matter provides a method for inhibiting a cancer cell or preventing the formation of a cancer cell from a noncancerous cell, the method comprising contacting the cancer or noncancerous cell with a compound of Formulae (I-IV) in an amount effective to inhibit binding of the urokinase-type plasminogen activator (uPA) to the urokinase receptor (uPAR).

According to a third broad aspect, the presently disclosed subject matter provides a method for inhibiting cell signaling involving cell surface receptors between at least two cells, the method comprising contacting at least one cell with a compound of Formulae (I-IV) in an amount effective to inhibit cell signaling.

Certain embodiments of the presently disclosed subject matter having been stated hereinabove, which are addressed in whole or in part by the presently disclosed subject matter, other embodiments will become evident as the description proceeds when taken in connection with the accompanying drawings and examples as best described herein below. In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE DRAWINGS

Figure 1A:
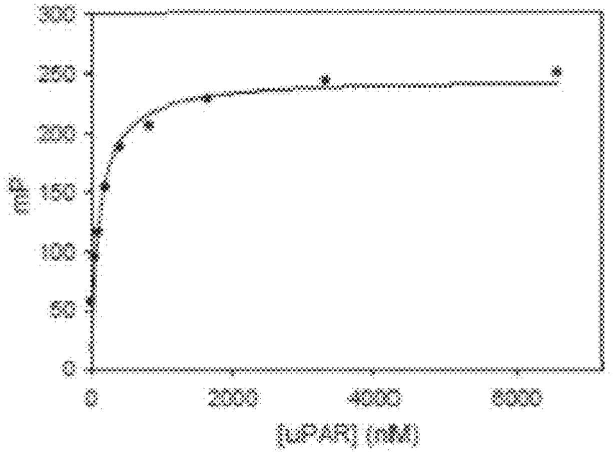

Having thus described the presently disclosed subject matter in general terms, reference will now be made to the accompanying drawings, which are not necessarily drawn to scale, and wherein:

FIG. 1A is graph showing binding of fluorescent GFD (AE147-FAM) as a function of uPAR.

Figure 1B:
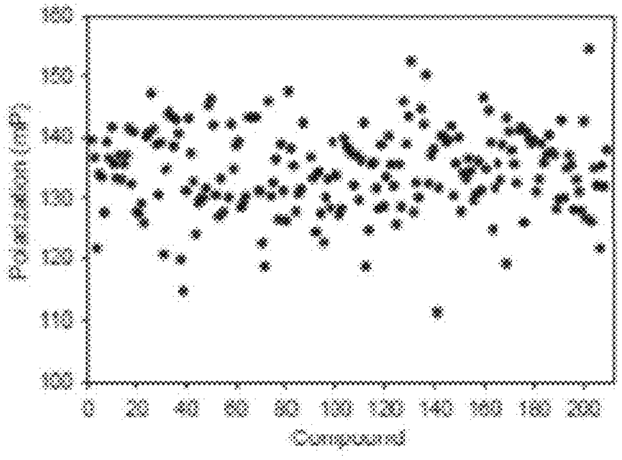

FIG. 1B is a graph showing fluorescence polarization for the top compounds that emerged from the computational screening.

Figure 1C:
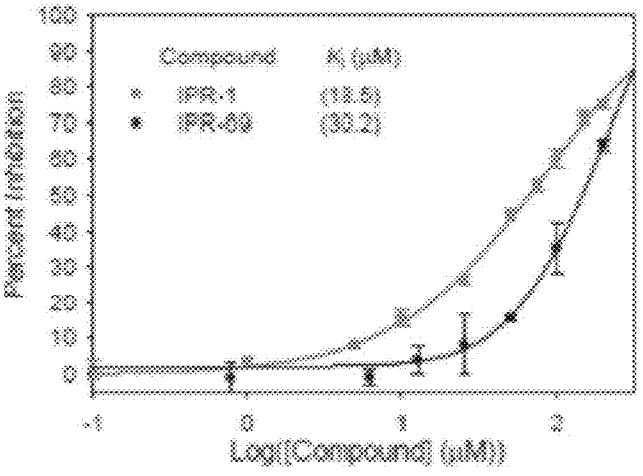

FIG. 1C is a graph showing abrogation of AE147-FAM binding to uPAR by IPR-1 and IPR-9 compounds inhibited in a concentration-dependent manner.

Figure 2A:
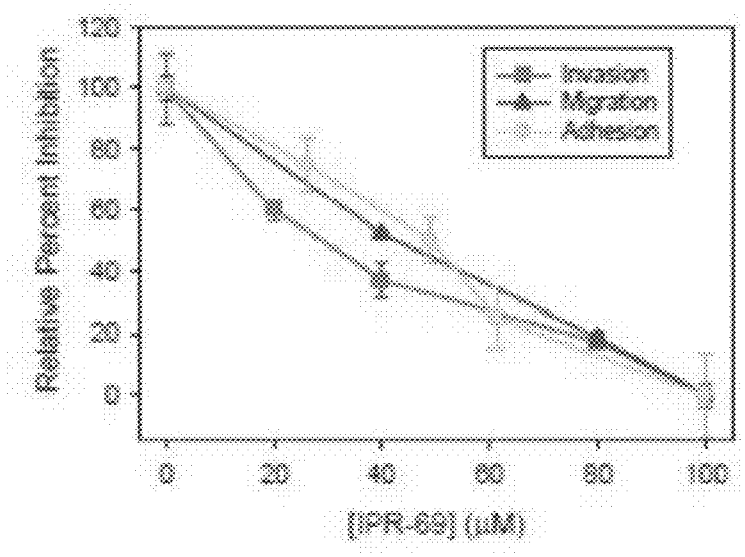

FIG. 2A is a graph showing concentration-dependent study of the effect of IPR-69 on MDA-MB-231 invasion, migration and adhesion.

Figure 2B:
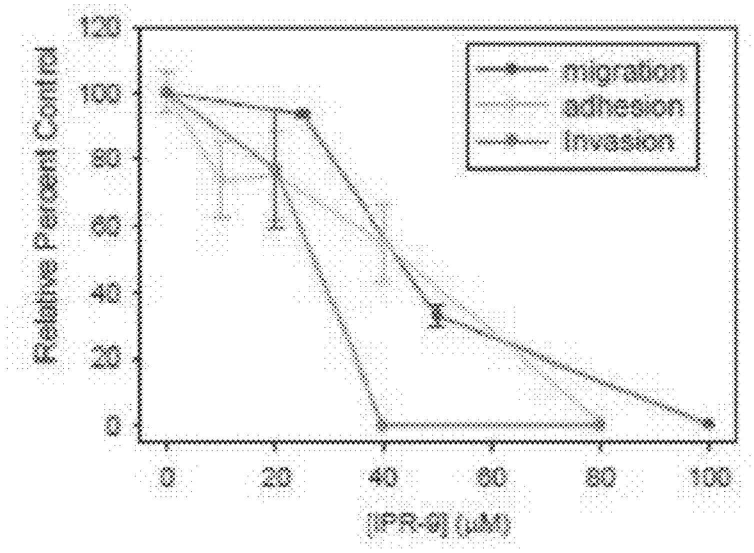

FIG. 2B is a graph showing concentration-dependent study of the effect of IPR-9 on MDA-MB-231 invasion, migration and adhesion.

Figure 3A:
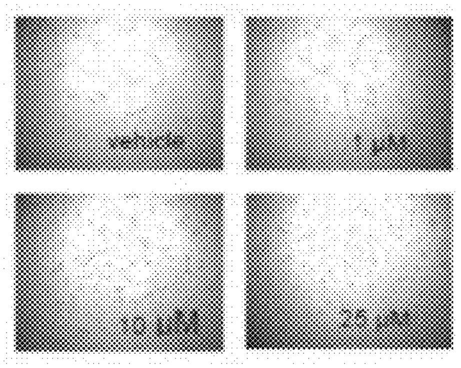

FIG. 3A is an image depicting formation of capillary-like tubes of HUVEC after addition of DMSO and increasing concentrations of IPR-69.

Figure 3B:
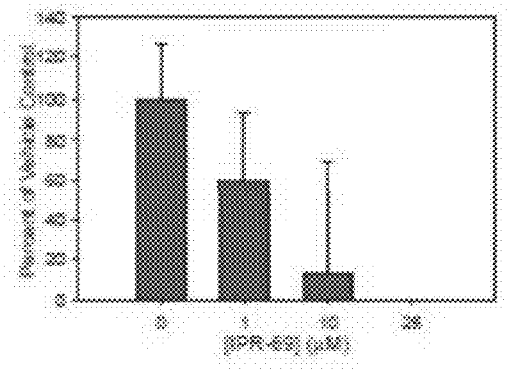

FIG. 3B is a graph showing percentage of tube formation to the vehicle group after addition of DMSO and increasing concentrations of IPR-69.

Figure 3C:
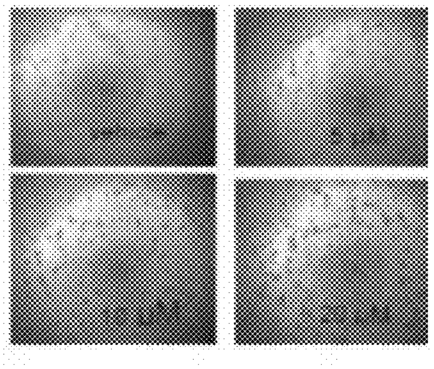

FIG. 3C is an image depicting formation of capillary-like tubes of HUVEC after addition of DMSO and increasing concentrations of IPR-9.

Figure 3D:
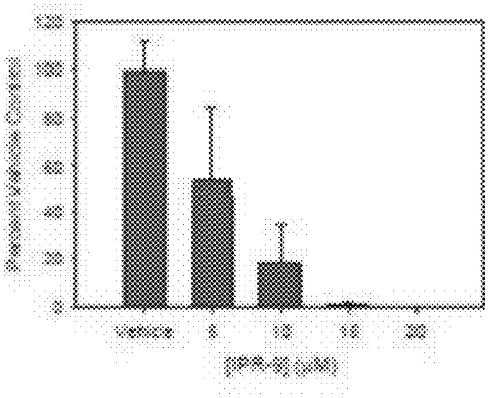

FIG. 3D is a graph showing percentage of tube formation to the vehicle group after addition of DMSO and increasting concentrations of IPR-9.

Figure 4A:
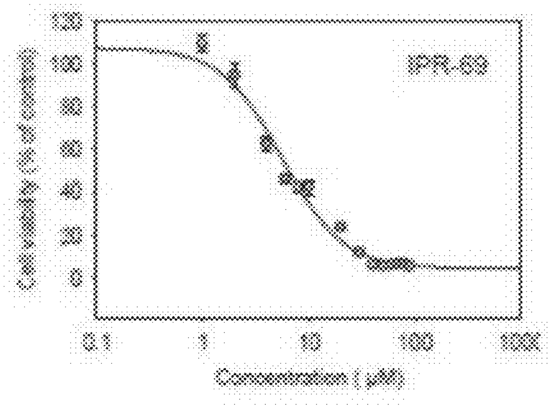

FIG. 4A is a curve graph of an MTT assay revealing inhibition of MDA-MB-21 proliferation by IPR-69.

Figure 4B:
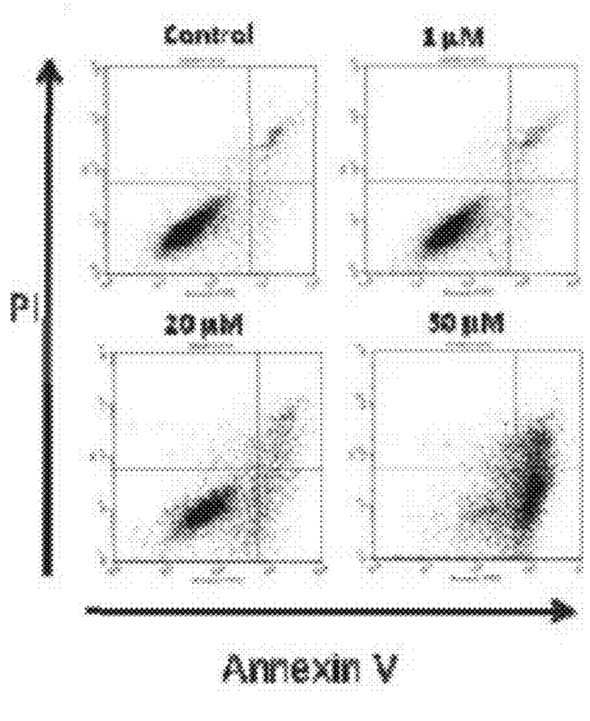

FIG. 4B is a histogram showing flow cytometry analysis of the MTT assay in FIG. 4A using Annexin V-FITC and PI staining.

Figure 4C:
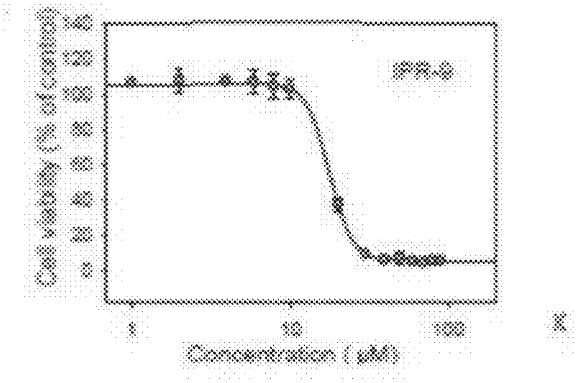

FIG. 4C is a curve graph of an MTT assay revealing inhibition of MDA-MB-21 proliferation by IPR-9.

Figure 4D:
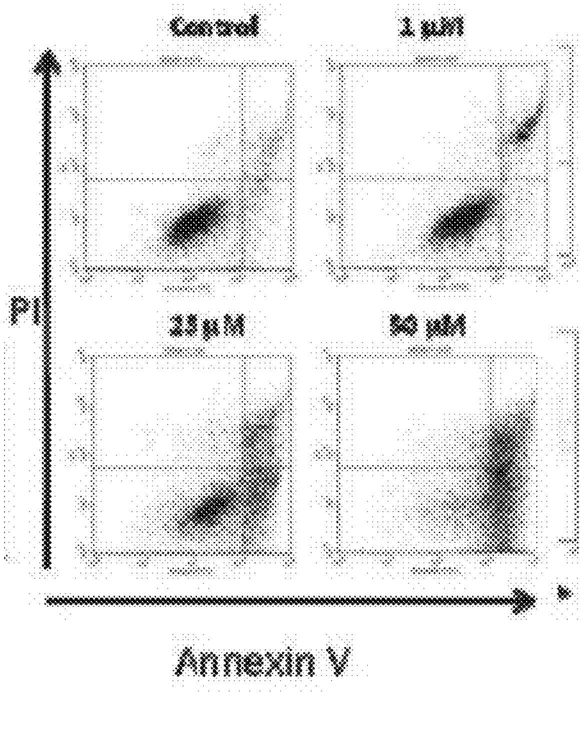

FIG. 4D is a histogram showing flow cytometry analysis of the MTT assay in FIG. 4C, using Annexin V-FITC and PI staining.

Figure 5A:
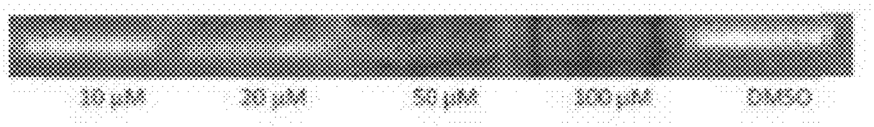

FIG. 5A is an image of gelatin zymography analysis for MDA-MB-231 with increasing concentrations of IPR-69.

Figure 5B:
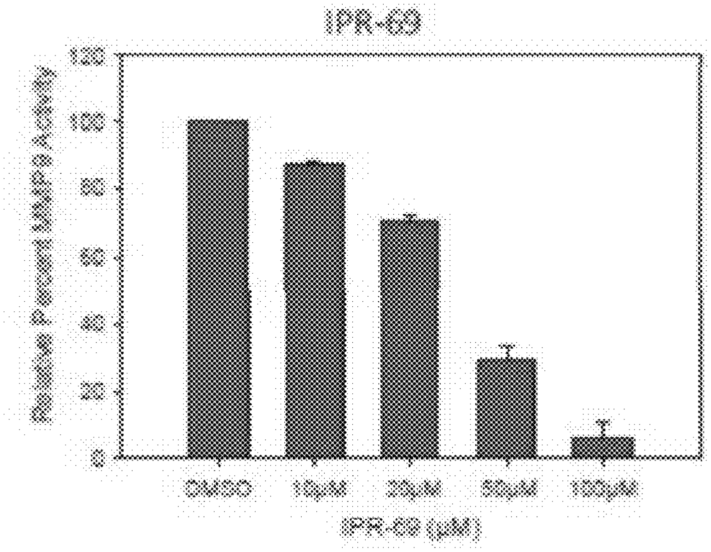

FIG. 5B is a bar graph of the gelatin zymography analysis of FIG. 5A.

Figure 5C:
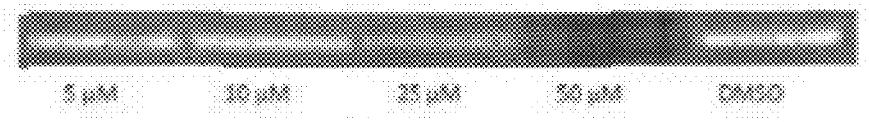

FIG. 5C is an image of gelatin zymography analysis for MDA-MB-231 with increasing concentrations of IPR-9.

Figure 5D:
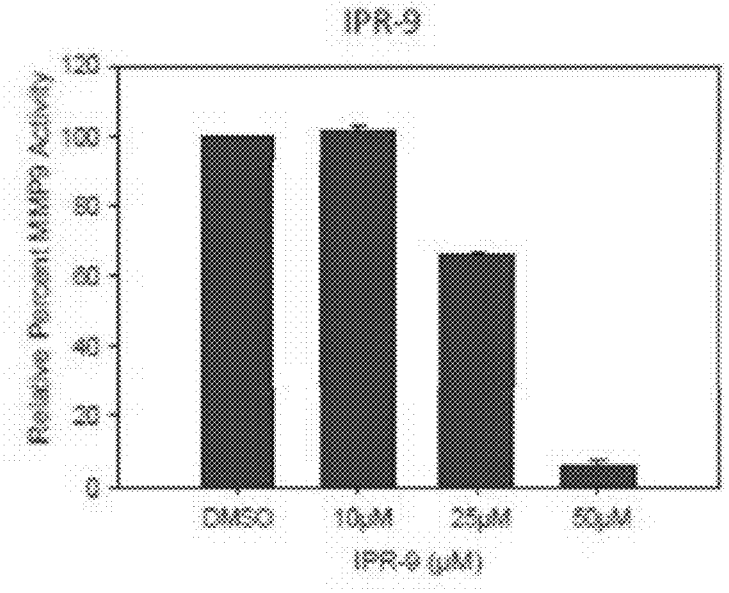

FIG. 5D is a bar graph of the gelatin zymography analysis of FIG. 5C.

Figure 6A:
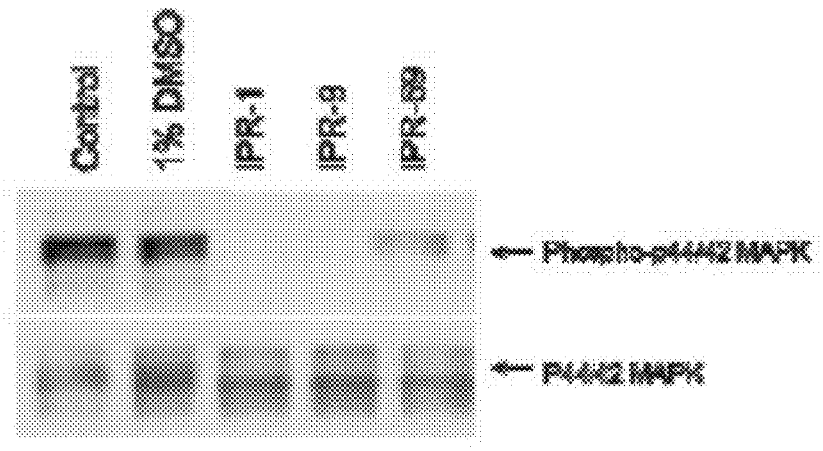

FIG. 6A is a compilation of images that demonstrate a cell signaling study wherein MDA-MB-231 is treated with 100 μM compound(s) for 30 min, then immunoblotted with phospho-p44/42 MAPK and p44/42 MAPK, respectively.

Figure 6B:
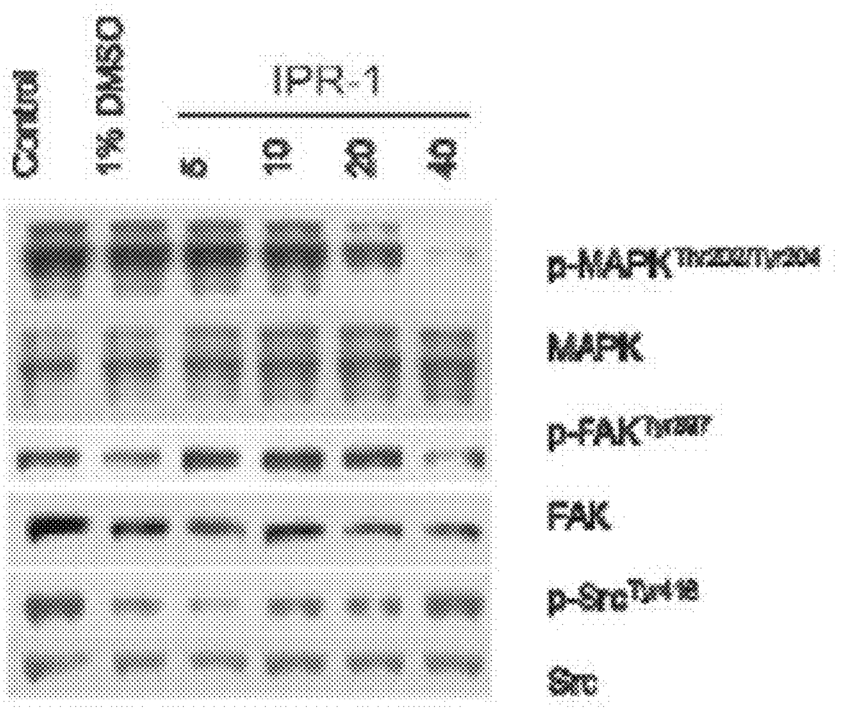

FIG. 6B is a compilation of images that demonstrate a cell signaling study wherein MDA-MB-231 is treated with 5, 10, 20 and 40 μM compound(s) for 30 min, then immunoblotted with phospho-p44/42 MAPK (Thr202/Tyr204), p44/42 MAPK; phospho-FAK (Tyr397), FAK; phospho-Src family (Tyr416), Src, respectively.

Figure 7A:
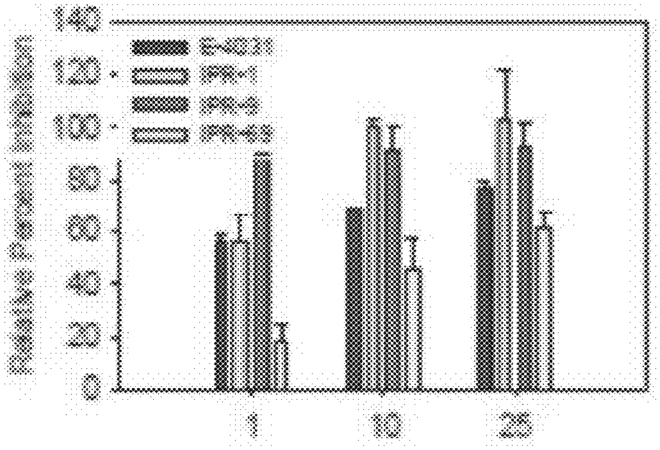

FIG. 7A is a graph showing percent inhibition of hERG K+, using E-4031 as control.

Figure 7B:
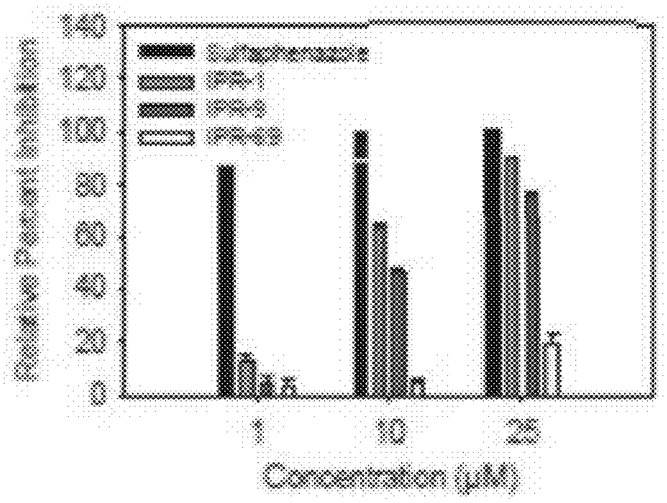

FIG. 7B is a graph showing percent inhibition of CYP2C9 isozyme, using Sulfaphenazole as control.

Figure 7C:
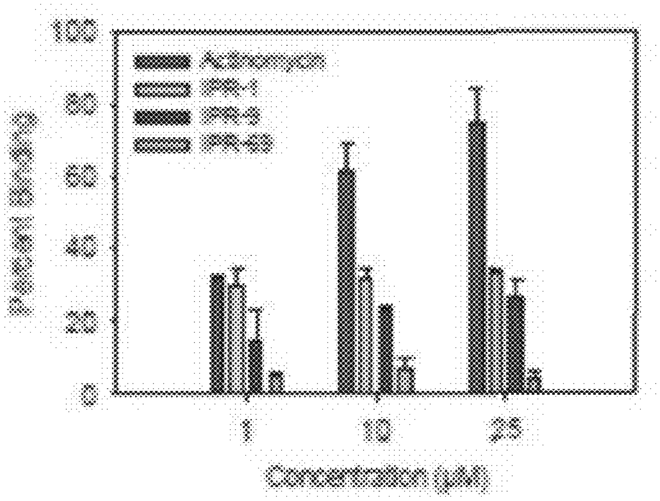
Figures 7D, 7E:
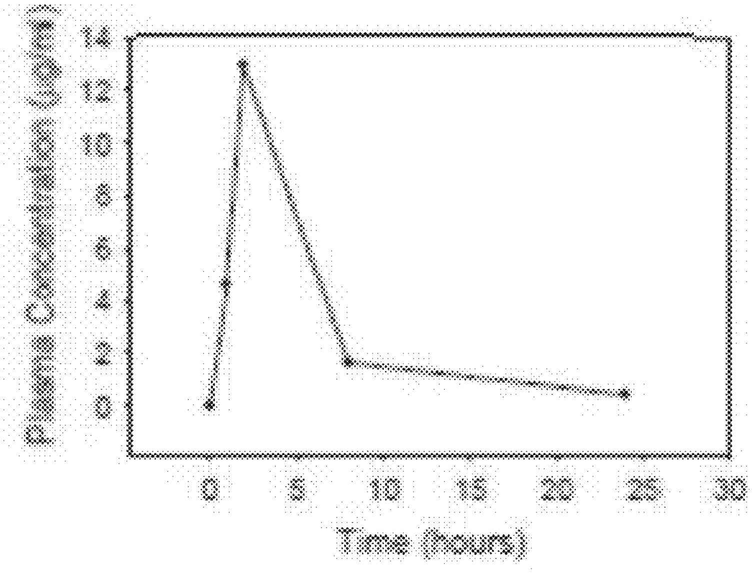

FIG. 7C is a graph showing DNA binding of compounds using fluorescence emission (excitation: 530 nm and Emission: 615 nm) of Calf thymus DNA bound to ethidium bromide (DNA-EB), using Actinomycin D (ActD), a known DNA intercalator, as positive Control;

FIG. 7D is a graph showing PK analysis of IPR-69 in female NOD/SCID mice (n=1 per time point) dosed by oral gavage as a mixture of 50 mg/kg in 0.5% hydroxy-methyl-propyl-cellulose.

FIG. 7E is a table showing in vivo PK parameters of the IPR-69 quantification and HPLC MS/MS analysis of FIG. 7D.

Figure 8A:
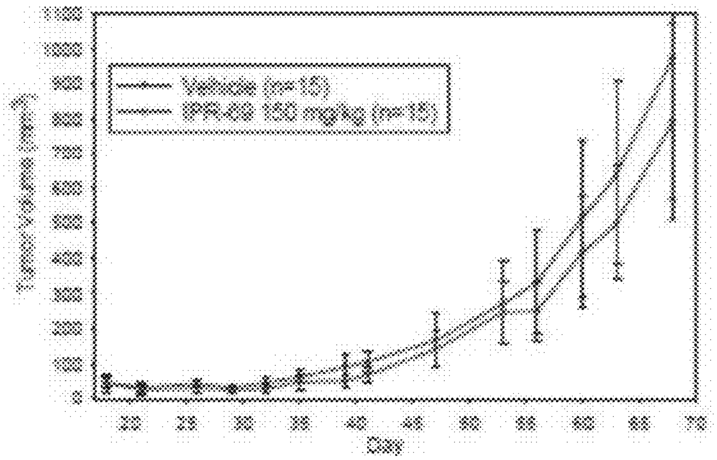

FIG. 8A is a graph showing effect of IPR-69 on MDA-MB-231 tumor growth when MDA-MB-231 cells were inoculated in the mammary fat pads of female NOD/SCID mice.

Figure 8B:
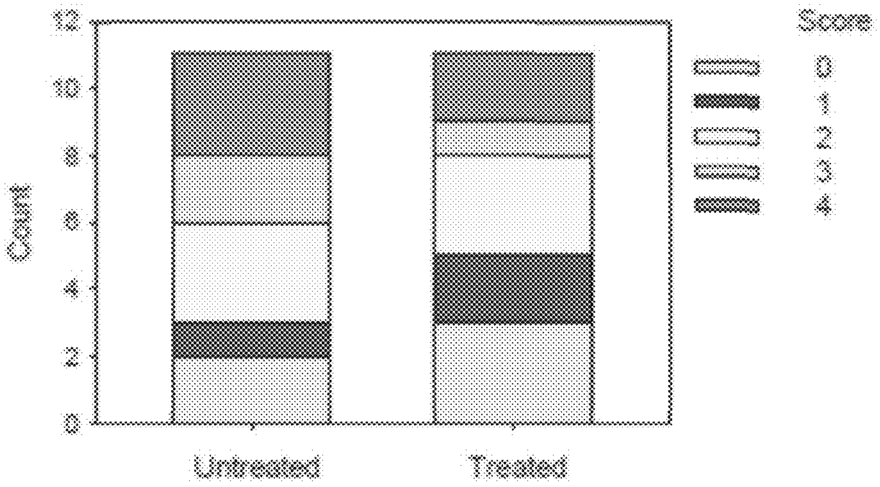

FIG. 8B is a graph showing the results of the semi-quantitative scoring system used for the estimation of TMA scoring.

Figure 8C:
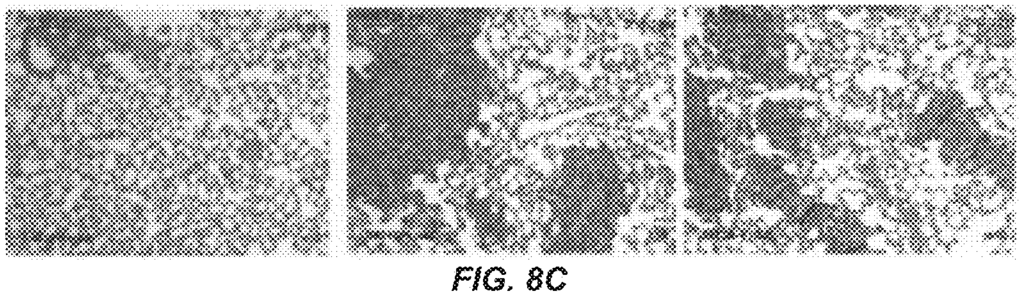

FIG. 8C is a series of staining images that illustrate metastasis in the lungs of animals.

Figure 9A:
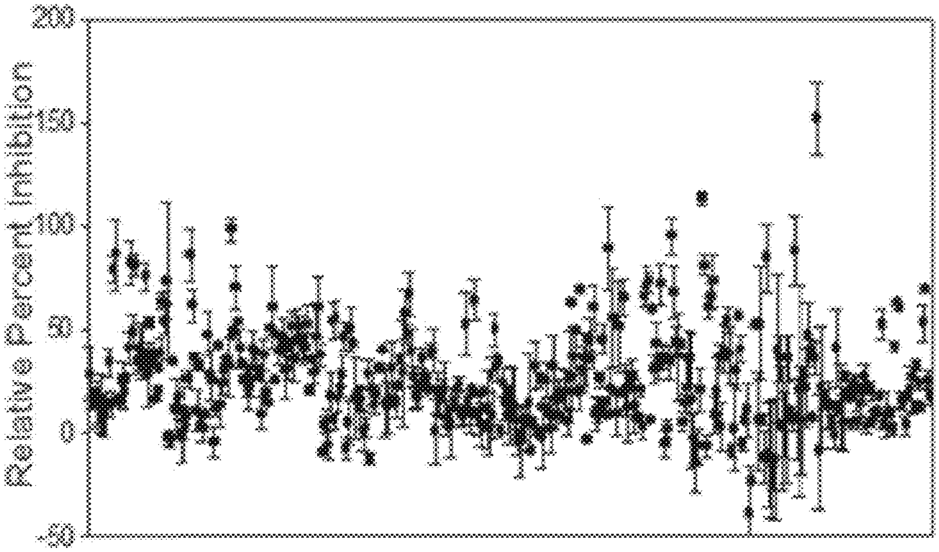

FIG. 9A is a bar graph showing fluorescence polarization of compounds that are derivatives of IPR-1, IPR-69, IPR-99 and IPR-108.

Figure 9B:
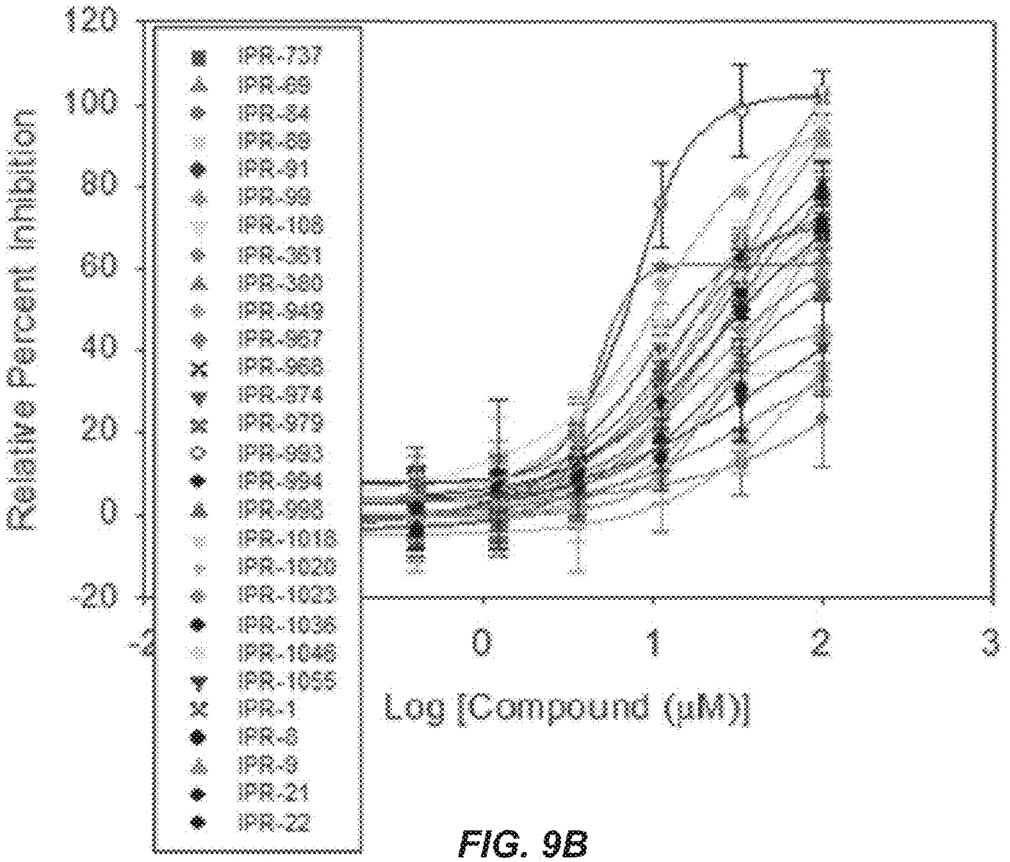
Figure 10A:
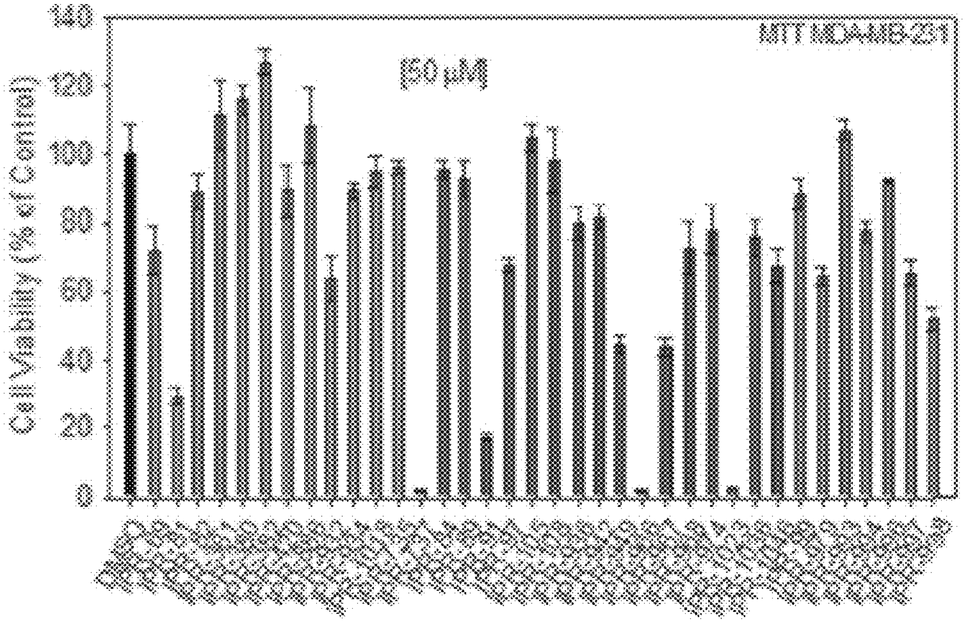

FIG. 9B is a curve graph showing fluorescence polarization of derivative compounds of FIG. 10A.

FIG. 10A is a bar graph an MTT assay in MDA-MB-231 using IPR-69/81 (left cluster), IPR-84/108 (middle cluster) and IPR-99 (right cluster) derivatives.

Figure 10B:
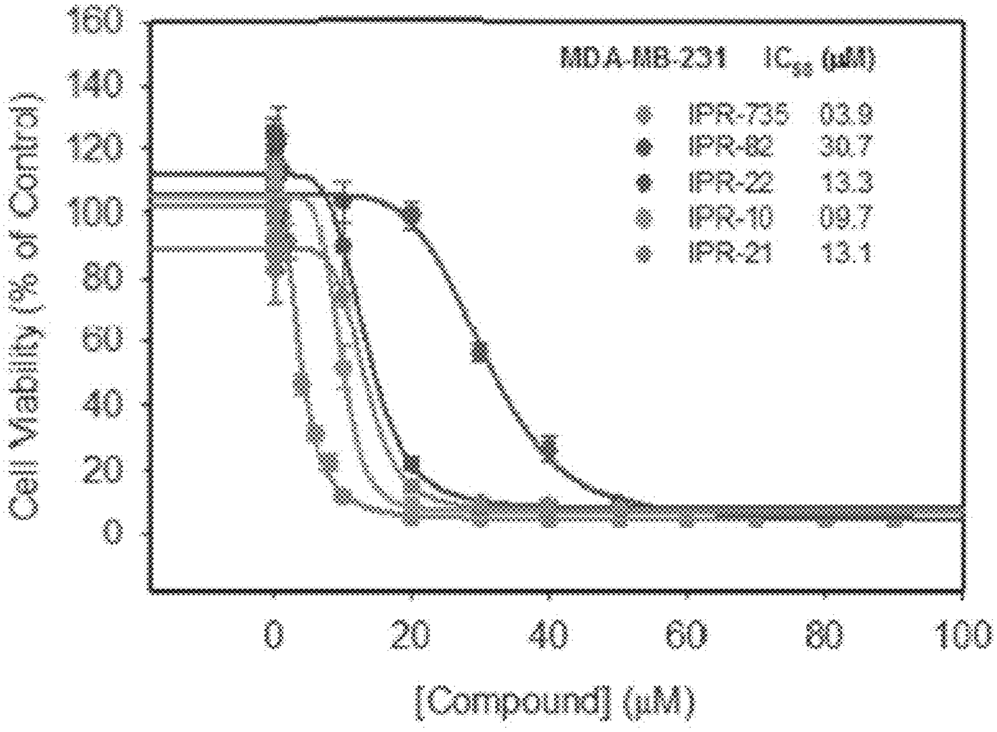

FIG. 10B is a curve graph of selected derivative compounds of the MTT assay in FIG. 10A.

Figure 11A:
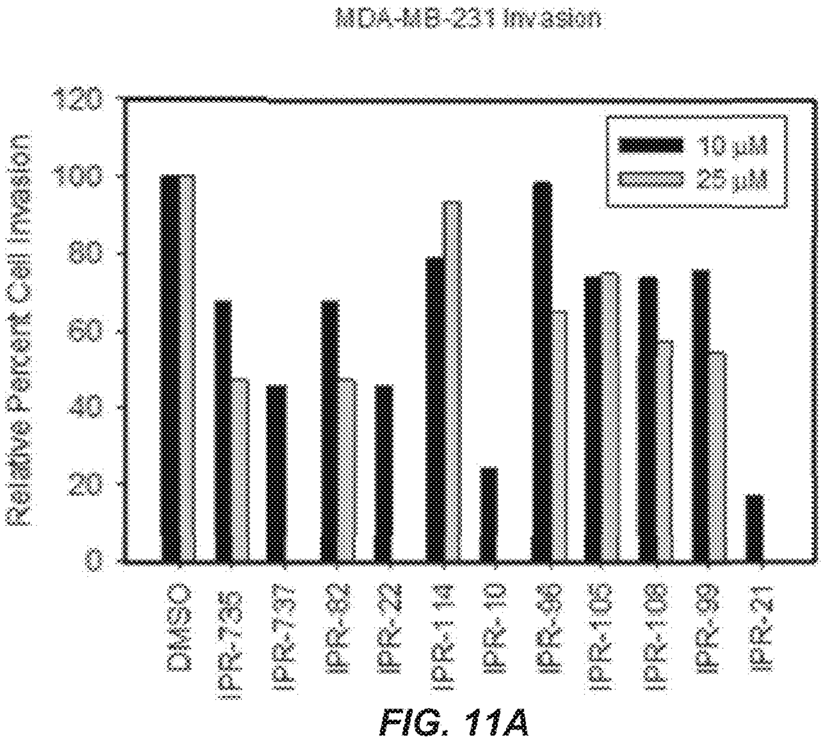

FIG. 11A is a bar graph showing cell invasion and cell migration assays in MDA-MB-231 cells.

Figure 11B:
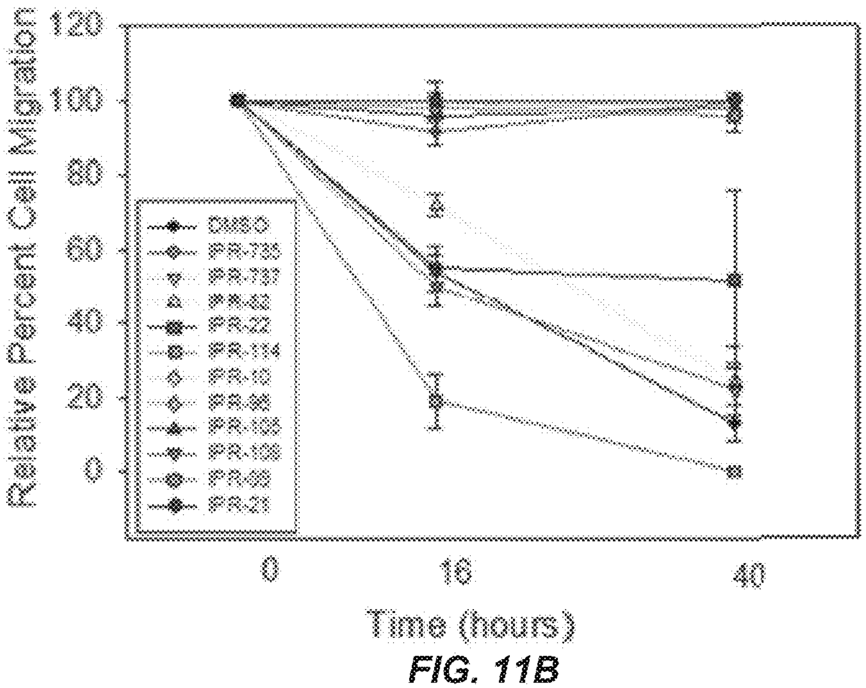

FIG. 11B is a line graph showing cell invasion and cell migration assays of FIG. 11A.

Figure 12A:
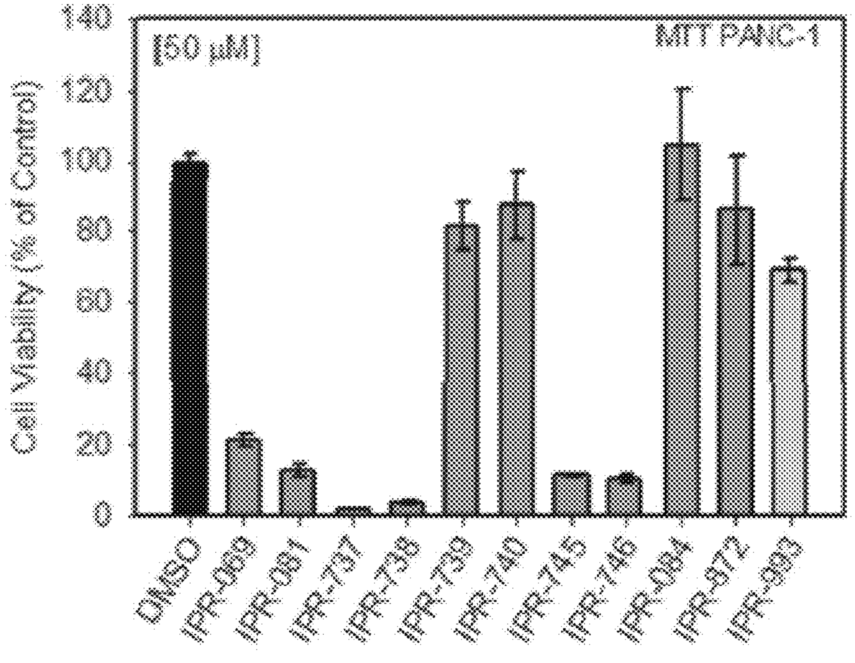

FIG. 12A is a bar graph showing an MTT assay using MDA-MB-231, AsPC-1, and PANC-1 cells.

Figure 12B:
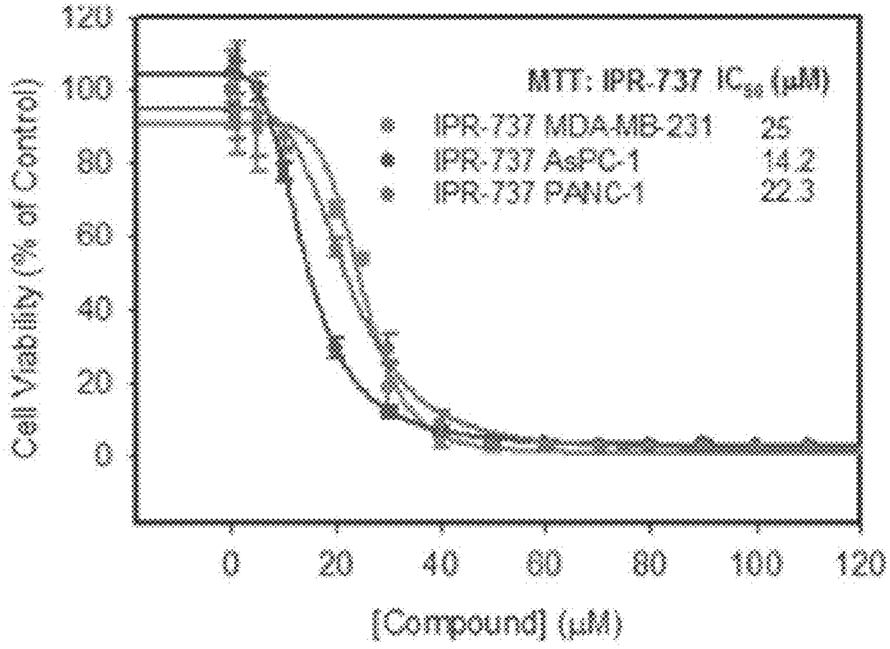

FIG. 12B is a curve graph showing the MTT assay of FIG. 12A.

Figure 13A:
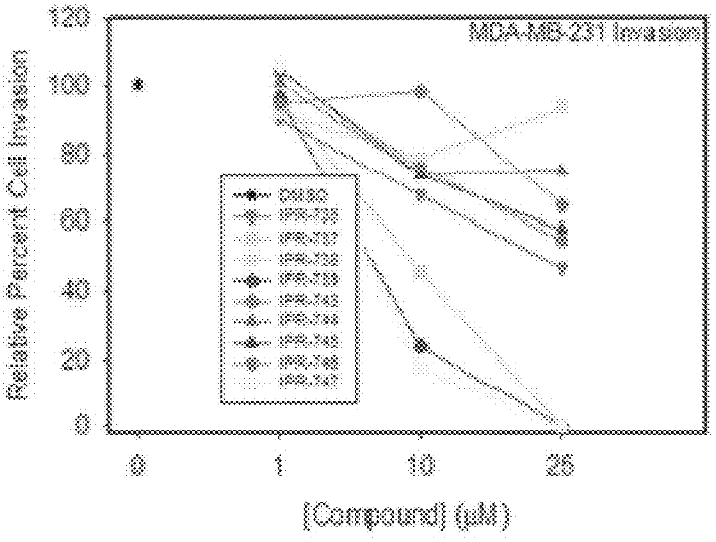

FIG. 13A is a line graph showing cell invasion (Fang Invasion n=1 in MDA-MB-231 cells) by compounds of the presently disclosed subject matter in MDA-MB-231 cells.

Figure 13B:
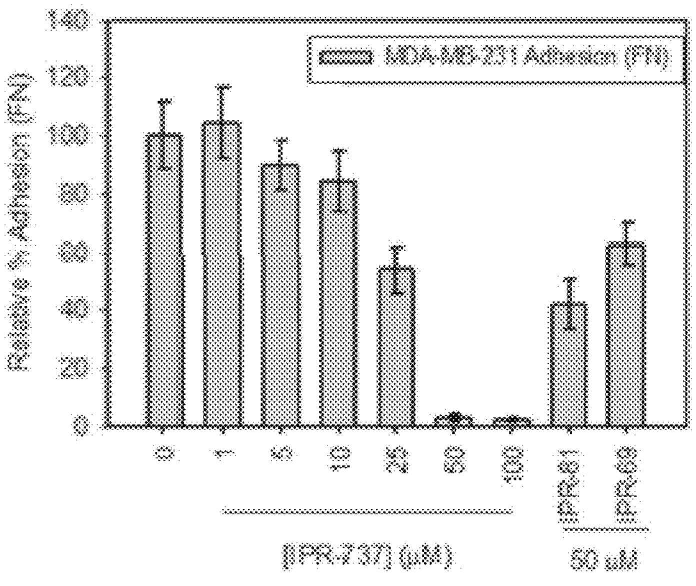

FIG. 13B is a bar graph showing cell adhesion by compounds of the presently disclosed subject matter in MDA-MB-231 cells.

Figure 13C:
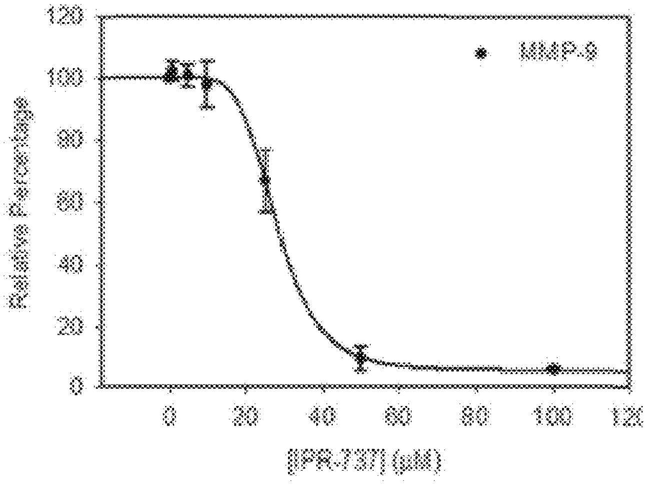

FIG. 13C is a curve graph showing an MMP-9 zymography (n=3; IPR-737 in MDA-MB-231 cells) assay with IPR-737 in MDA-MB-231 cells.

Figure 13D:
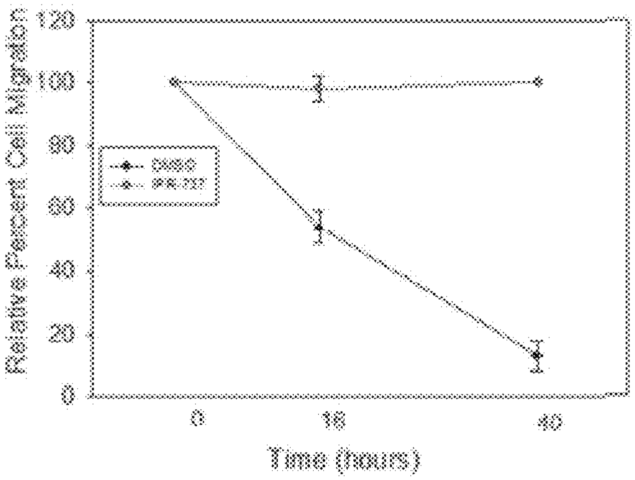

FIG. 13D is a line graph showing cell migration by compounds of the presently disclosed subject matter in MDA-MB-231 cells.

Figure 14:
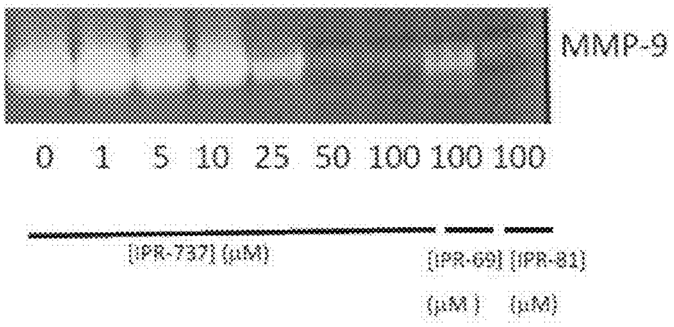

FIG. 14 is an image showing a MMP-9 zymography assay using MDA-MB-231 cells and IPR-737, IPR-69 and IPR-81 compounds.

Figure 15A:
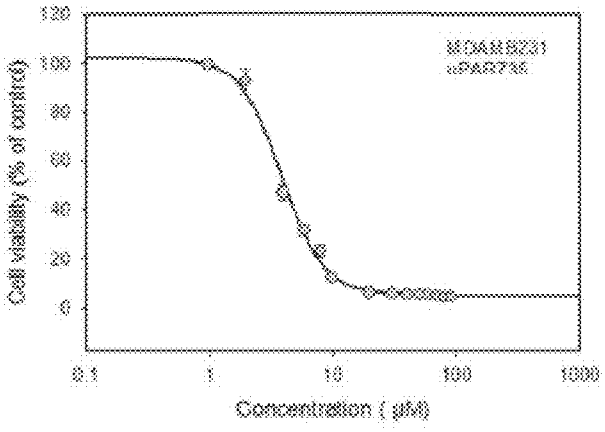

FIG. 15A is a curve graph showing cell viability of MDA-MB-231 cells with uPAR735.

Figure 15B:
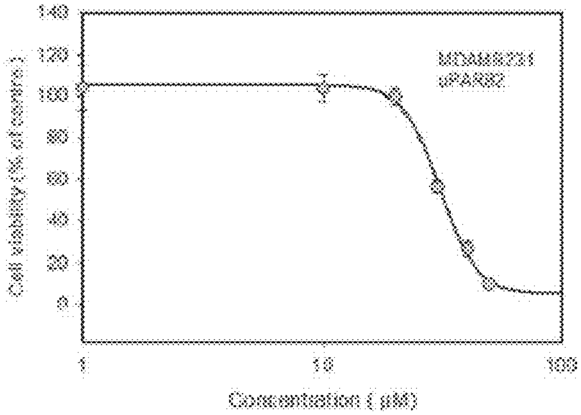

FIG. 15B is a curve graph showing cell viability of MDA-MB-231 cells with uPAR82.

Figure 15C:
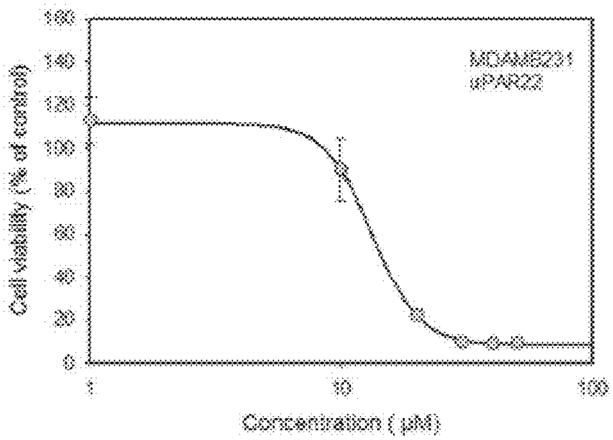

FIG. 15C is a curve graph showing cell viability of MDA-MB-231 cells with uPAR22.

Figure 15D:
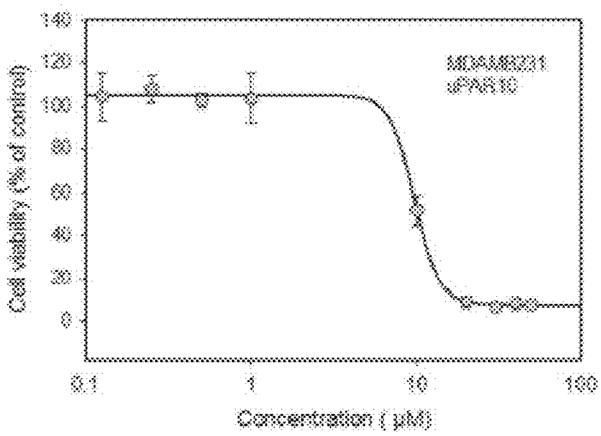

FIG. 15D is a curve graph showing cell viability of MDA-MB-231 cells with uPAR10.

Figure 15E:
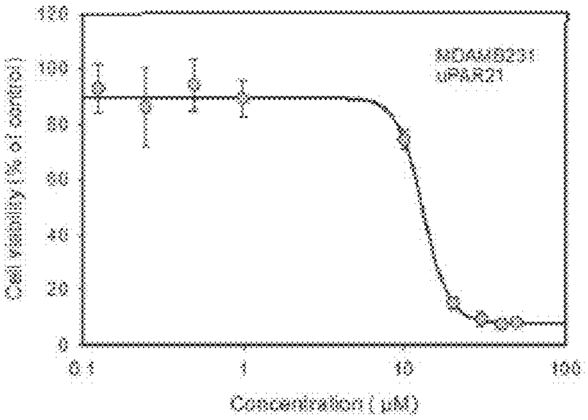

FIG. 15E is a curve graph showing cell viability of MDA-MB-231 cells with uPAR21.

Figure 16:
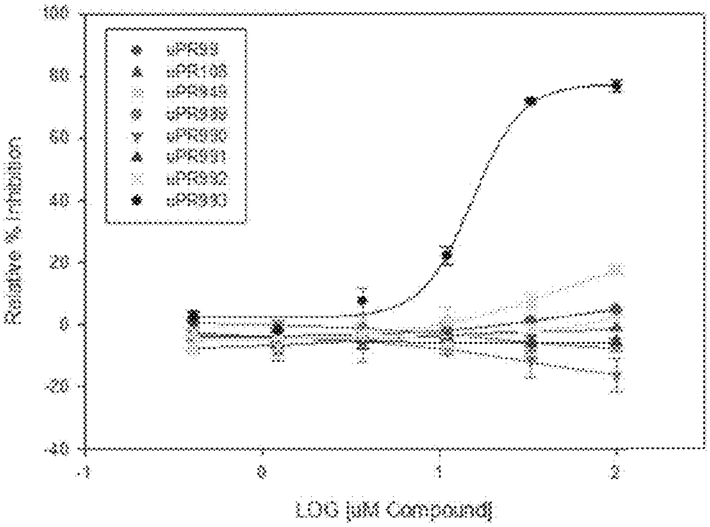

FIG. 16 is a curve graph showing some of the compounds of the presently disclosed subject matter in a uPAR microtiter binding assay.

Figure 17A:
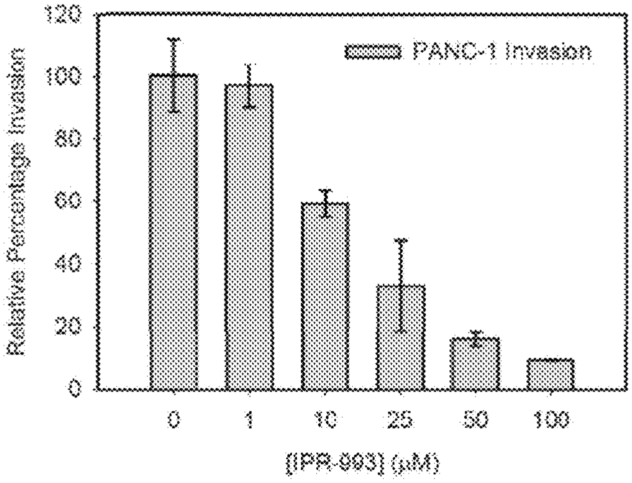

FIG. 17A is a bar graph showing a PANC-1 invasion assay with IPR-993 (n=1 in duplicates).

Figure 17B:
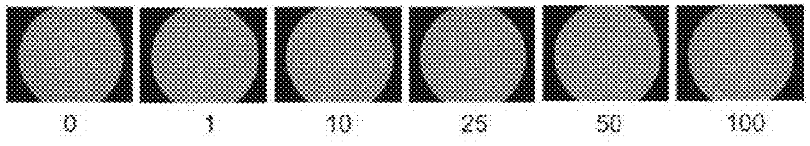

FIG. 17B is a series of images showing the PANC-1 invasion assay with IPR-993 of FIG. 18A.

Figure 18:
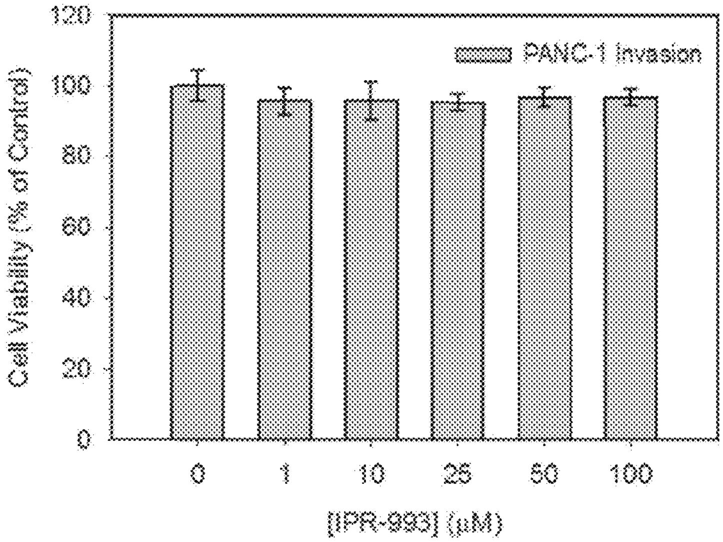

FIG. 18 is a bar graph showing cytotoxicity or cell viability in the PANC-1 invasion assay with IPR-993 of FIGS. 18A and 18B.

Figure 19A:
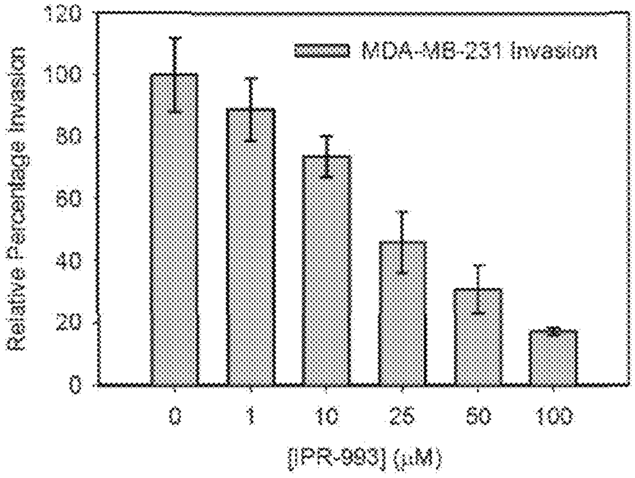

FIG. 19A is a bar graph showing an MDA-MB-231 invasion assay with IPR-993 (n=1 in duplicates).

Figure 19B:
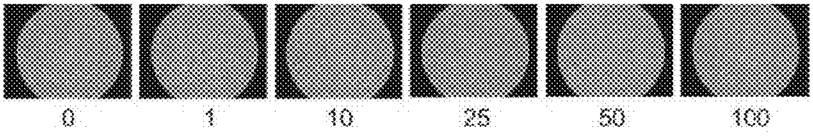

FIG. 19B is a series of images showing the MDA-MB-231 invasion assay with IPR-993 of FIG. 19A.

Figure 20A:
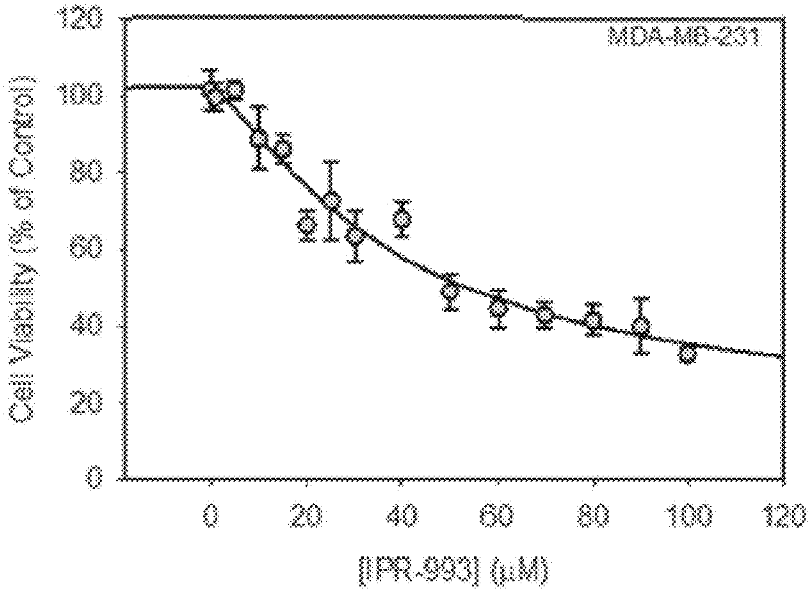

FIG. 20A is a curve graph showing cell viability in an MTT assay using MDA-MB-231 cells with IPR-993 (n=1 in duplicates).

Figure 20B:
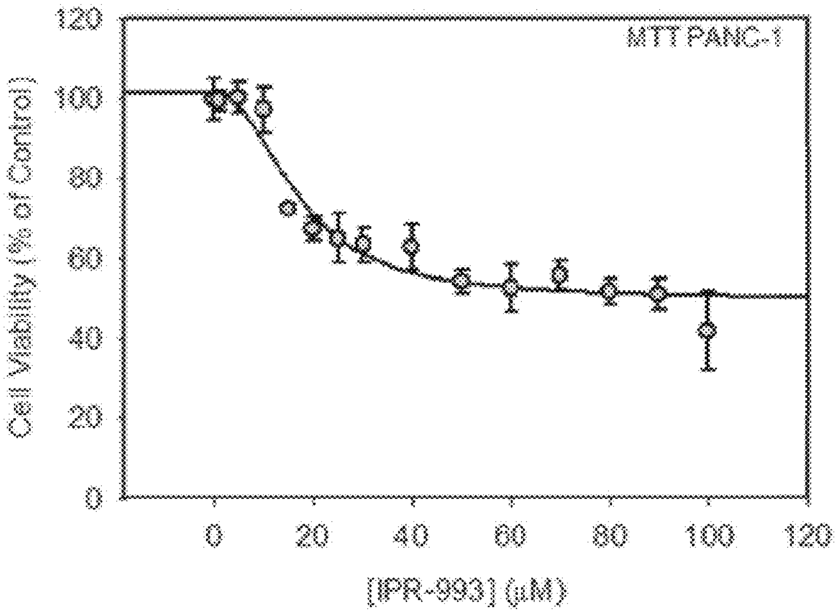

FIG. 20B is a curve graph showing cell viability in an MTT assay using PANC-1 cells with IPR-993 (n=1 in duplicates).

Figure 21A:
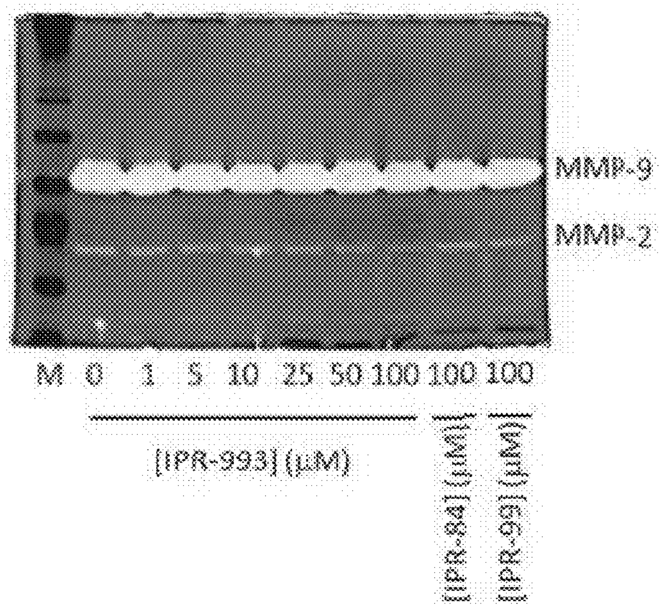

FIG. 21A is an image showing a MMP-9 zymography assay using MDA-MB-231 cells with IPR-993.

Figure 21B:
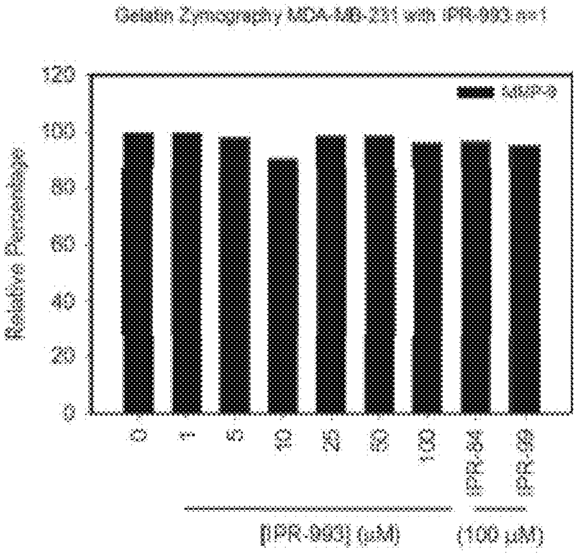

FIG. 21B is a bar graph showing the MMP-9 zymography assay of FIG. 22A.

Figure 22:
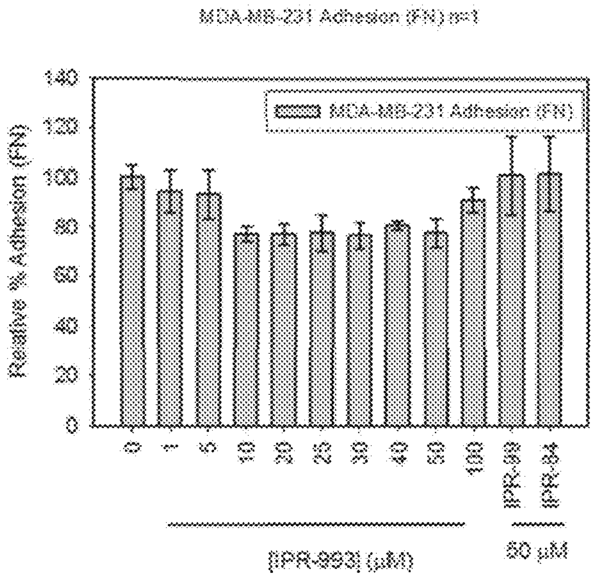

FIG. 22 is a bar graph showing a MDA-MB-231 adhesion assay with IPR-993 (FN; n=1).

Figure 23:
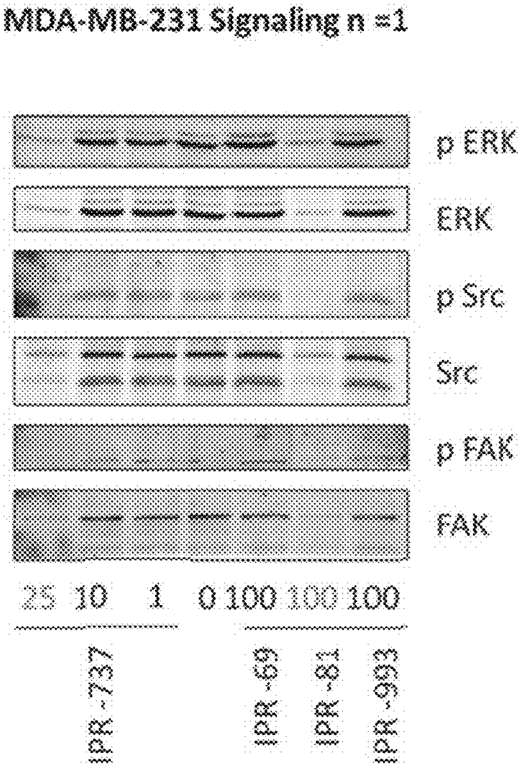

FIG. 23 is a compilation of images showing the effects of IPR-993, IPR-737, IPR-81, and IPR-69 on signaling by Western blot analysis (n=1; Lanes 1 and 6 are under-loaded).

DETAILED DESCRIPTION OF THE PREFERRED EMBODIMENTS

The presently disclosed subject matter now will be described more fully hereinafter with reference to the accompanying drawings, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated drawings. Therefore, it is to be understood that the presently disclosed subject matter is not to be limited to the specific embodiments disclosed and that modifications and other embodiments are intended to be included within the scope of the appended claims.

Definitions

Where the definition of terms departs from the commonly used meaning of the term, applicant intends to utilize the definitions provided below, unless specifically indicated.

For purposes of the present invention, the terms The terms "a," "an," or "a(n)," when used in reference to a group of substituents herein, mean at least one.

For purposes of the present invention, the term "acyl" refers to an organic acid group wherein the —OH of the carboxyl group has been replaced with another substituent and has the general formula RC(═O)—.

For purposes of the present invention, the term "acylamino" refers to an acyl-NH— group wherein acyl is as described herein.

For purposes of the present invention, the term "acyloxyl" refers to an acyl-O— group wherein acyl is as described herein.

For purposes of the present invention, the term "administering" refers to contacting a cancer cell with a compound of Formulae (I-IV). This term includes administration of the presently disclosed compounds to a subject in which the cancer cell is present, or suspected of being present, as well as introducing the presently disclosed compounds into a medium in which a cancer cell is cultured.

For purposes of the present invention, the term "agent" is meant a compound of Formulae (I-IV) or another agent, e.g., a peptide, nucleic acid molecule, or other small molecule compound administered in combination with a compound of Formulae (I-IV). More generally, the term "therapeutic agent" means a substance that has the potential of affecting the function of an organism. Such an agent may be, for example, a naturally occurring, semi-synthetic, or synthetic agent. For example, the therapeutic agent may be a drug that targets a specific function of an organism. A therapeutic agent also may be a nutrient. A therapeutic agent may decrease, suppress, attenuate, diminish, arrest, or stabilize the development or progression of disease, disorder, or condition in a host organism.

For purposes of the present invention, the term "alkoxycarbonyl" refers to an alkyl-O—CO— group.

For purposes of the present invention, the terms "alkoxyl" or "alkoxy" are used interchangeably herein and refer to a saturated (i.e., alkyl-O—) or unsaturated (i.e., alkenyl-O— and alkynyl-O—) group attached to the parent molecular moiety through an oxygen atom, wherein the terms "alkyl," "alkenyl," and "alkynyl" are as described herein and can include C1-20 inclusive, linear, branched, or cyclic, saturated or unsaturated oxo-hydrocarbon chains, including, for example, methoxyl, ethoxyl, propoxyl, isopropoxyl, n-butoxyl, sec-butoxyl, t-butoxyl, and n-pentoxyl, neopentoxyl, n-hexoxyl, and the like.

For purposes of the present invention, the term "alkoxyalkyl" as used herein refers to an alkyl-O-alkyl ether, for example, a methoxyethyl or an ethoxymethyl group.

For purposes of the present invention, the term "alkyl," by itself or as part of another substituent, means, unless otherwise stated, a straight (i.e., unbranched) or branched chain, acyclic or cyclic hydrocarbon group, or combination thereof, which may be fully saturated, mono- or polyunsaturated and can include di- and multivalent groups, having the number of carbon atoms designated (i.e., C1-C10 means one to ten carbons). In particular embodiments, the term "alkyl" refers to C1-20 inclusive, linear (i.e., "straight-chain"), branched, or cyclic, saturated or at least partially and in some cases fully unsaturated (i.e., alkenyl and alkynyl) hydrocarbon radicals derived from a hydrocarbon moiety containing between one and twenty carbon atoms by removal of a single hydrogen atom.

For purposes of the present invention, the term "alkylcarbamoyl" refers to a R'RN—CO— group wherein one of R and R' is hydrogen and the other of R and R' is alkyl and/or substituted alkyl as previously described.

For purposes of the present invention, the term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

For purposes of the present invention, the term "alkylene" by itself or a part of another substituent refers to a straight or branched bivalent aliphatic hydrocarbon group derived from an alkyl group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents."

For purposes of the present invention, the terms "alkylthioether" and "thioalkoxyl" refer to a saturated (i.e., alkyl-S—) or unsaturated (i.e., alkenyl-S— and alkynyl-S—) group attached to the parent molecular moiety through a sulfur atom.

For purposes of the present invention, the term "alkynyl" as used herein refers to a monovalent group derived from a straight or branched C1-20 hydrocarbon of a designed number of carbon atoms containing at least one carbon-carbon triple bond.

For purposes of the present invention, the term "aminoalkyl" refers to an amino group covalently bound to an alkylene linker. More particularly, the terms alkylamino, dialkylamino, and trialkylamino as used herein refer to one, two, or three, respectively, alkyl groups, as previously defined, attached to the parent molecular moiety through a nitrogen atom. The term alkylamino refers to a group having the structure —NHR' wherein R' is an alkyl group, as previously defined; whereas the term dialkylamino refers to a group having the structure —NR'R", wherein R' and R" are each independently selected from the group consisting of alkyl groups. The term trialkylamino refers to a group having the structure —NR'R"R'", wherein R', R", and R'" are each independently selected from the group consisting of alkyl groups. Additionally, R', R", and/or R'" taken together may optionally be —(CH2)k- where k is an integer from 2 to 6. The amino group is —NR'R", wherein R' and R" are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

For purposes of the present invention, the term "aralkoxycarbonyl" refers to an aralkyl-O—CO— group.

For purposes of the present invention, the term "aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

For purposes of the present invention, the term "aralkyloxyl" refers to an aralkyl-O— group wherein the aralkyl group is as previously described. An exemplary aralkyloxyl group is benzyloxyl.

For purposes of the present invention, the term "aroylamino" refers to an aroyl-NH— group wherein aroyl is as previously described.

For purposes of the present invention, the term "aryloxycarbonyl" refers to an aryl-O—CO— group.

For purposes of the present invention, the term "aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

For purposes of the present invention, the term "aryl" refers to, unless otherwise stated, an aromatic hydrocarbon substituent that can be a single ring or multiple rings (such as from 1 to 3 rings), which are fused together or linked covalently.

For purposes of the present invention, the terms "arylene" and "heteroarylene" refer to the divalent forms of aryl and heteroaryl, respectively.

For purposes of the present invention, the term "branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a C1-8 alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to C1-8 straight-chain alkyls. In other embodiments, "alkyl" refers, in particular, to C1-8 branched-chain alkyls.

For purposes of the present invention, the term "carbamoyl" refers to an amide group of the formula —CONH2.

For purposes of the present invention, the term "carbonyl" refers to the —(C═O)— group.

For purposes of the present invention, the term "carboxyl" refers to the —COOH group.

For purposes of the present invention, the terms "cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl, and fused ring systems, such as dihydro- and tetrahydronaphthalene, and the like.

For purposes of the present invention, the terms "cycloalkyl" and "heterocycloalkyl", by themselves or in combination with other terms, refer to, unless otherwise stated, cyclic versions of "alkyl" and "heteroalkyl", respectively. Additionally, for heterocycloalkyl, a heteroatom can occupy the position at which the heterocycle is attached to the remainder of the molecule. The terms "cycloalkylene" and "heterocycloalkylene" refer to the divalent derivatives of cycloalkyl and heterocycloalkyl, respectively.

For purposes of the present invention, the term "cycloalkylalkyl," refers to a cycloalkyl group as defined herein, which is attached to the parent molecular moiety through an alkyl group, also as defined herein. Examples of cycloalkylalkyl groups include cyclopropylmethyl and cyclopentylethyl.

For purposes of the present invention, the terms "cycloheteroalkyl" or "heterocycloalkyl" refer to a non-aromatic ring system, unsaturated or partially unsaturated ring system, such as a 3- to 10-member substituted or unsubstituted cycloalkyl ring system, including one or more heteroatoms, which can be the same or different, and are selected from the group consisting of nitrogen (N), oxygen (O), sulfur (S), phosphorus (P), and silicon (Si), and optionally can include one or more double bonds. The cycloheteroalkyl ring can be optionally fused to or otherwise attached to other cycloheteroalkyl rings and/or non-aromatic or aromatic hydrocarbon rings.

For purposes of the present invention, the term "decrease" refers to inhibit, suppress, attenuate, diminish, arrest, or stabilize a symptom of a disease, disorder, or condition. It will be appreciated that, although not precluded, treating a disease, disorder or condition does not require that the disease, disorder, condition or symptoms associated therewith be completely eliminated.

For purposes of the present invention, the term "dialkylcarbamoyl" refers to a R'RN—CO— group wherein each of R and R' is independently alkyl and/or substituted alkyl as previously described.

For purposes of the present invention, the term "effective amount," as in "a therapeutically effective amount," of a therapeutic agent refers to the amount of the agent necessary to elicit the desired biological response. As will be appreciated by those of ordinary skill in this art, the effective amount of an agent may vary depending on such factors as the desired biological endpoint, the agent to be delivered, the composition of the pharmaceutical composition, the target tissue or cell, and the like. More particularly, the term "effective amount" refers to an amount sufficient to produce the desired effect, e.g., to reduce or ameliorate the severity, duration, progression, or onset of a disease, disorder, or condition (e.g., a disease, condition, or disorder related to cancer), or one or more symptoms thereof; prevent the advancement of a disease, disorder, or condition, cause the regression of a disease, disorder, or condition; prevent the recurrence, development, onset or progression of a symptom associated with a disease, disorder, or condition, or enhance or improve the prophylactic or therapeutic effect(s) of another therapy.

For purposes of the present invention, the terms "halo," "halide," or "halogen" as used herein refer to fluoro, chloro, bromo, and iodo groups. Additionally, terms such as "haloalkyl," are meant to include monohaloalkyl and polyhaloalkyl.

For purposes of the present invention, the term "heteroalkyl," by itself or in combination with another term, refers to, unless otherwise stated, a stable straight or branched chain, or cyclic hydrocarbon group, or combinations thereof, consisting of at least one carbon atoms and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —CH2-CH2-O—CH3, —CH2-CH2-NH—CH3, —CH2-CH2-N(CH3)-CH3, —CH2-S—CH2-CH3, —CH2-CH25-S(O)—CH3, —CH2-CH2-S(O)2-CH3, —CH═CH—O—CH3, —Si(CH3)3, —CH2-CH═N—OCH3, —CH═CH—N(CH3)-CH3, —O—CH3, —O—CH2-CH3, and —CN. Up to two or three heteroatoms may be consecutive, such as, for example, —CH2-NH—OCH3 and —CH2-O—Si(CH3)3. Thus, as described above, heteroalkyl groups, as used herein, include those groups that are attached to the remainder of the molecule through a heteroatom, such as —C(O)R', —C(O)NR', —NR'R", —OR', —SR, and/or —SO2R'. Where "heteroalkyl" is recited, followed by recitations of specific heteroalkyl groups, such as —NR'R or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

For purposes of the present invention, the term "heteroalkylene" by itself or as part of another substituent refers to a divalent group derived from heteroalkyl, as exemplified, but not limited by, —CH2-CH2-S—CH2-CH2- and —CH2-S—CH2-CH2-NH—CH2-.

For purposes of the present invention, the term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom.

For purposes of the present invention, the term "homoalkyl" refers to an alkyl group which is limited to hydrocarbon groups.

For purposes of the present invention, the term "hydrocarbon" refers to any chemical group comprising hydrogen and carbon. The hydrocarbon may be substituted or unsubstituted. As would be known to one skilled in this art, all valencies must be satisfied in making any substitutions. The hydrocarbon may be unsaturated, saturated, branched, unbranched, cyclic, polycyclic, or heterocyclic. Illustrative hydrocarbons are further defined herein below and include, for example, methyl, ethyl, n-propyl, iso-propyl, cyclopropyl, allyl, vinyl, n-butyl, tert-butyl, ethynyl, cyclohexyl, methoxy, diethylamino, and the like.

For purposes of the present invention, the term "hydroxyl" refers to the —OH group.

For purposes of the present invention, the term "hydroxyalkyl" refers to an alkyl group substituted with an —OH group.

For purposes of the present invention, the term "in combination with" refers to the administration of a compound of Formulae (I-IV) with one or more therapeutic agents either simultaneously, sequentially, or a combination thereof.

For purposes of the present invention, when the term "independently selected" is used, the substituents being referred to (e.g., R groups, such as groups R1, R2, and the like, or variables, such as "m" and "n"), can be identical or different. For example, both R1 and R2 can be substituted alkyls, or R1 can be hydrogen and R2 can be a substituted alkyl, and the like.

For purposes of the present invention, the terms "inhibit" or "inhibits" refer to decrease, suppress, attenuate, diminish, arrest, or stabilize the development or progression of a disease, disorder, or condition, or the activity of a biological pathway, e.g., by at least 10%, 20%, 30%, 40%, 50%, 60%, 70%, 80%, 90%, 95%, 98%, 99%, or even 100% compared to an untreated control subject, cell, or biological pathway. In some embodiments, "inhibit" means reducing the size of a tumor. In other embodiments, "inhibit" means to reduce the amount of metastasis within a tumor site or outside the tumor site.

For purposes of the present invention, the terms "lower substituent" and "lower substituent group," refer to a group selected from all of the substituents described hereinabove for a "substituent group," wherein each substituted or unsubstituted alkyl is a substituted or unsubstituted C1-C8 alkyl, each substituted or unsubstituted heteroalkyl is a substituted or unsubstituted 2 to 8 membered heteroalkyl, each substituted or unsubstituted cycloalkyl is a substituted or unsubstituted C5-C7 cycloalkyl, and each substituted or unsubstituted heterocycloalkyl is a substituted or unsubstituted 5 to 7 membered heterocycloalkyl.

For purposes of the present invention, the term "mercapto" refers to the —SH group.

For purposes of the present invention, the term "nitro" refers to the —NO2 group.

For purposes of the present invention, the term "noncancerous" refers to a cell or subject that is not affected with or being cancer. Noncancerous cells do not show unregulated growth and are not capable of expanding locally by invasion and systemically by metastasis. Cancer affects biological processes such as cell migration, cell growth, cell adhesion, angiogenesis, apoptosis, integrity of the extracellular matrix, pericellular proteolysis, and the like.

For purposes of the present invention, the term "oxo" as used herein means an oxygen atom that is double bonded to a carbon atom or to another element.

For purposes of the present invention, the terms "parenteral administration" and "administered parenterally" refer to modes of administration other than enteral and topical administration, usually by injection, and includes, without limitation, intravenous, intramuscular, intarterial, intrathecal, intracapsular, intraorbital, intraocular, intracardiac, intradermal, intraperitoneal, transtracheal, subcutaneous, subcuticular, intraarticular, subcapsular, subarachnoid, intraspinal and intrasternal injection and infusion.

For purposes of the present invention, the term "pharmaceutically acceptable salts" refers to and includes salts of active compounds, which are prepared with relatively nontoxic acids or bases, depending on the particular substituent moieties found on the compounds described herein.

For purposes of the present invention, the term "physiologically compatible carrier" refers to a physiologically acceptable diluent including, but not limited to water, phosphate buffered saline, or saline, and, in some embodiments, can include an adjuvant.

For purposes of the present invention, the terms "prevent," "preventing," "prevention," "prophylactic treatment" and the like refer to reducing the probability of developing a disease, disorder, or condition in a subject, who does not have, but is at risk of or susceptible to developing a disease, disorder, or condition. Thus, in some embodiments, an agent can be administered prophylactically to prevent the onset of a disease, disorder, or condition, or to prevent the recurrence of a disease, disorder, or condition.

For purposes of the present invention, the term "protecting group" refers to chemical moieties that block some or all reactive moieties of a compound and prevent such moieties from participating in chemical reactions until the protective group is removed.

For purposes of the present invention, the terms "size-limited substituent" and "size-limited substituent group," refer to a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, and each substituted or unsubstituted heterocycloalkyl is a substituted or unsubstituted 4 to 8 membered heterocycloalkyl.

For purposes of the present invention, the term "subject" refers to, desirably a human subject, although it is to be understood that the methods described herein are effective with respect to all vertebrate species, which are intended to be included in the term "subject." Accordingly, for purposes of the present invention, the term "subject" can include a human subject for medical purposes, such as for the treatment of an existing disease, disorder, condition or the prophylactic treatment for preventing the onset of a disease, disorder, or condition or an animal subject for medical, veterinary purposes, or developmental purposes. Suitable animal subjects include mammals including, but not limited to, primates, e.g., humans, monkeys, apes, gibbons, chimpanzees, orangutans, macaques and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, guinea pigs, and the like. An animal may be a transgenic animal. In some embodiments, the subject is a human including, but not limited to, fetal, neonatal, infant, juvenile, and adult subjects. Further, the term "subject" can include a patient afflicted with or suspected of being afflicted with a disease, disorder, or condition. Thus, the terms "subject" and "patient" are used interchangeably herein. Subjects also include animal disease models (e.g., rats or mice used in experiments, e.g., optic crush experiments, and the like). In particular embodiments, the subject is suffering from or susceptible to a disease, disorder, or condition, such as a cancer, including, but not limited to breast cancer or pancreatic cancer, e.g., a subject diagnosed as suffering from or susceptible to breast cancer or pancreatic cancer. In other embodiments, the subject has been identified (e.g., diagnosed) as suffering from or susceptible to a cancer, e.g., breast cancer or pancreatic cancer, for which treatment or prophylaxis is desired.

For purposes of the present invention, the term "substituted alkyl" refers to alkyl groups that can optionally be substituted (a "substituted alkyl") with one or more alkyl group substituents, which can be the same or different. Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

For purposes of the present invention, the term "sulfate" refers to the —SO4 group.

For purposes of the present invention, the terms "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

For purposes of the present invention, the term "thio" refers to a compound described previously herein wherein a carbon or oxygen atom is replaced by a sulfur atom.

For purposes of the present invention, the term "thiohydroxyl" or "thiol", as used herein, refers to a group of the formula —SH.

For purposes of the present invention, the terms "treat," "treating," "treatment," and the like, refer to decrease, suppress, attenuate, diminish, arrest, the underlying cause of a disease, disorder, or condition, or to stabilize the development or progression of a disease, disorder, condition, and/or symptoms associated therewith. The terms "treat," "treating," "treatment," and the like, as used herein can refer to curative therapy, prophylactic therapy, and preventative therapy. The treatment, administration, or therapy can be consecutive or intermittent. Consecutive treatment, administration, or therapy refers to treatment on at least a daily basis without interruption in treatment by one or more days. Intermittent treatment or administration, or treatment or administration in an intermittent fashion, refers to treatment that is not consecutive, but rather cyclic in nature. Treatment according to the presently disclosed methods can result in complete relief or cure from a disease, disorder, or condition, or partial amelioration of one or more symptoms of the disease, disease, or condition, and can be temporary or permanent. The term "treatment" also is intended to encompass prophylaxis, therapy and cure.

For purposes of the present invention, the term "ureido" refers to a urea group of the formula —NH—CO—NH2.

Virtual Screening Targeting uPAR, Biochemical and Cell-based Studies, Synthesis. Pharmacokinetic Characterization, and Effect on Breast Tumor Metastasis A docking-based virtual screening method was used to identify small molecules that bind uPAR. Accordingly, representative compounds disclosed herein modulate interactions of uPAR and block invasion and metastasis in vivo.

A. Methods of Treatment

In some embodiments, the presently disclosed subject matter provides a method for treating, inhibiting, delaying or preventing cancer in a subject, the method comprising administering to the subject a therapeutically effective amount of a compound of Formulae (I), (II), (III), or (IV):

Formula (I)

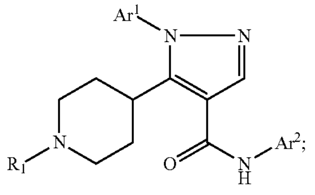

Formula (II)

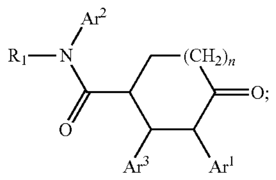

Formula (III)

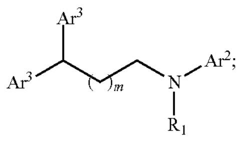

-continued

Formula (IV)

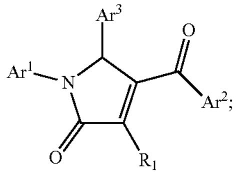

wherein: n is an integer selected from the group consisting of 0 and 1; m is an integer selected from the group consisting of 1, 2, 3, 4, 5, 6, 7, and 8; Ar1, Ar2, and Ar3 are each independently selected from the group consisting of substituted or unsubstituted cycloalkyl, substituted or unsubstituted cycloheteroalkyl, substituted or unsubstituted aryl, substituted or unsubstituted arylalkyl, substituted or unsubstituted heteroarylalkyl, and substituted or unsubstituted fused ring cycloalkyl or cycloheteroalkyl systems, substituted or unsubstituted fused ring aryl or heteroaryl systems, and substituted or unsubstituted fused ring cycloalkyl or cycloheteroalkyl/aryl or heteroaryl systems; each R1 is independently selected from the group consisting of H, alkyl, cycloalkyl, and hydroxyl; and pharmaceutically acceptable salts thereof.

In some embodiments, the compound is a compound of Formula (I) and Ar1 is selected from the group consisting of 4-isopropylphenyl and 3,4-dimethylphenyl; Ar2 is selected from the group consisting of 2-aminophenethylalcohol; 2-amino-3-methylbenzylalcohol; 3'-aminoacetanilide; 3-aminophenol; 4-amino-2,5-dimethylphenol; 2-aminobenzylalcohol; 2'-aminoacetanilide; 8-aminoquinoline; 3-methoxy-5-trifluoromethylbenzyl; 5-methoxy-2-methylbenzyl; 2-benzyloxy; 3-methylbenzyl; 2-(p-tolyl)ethyl; 3-fluorophenethyl; 2-fluorophenethyl; 4-fluorophenethyl; 4-isopropylbenzyl; 4-propylbenzyl; 4-tert-butylbenzyl; 4-bromophenylbenzyl; 5-chloro-2-methoxybenzyl; 4-methoxy-2-methylbenzyl; and pharmaceutically acceptable salts thereof. One of ordinary skill in the art would recognize that many substituted hydrazines are suitable for use in preparing compounds of Formulae (I-IV). For example, several substituted phenyl, benzyl, and phenethyl groups are suitable for use as substituent groups Ar1, Ar2, and Ar3 with the presently disclosed compounds.

In particular embodiments, the compound of Formula (I) has the following structure:

Formula (V)

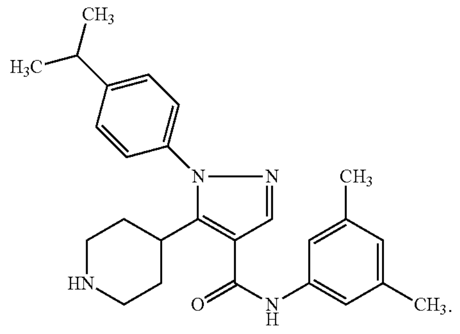

In yet other embodiments, the compound is a compound of Formula (II) and n=0; Ar1 is 4-methoxyphenyl; Ar2 is 2-ethoxylphenyl; and Ar3 is 4-methoxyphenyl. In particular embodiments, the compound has the following structure:

Formula (VI) or IPR-99

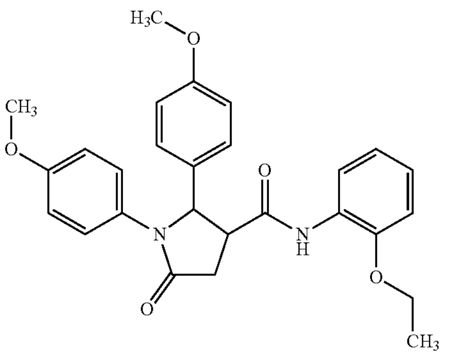

In yet other embodiments, the compound is a compound of Formula (II) and n=1; Ar1 is selected from the group consisting of benzo[d][1,3]dioxol-5-yl, 3-chloro-4-methoxyphenyl, and 4-methoxyphenyl; Ar2 is selected from the group consisting of 3,4-dimethoxyphenyl, 3-fluoro-4-methylphenyl, and 2,4-dimethoxyphenyl; and Ar3 is 4-methoxyphenyl and 4-fluorophenyl.

In particular embodiments, the compound of Formula (II) is selected from the group consisting of:

Formula (VII) or IPR-114

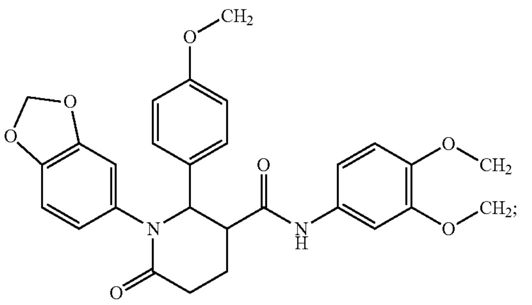

Formula (VIII) or IPR-105

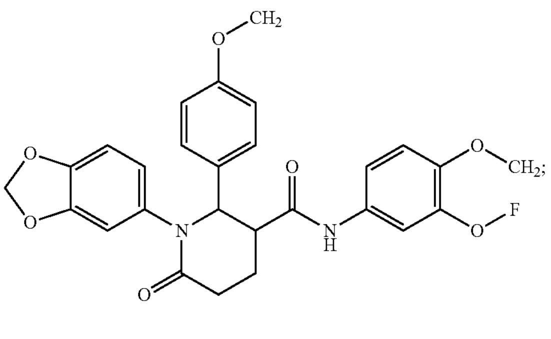

-continued

Formula (IX) or IPR-108

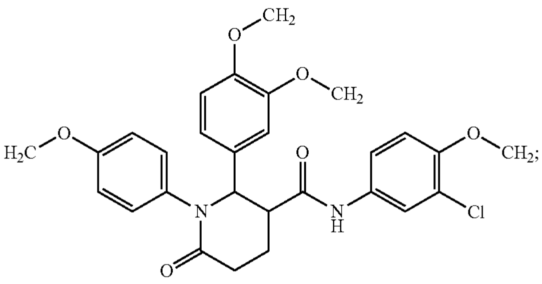

and

Formula (X)

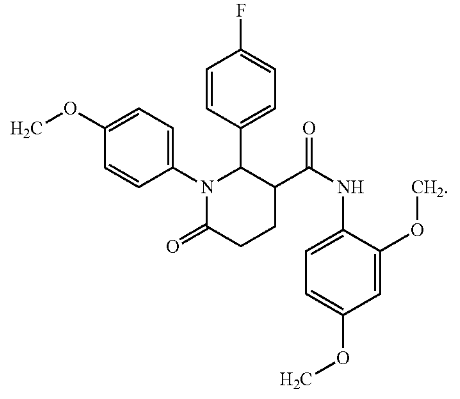

In other embodiments, the compound is a compound of Formula (III) and Ar1 is benzo[d][1,3]dioxol-5-yl; Ar2 is benzyl; and Ar3 is selected from the group consisting of benzyl and 2-methoxyphenyl.

In particular embodiments, the compound of Formula (III) is selected from the group consisting of:

Formula (XI) or IPR-22

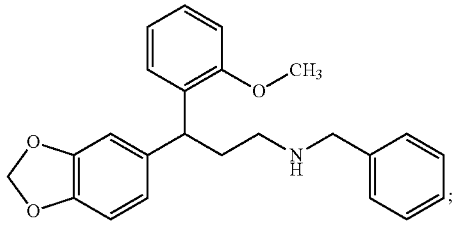

and

Formula (XII) or IPR-21

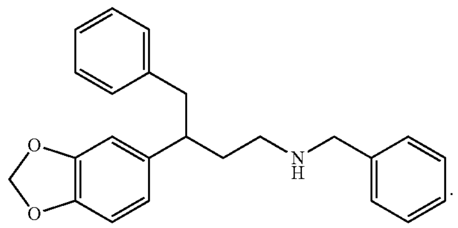

In yet other embodiments, the compound is a compound of Formula (IV) and has the following structure:

Formula (XIII) or IPR-993

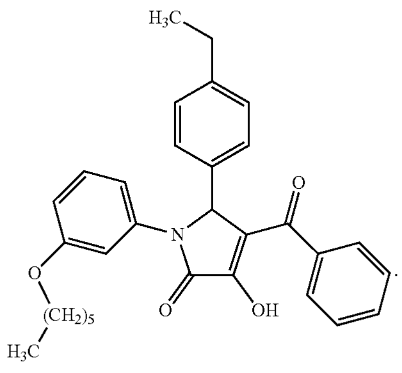

Cancer affects many different biological processes within cells and also affects processes comprising interactions between cells and in tissue. In particular embodiments, the method further comprises treating, inhibiting, delaying, or preventing cancer by inhibiting at least one cancer cell or preventing the formation of at least one cancer cell involved in one or more biological processes selected from the group consisting of cell migration, cell growth, cell adhesion, angiogenesis, cancer cell invasion, apoptosis, tumor formation, tumor progression, metastasis, degradation of the extracellular matrix, pericellular proteolysis, activation of plasminogen, changes in the levels of an extracellular protease, and changes in the levels of a VEGF receptor.

Extracellular proteases include matrix metalloproteinases (MMP), which are capable of degrading extracellular matrix proteins and are thought to play a major role in cell proliferation, migration, differentiation, angiogenesis, and apoptosis. In some embodiments, the extracellular protease comprises a matrix metalloproteinase (MMP). In particular embodiments, the MMP comprises MMP-9.

VEGF receptors are receptors for vascular endothelial growth factors (VEGF), which are signaling proteins involved in angiogenesis. In some embodiments, the VEGF receptor comprises VEGFR2. The compounds of Formulae (I-IV) are effective against cancers. In some embodiments, the cancer comprises a breast cancer. In some embodiments, the cancer comprises pancreatic cancer. Generally, the compounds are effective against any type of cancer that is involved with binding of the urokinase receptor. In yet other embodiments, the presently disclosed subject matter provides a method for inhibiting a cancer cell or preventing the formation of a cancer cell from a noncancerous cell, the method comprising contacting the cancer or noncancerous cell with a compound of Formulae (I-IV) in an amount effective to inhibit binding of the urokinase-type plasminogen activator (uPA) to the urokinase receptor (uPAR).

The inhibition or prevention of binding of uPA to uPAR affects many biological processes within a cell, between cells, within tissue, and in a subject. In some embodiments, the method further comprises inhibiting or preventing one or more biological processes selected from the group consisting of cell migration, cell growth, cell adhesion, angiogenesis, cancer cell invasion, tumor formation, tumor progression, apoptosis, metastasis, degradation of the extracellular matrix, pericellular proteolysis, activation of plasminogen, changes in the levels of an extracellular protease, and changes in the levels of a VEGF receptor. In some embodiments, the method is in vitro, in vivo, or ex vivo. The presently disclosed methods accordingly can be practiced, for example, as a research method to identify compounds or to determine the effects of compounds and concentrations of compounds, as a therapeutic method for treating a disease or disorder involving binding to the uPAR, or as a method for preventing a disease or disorder involving the uPAR.

In vitro methods may include, for example, the step of administering to at least one cell at least one compound of the presently disclosed subject matter having the ability to inhibit or prevent binding of uPA to its receptor. In some embodiments, the in vitro methods can occur in a petri dish, a test tube, an IV tube, or any other container applicable for contacting at least one compound to at least one cell. When practiced in vitro, the methods may be used for identifying parameters that are useful in in vivo treatment regimens. The in vitro methods also can include using the compound to observe the effects of disruption of binding of uPA to its receptor on cells, including observing the cells for changes in protein expression, cell morphology, or any other characteristic of interest.

In some embodiments, the compounds of the presently disclosed subject matter affect a noncancerous cell. In some embodiments, the cell affected by the compounds is a cancer cell. In some embodiments, the cancer cell comprises a breast cancer cell. In some embodiments, the cancer cell comprises a pancreatic cancer cell. uPAR has been found to have a role in cell signaling through lateral interactions with cell surface receptors. In yet other embodiments, the presently disclosed subject matter provides a method for inhibiting cell signaling involving cell surface receptors between at least two cells, the method comprising contacting at least one cell with a compound of Formulae (I-IV) in an amount effective to inhibit cell signaling.

Further, in some embodiments, the method is a method for inhibiting cell signaling in a subject, the method comprising administering to the subject a compound of Formulae (I-IV) in an amount effective to inhibit cell signaling.

In some embodiments, the methods involving the inhibition of cell signaling further comprise inhibiting uPAR and/or inhibiting MAPK phosphorylation.

In yet other embodiments, at least one of the cells involved in the cell signaling is a cancer cell. In particular embodiments, the cancer cell is a breast cancer cell or a pancreatic cancer cell.

Without wishing to be bound to any one particular theory, it is believed that the presently disclosed compounds can modulate the activity or expression of a target protein a biological pathway associated with a cancer. In particular embodiments, the presently disclosed compounds inhibit urokinase receptor, which is a cell surface GPI-anchored protein that has been widely implicated with promoting metastasis.

In any of the above-described methods, the administering of a compound of Formulae (I-IV) results in at least about a 10%, 15%, 20%, 25%, 30%, 35%, 40%, 45%, 50%, 55%, 60%, 65%, 70%, 75%, 80%, 85%, 90%, 95%, or even 100% decrease in the likelihood of developing a disease, disorder, or condition related to cancer; a condition of the subject that is secondary to a disease, disorder, condition, or therapy related to cancer compared to a control population of subjects that are not administered a compound of Formulae (I-IV).

The above-listed terms also include in vitro and ex vivo methods. For example, in certain embodiments, the presently disclosed methods are applicable to cell culture techniques wherein it is desirable to promote cancer cell death or loss of cancer cell function.

B. Pharmaceutical Compositions

The presently disclosed pharmaceutical compositions and formulations include pharmaceutical compositions of compounds of Formulae (I-IV), alone or in combination with one or more additional therapeutic agents, in admixture with a physiologically compatible carrier, which can be administered to a subject, for example, a human subject, for therapeutic or prophylactic treatment. Acceptable carriers, excipients, or stabilizers are nontoxic to recipients at the dosages and concentrations employed, and can include buffers such as phosphate, citrate, and other organic acids; antioxidants including ascorbic acid, BHA, and BHT; low molecular weight (less than about 10 residues) polypeptides; proteins, such as serum albumin, gelatin or immunoglobulins; hydrophilic polymers, such as polyvinylpyrrolidone, amino acids such as glycine, glutamine, asparagine, arginine, or lysine; monosaccharides, disaccharides, and other carbohydrates including glucose, mannose, or dextrins; chelating agents such as EDTA; sugar alcohols such as mannitol or sorbitol; salt-forming counter-ions such as sodium; and/or nonionic surfactants such as Tween, Pluronics, or PEG. Adjuvants suitable for use with the presently disclosed compositions include adjuvants known in the art including, but not limited to, incomplete Freund's adjuvant, aluminum phosphate, aluminum hydroxide, and alum.

Compositions to be used for in vivo administration must be sterile, which can be achieved by filtration through sterile filtration membranes, prior to or following lyophilization and reconstitution. Therapeutic compositions may be placed into a container having a sterile access port, for example, an intravenous solution bag or vial having a stopper pierceable by a hypodermic injection needle.

One of skill in the art will recognize that the pharmaceutical compositions include the pharmaceutically acceptable salts of the compounds described above. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include alkali or alkaline earth metal salts including, but not limited to, sodium, lithium, potassium, calcium, magnesium and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine and the like.

When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids including, but not limited to, hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids, such as acetic (acetates), propionic (propionates), isobutyric (isobutyrates), maleic (maleates), malonic, benzoic (benzoates), succinic (succinates), suberic, fumaric (fumarates), lactic (lactates), mandelic (mandelates), phthalic (phthalates), benzenesulfonic (benzosulfonates), p-tolylsulfonic, citric (citrates), tartaric (tartrates, e.g., (+)-tartrates, (−)-tartrates or mixtures thereof including racemic mixtures), methanesulfonic, and the like. Other pharmaceutically acceptable salts, include, but are not limited to, besylate, bicarbonate, bitartrate, bromide, calcium edetate, carnsylate, carbonate, edetate, edisylate, estolate, esylate, gluceptate, gluconate, glutamate, glycollylarsanilate, hexylresorcinate, hydrabamine, hydroxynaphthoate, iodide, isethionate, lactobionate, malate, mesylate, mucate, napsylate, nitrate, pamoate (embonate), pantothenate, phosphate/diphosphate, polygalacturonate, salicylate, stearate, subacetate, sulfate, tannate, and teoclate, also are included.

Also included are salts of amino acids, such as arginate and the like, and salts of organic acids, such as, glucuronic or galactunoric acids, and the like. See, for example, Berge et al.[12] Some compounds of the present disclosure can contain both basic and acidic functionalities, which allow the compounds to be converted into either base or acid addition salts.

The neutral forms of the compounds may be regenerated by contacting the salt with a base or acid and isolating the parent compound in the conventional manner.

The parent form of the compound differs from the various salt forms in certain physical properties. For example, salts tend to be more soluble in aqueous or other protonic solvents than are the corresponding free base forms.

In particular embodiments, the pharmaceutically acceptable salt of a compound of Formulae (I-IV) is selected from the group consisting of HCl, a sulfonate, a sulfate, phosphate, a malonate, a succinate, a fumarate, a maleate, a tartrate, a 3-sulfopropanoic acid salt, and a citrate.

Certain compounds of the present disclosure can exist in unsolvated forms, as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

In addition to salt forms, the present disclosure provides compounds that can be in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

C. Combination Therapies

In certain embodiments, presently disclosed subject matter also includes combination therapies. Depending on the particular disease, disorder, or condition to be treated or prevented, additional therapeutic agents, which are normally administered to treat or prevent that condition, may be administered in combination with the compounds of this disclosure. These additional agents may be administered separately, as part of a multiple dosage regimen, from the composition comprising a compound of Formulae (I-IV). Alternatively, these agents may be part of a single dosage form, mixed together with the compound of Formulae (I-IV) in a single composition.

As used herein, the term "in combination with" refers to the administration of a compound of Formulae (I-IV) with one or more therapeutic agents either simultaneously, sequentially, or a combination thereof. Therefore, a cell or a subject administered a combination of a compound of Formulae (I-IV) can receive a compound of Formulae (I-IV)

and one or more therapeutic agents at the same time (i.e., simultaneously) or at different times (i.e., sequentially, in either order, on the same day or on different days), so long as the effect of the combination of both agents is achieved in the cell or the subject. When administered sequentially, the agents can be administered within 1, 5, 10, 30, 60, 120, 180, 240 minutes or longer of one another. In other embodiments, agents administered sequentially, can be administered within 1, 5, 10, 15, 20 or more days of one another. Where the compound of Formulae (I-IV) and one or more therapeutic agents are administered simultaneously, they can be administered to the cell or administered to the subject as separate pharmaceutical compositions, each comprising either a compound of Formulae (I-IV) or one or more therapeutic agents, or they can contact the cell as a single composition or be administered to a subject as a single pharmaceutical composition comprising both agents.

When administered in combination, the effective concentration of each of the agents to elicit a particular biological response may be less than the effective concentration of each agent when administered alone, thereby allowing a reduction in the dose of one or more of the agents relative to the dose that would be needed if the agent was administered as a single agent. The effects of multiple agents may, but need not be, additive or synergistic. The agents may be administered multiple times. In such combination therapies, the therapeutic effect of the first administered compound is not diminished by the sequential, simultaneous or separate administration of the subsequent compound(s).

A compound of Formulae (I-IV) can be used in therapy in combination with one or more other compounds used to treat a disease, disorder, or condition related to cancer. For example, a compound of Formulae (I-IV) can be co-administered in combination with one or more other compounds, for example, at a ratio in the range of 1:1-1:5-5:1, 1:1-1:10-10:1, 1:1-1:25-25:1, 1:1-1:100-100:1, 1:1-1:1000-1000:1 or 1:1-1:10,000-10,000:1, and the like.

The presently disclosed compounds of Formulae (I-IV) can be optionally combined with or administered in concert with each other or other agents known to be useful in the treatment of the relevant disease, disorder, or condition. The combination therapies can involve concurrent or sequential administration, by the same or different routes, as determined to be appropriate by those of skill in the art.

The presently disclosed subject matter also includes pharmaceutical compositions and kits including combinations as described herein.

In other embodiments, the presently disclosed subject matter includes a combination therapy of administering a compound of Formulae (I-IV) in combination with surgery and/or radiation treatment, e.g., surgical and/or radiation treatment of a cancer, and the like.

In some embodiments, the administration of the presently disclosed compounds may be in conjunction with additional therapies known to those skilled in the art in the prevention or treatment of cancer, such as with radiation therapy or with cytostatic or cytotoxic agents.

Currently, standard treatment of primary tumors consists of surgical excision followed by either radiation or IV administered chemotherapy. The typical chemotherapy regime consists of either DNA alkylating agents, DNA intercalating agents, CDK inhibitors, or microtubule poisons. The chemotherapy doses used are just below the maximal tolerated dose and therefore dose limiting toxicities typically include, nausea, vomiting, diarrhea, hair loss, neutropenia and the like.

There are large numbers of antineoplastic agents available in commercial use, in clinical evaluation and in pre-clinical development, which would be selected for treatment of cancer by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents.

A first family of antineoplastic agents, which may be used in combination with presently disclosed compounds, consists of antimetabolite-type/thymidilate synthase inhibitor antineoplastic agents. Suitable antimetabolite antineoplastic agents may be selected from, but not limited to, the group consisting of 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine kinase inhibitors, Taiho UFT and uricytin.

A second family of antineoplastic agents, which may be used in combination with presently disclosed compounds, consists of alkylating-type antineoplastic agents. Suitable alkylating-type antineoplastic agents may be selected from but not limited to the group consisting of Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP(Myr)2, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsulfam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromustine, Tanabe Seiyaku TA-077, tauromustine, temozolomide, teroxirone, tetraplatin and trimelamol.

A third family of antineoplastic agents which may be used in combination with presently disclosed compounds consists of antibiotic-type antineoplastic agents. Suitable antibiotic-type antineoplastic agents may be selected from but not limited to the group consisting of Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azinomycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-AI, esperamicin-A1b, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindanycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

A fourth family of antineoplastic agents which may be used in combination with presently disclosed compounds consists of a miscellaneous family of antineoplastic agents, including tubulin interacting agents, topoisomerase II inhibitors, topoisomerase I inhibitors and hormonal agents, selected from but not limited to the group consisting of α-carotene, α-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluoron, benzotript, Ipsen-Beaufour BIM-23015, bisantrene, Bristol-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, docetaxel elliprabin, elliptinium acetate, Tsumura EPMTC, the epothilones, ergotamine, etoposide, etretinate, fenretinide, Fujisawa FR-57704, gallium nitrate, genkwadaphnin, Chugai GLA-43, Glaxo GR-63178, grifolan NMF-SN, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8δ10, American Cyanamid L-623, leukoregulin, lonidamine, Lundbeck LU-23-112, Lilly LY-186641, NCI (US) MAP, marycin, Merrel Dow MDL-27048, Medco MEDR-340, merbarone, merocyanlne derivatives, methylanilinoacridine, Molecular Genetics MGI-136, minactivin, mitonafide, mitoquidone mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, ocreotide, Ono ONO-112, oquizanocine, Akzo Org-10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin 1, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, topotecan, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides and Yamanouchi YM-534.

Alternatively, the present compounds also may be used in co-therapies with other anti-neoplastic agents, such as acemannan, aclarubicin, aldesleukin, alemtuzumab, alitretinoin, altretamine, amifostine, aminolevulinic acid, amrubicin, amsacrine, anagrelide, anastrozole, ANCER, ancestim, ARGLABIN, arsenic trioxide, BAM 002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-NI, interferon alfa-n3, interferon alfacon-1, interferon alpha, natural, interferon beta, interferon beta-1a, interferon beta-1b, interferon gamma, natural interferon gamma-1a, interferon gamma-1b, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit antithymocyte polyclonal antibody, polyethylene glycol interferon alfa-2a, porfimer sodium, raloxifene, raltitrexed, rasburicase, rhenium Re 186 etidronate, RII retinamide, rituximab, romurtide, samarium (153 Sm) lexidronam, sargramostim, sizofiran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, VIRULIZIN, zinostatin stimalamer, or zoledronic acid; abarelix; AE 941 (Aeterna), ambamustine, antisense oligonucleotide, bcl-2 (Genta), APC 8015 (Dendreon), cetuximab, decitabine, dexaminoglutethimide, diaziquone, EL 532 (Elan), EM 800 (Endorecherche), eniluracil, etanidazole, fenretinide, filgrastim SD01 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM-1-iodine 131 MAb (Techniclone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

Alternatively, the present compounds may also be used in co-therapies with VEGFR inhibitors including: N-(4-chlorophenyl)-4-(4-pyridinylmethyl)-1-phthalazinamine; 4-[4-[[[[4-chloro-3-(trifluoromethyl)phenyl]amino]carbonyl]amino]phenoxy]-N-methyl-2-pyridinecarboxamide; N-[2-(diethylamino)ethyl]-5-[(5-fluoro-1,2-dihydro-2-oxo-3H-indol-3-ylidene)methyl]-2,4-dimethyl-1H-pyrrole-3-carboxamide; 3-[(4-bromo-2,6-difluorophenyl)methoxy]-5-[[[[4-(1-pyrrolidinyl)butyl]amino]carbonyl]amino]-4-sothiazolecarboxamide; N-(4-bromo-2-fluorophenyl)-6-methoxy-7-[(1-methyl-4-piperidinyl)methoxy]-4-quinazolinamine; 3-[5,6,7,13-tetrahydro-9-[(1-methylethoxy)methyl]-5-oxo-12H-indeno[2,1-a]-pyrrolo[3,4-c]carbazol-δ-2-yl]propyl ester N,N-dimethyl-glycine; N-[5-[[[5-(1,1-dimethylethyl)-2-oxazolyl]methyl]thio]-2-thiazolyl]-4-piperidinecarboxamide; N-[3-chloro-4-[(3-fluorophenyl)methoxy]phenyl]-6-[5-[[[2-(methylsulfonyl)-ethyl]amino]methyl]-2-furanyl]-4-quinazolinamine; 4-[(4-Methyl-1-piperazinyl)methyl]-N-[4-methyl-3-[[4-(3-pyridinyl)-2-pyrimidinyl]amino]-phenyl]benzamide; N-(3-chloro-4-fluorophenyl)-7-methoxy-6-[3-(4-morpholinyl)propoxy]-4-quinazolinamine; N-(3-ethynylphenyl)-6,7-bis(2-methoxyethoxy)-4-quinazolinamine; N-(3-((((2R)-1-methyl-2-pyrrolidinyl)methyl)oxy)-5-(trifluoromethyl)phenyl)-2-((3-(1,3-oxazol-5-yl)phenyl)amino)-3-pyridinecarboxamide; 2-(((4-fluorophenyl)methyl)amino)-N-(3-((((2R)-1-methyl-2-pyrrolidinyl)methyl)oxy)-5-(trifluoromethyl)phenyl)-3-pyridinecarboxamide; N-[3-(Azetidin-3-ylmethoxy)-5-trifluoromethyl-phenyl]-2-(4-fluoro-benzylamino)-nicotinamide; 6-fluoro-N-(4-(1-methylethyl)phenyl)-2-((4-pyridinylmethyl)amino)-3-pyridinecarboxamide; 2-((4-pyridinylmethyl)amino)-N-(3-((2S)-2-pyrrolidinylmethyl)oxy)-5-(trifluoromethyl)phenyl)-3-pyridinecarboxamide; N-(3-(1,1-dimethylethyl)-1H-pyrazol-5-yl)-2-((4-pyridinylmethyl)amino)-3-pyridinecarboxamide; N-(3,3-dimethyl-2,3-dihydro-1-benzofuran-6-yl)-2-((4-pyridinylmethyl)amino)-3-pyridinecarboxamide; N-(3-((((2S)-1-methyl-2-pyrrolidinyl)methyl)oxy)-5-(trifluoromethyl)phenyl)-2-((4-pyridinylmethyl)amino)-3-pyridinecarboxamide; 2-((4-pyridinylmethyl)amino)-N-(3-((2-(1-pyrrolidinyl)ethyl)oxy)-4-(trifluoromethyl)phenyl)-3-pyridinecarboxamide; N-(4,4-dimethyl-1-oxo-1,2,3,4-tetrahydro-isoquinolin-7-yl)-2-(1H-indazol-6-ylamino)-nicotinamide; N-[4-(tert-butyl)-3-(3-piperidylpropyl)phenyl][2-(1H-indazol-6-ylamino)(3-pyridyl)]carboxamide; N-[5-(tert-butyl)isoxazol-3-yl][2-(1H-indazol-6-ylamino)(3-pyridyl)]carboxamide; and N-[4-(tert-butyl)phenyl][2-(1H-indazol-6-ylamino)(3-pyridyl)]carboxamide; N-(3,3-dimethyl-2,3-dihydro-1H-indol-6-yl)-2-((4-pyridinylmethyl)amino)-3-pyridinecarboxamide; N-(4-(pentafluoroethyl)-3-(((2S)-2-pyrrolidinylmethyl)oxy)phenyl)-2-((4-pyridinylmethyl)amino)-3-pyridinecarboxamide; N-(3-((3-azetidinylmethyl)oxy)-5-(trifluoromethyl)phenyl)-2-((4-pyridinyl-methyl)amino)-3-pyridinecarboxamide; N-(3-(4-piperidinyloxy)-5-(trifluoromethyl)phenyl)-2-((2-(3-pyridinyl)ethyl)amino)-3-pyridinecarboxamide; N-(4,4-dimethyl-1,2,3,4-tetrahydro-isoquinolin-7-yl)-2-(1H-indazol-6-ylamino)-nicotinamide; 2-(1H-indazol-6-ylamino)-N-[3-(1-methylpyrrolidin-2-ylmethoxy)-5-trifluoromethyl-phenyl]-nicotinamide; N-[1-(2-dimethylamino-acetyl)-3,3-dimethyl-2,3-dihydro-1H-indol-6-yl]-2-(1H-indazol-6-ylamino)-nicotinamide; 2-(1H-indazol-6-ylamino)-N-[3-(pyrrolidin-2-ylmethoxy)-5-trifluoromethylphenyl]-nicotinamide; N-(1-acetyl-3,3-dimethyl-2,3-dihydro-1H-indol-6-yl)-2-(1H-indazol-6-ylamino)-nicotinamide; N-(4,4-dimethyl-1-oxo-1,2,3,4-tetrahydro-isoquinolin-7-yl)-2-(1H-indazol-6-ylamino)-nicotinamide; N-[4-(tert-butyl)-3-(3-piperidylpropyl)phenyl][2-(1H-indazol-6-ylamino)(3-pyridyl)]carboxamide; N-[5-(tert-butyl)isoxazol-3-yl][2-(1H-indazol-6-ylamino)(3-pyridyl)]carboxamide; and N-[4-(tert-butyl)phenyl][2-(1H-indazol-6-ylamino)(3-pyridyl)]carboxamide.

Other compounds can be used in combination therapy.[51-75]

In some embodiments, the combination comprises a presently disclosed compound in combination with at least one anti-angiogenic agent. Agents are inclusive of, but not limited to, in vitro synthetically prepared chemical compositions, antibodies, antigen binding regions, radionuclides, and combinations and conjugates thereof. An agent can be an agonist, antagonist, allosteric modulator, toxin or, more generally, may act to inhibit or stimulate its target (e.g., receptor or enzyme activation or inhibition), and thereby promote cell death or arrest cell growth.

Exemplary anti-tumor agents include HERCEPTIN™ (trastuzumab), which may be used to treat breast cancer and other forms of cancer, and RITUXAN™ (rituximab), ZEVALIN™ (ibritumomab tiuxetan), and LYMPHOCIDE™ (epratuzumab), which may be used to treat non-Hodgkin's lymphoma and other forms of cancer, GLEEVAC™ which may be used to treat chronic myeloid leukemia and gastrointestinal stromal tumors, and BEXXAR™ (iodine 131 tositumomab) which may be used for treatment of non-Hodgkins's lymphoma.

Exemplary anti-angiogenic agents include ERBITUX™ (IMC-C225), KDR (kinase domain receptor) inhibitory agents (e.g., antibodies and antigen binding regions that specifically bind to the kinase domain receptor), anti-VEGF agents (e.g., antibodies or antigen binding regions that specifically bind VEGF, or soluble VEGF receptors or a ligand binding region thereof) such as AVASTIN™ or VEGF-TRAP™, and anti-VEGF receptor agents (e.g., antibodies or antigen binding regions that specifically bind thereto), EGFR inhibitory agents (e.g., antibodies or antigen binding regions that specifically bind thereto) such as ABX- EGF (panitumumab), IRESSA™ (gefitinib), TARCEVA™ (erlotinib), anti-Ang1 and anti-Ang2 agents (e.g., antibodies or antigen binding regions specifically binding thereto or to their receptors, e.g., Tie2/Tek), and anti-Tie2 kinase inhibitory agents (e.g., antibodies or antigen binding regions that specifically bind thereto). The pharmaceutical compositions of the present invention can also include one or more agents (e.g., antibodies, antigen binding regions, or soluble receptors) that specifically bind and inhibit the activity of growth factors, such as antagonists of hepatocyte growth factor (HGF, also known as Scatter Factor), and antibodies or antigen binding regions that specifically bind its receptor "c-met".

Other anti-angiogenic agents include Campath, IL-8, B-FGF, Tek antagonists,[76-77] anti-TWEAK agents (e.g., specifically binding antibodies or antigen binding regions, or soluble TWEAK receptor antagonists)[78], ADAM distintegrin domain to antagonize the binding of integrin to its ligands,[79] specifically binding anti-eph receptor and/or anti-ephrin antibodies or antigen binding regions,[80-85] and anti-PDGF-BB antagonists (e.g., specifically binding antibodies or antigen binding regions) as well as antibodies or antigen binding regions specifically binding to PDGF-BB ligands, and PDGFR kinase inhibitory agents (e.g., antibodies or antigen binding regions that specifically bind thereto.

Additional anti-angiogenic/anti-tumor agents include: SD-7784 (Pfizer, USA); cilengitide;[86] pegaptanib octasodium, (Gilead Sciences, USA); Alphastatin, (BioActa, UK); M-PGA;[87] ilomastat;[88] emaxanib;[89] vatalanib, (Novartis, Switzerland); 2-methoxyestradiol, (EntreMed, USA); TLC ELL-12, (Elan, Ireland); anecortave acetate, (Alcon, USA); alpha-D148 Mab, (Amgen, USA); CEP-7055, (Cephalon, USA); anti-Vn Mab, (Crucell, Netherlands) DAC:antiangiogenic, (ConjuChem, Canada); Angiocidin, (InKine Pharmaceutical, USA); KM-2550, (Kyowa Hakko, Japan); SU-0879, (Pfizer, USA); CGP-79787, (Novartis, Switzerland, EP 970070); ARGENT technology, (Ariad, USA); YIGSR-Stealth, (Johnson & Johnson, USA); fibrinogen-E fragment, (BioActa, UK); angiogenesis inhibitor, (Trigen, UK); TBC-1635, (Encysive Pharmaceuticals, USA); SC-236, (Pfizer, USA); ABT-567, (Abbott, USA); Metastatin, (EntreMed, USA); angiogenesis inhibitor, (Tripep, Sweden); maspin, (Sosei, Japan); 2-methoxyestradiol, (Oncology Sciences Corporation, USA); ER-68203-00, (IVAX, USA); Benefin, (Lane Labs, USA); Tz-93, (Tsumura, Japan); TAN-1120, (Takeda, Japan); FR-111142;[90] platelet factor 4;[91] vascular endothelial growth factor antagonist, (Borean, Denmark); cancer therapy, (University of South Carolina, USA); bevacizumab (pINN), (Genentech, USA); angiogenesis inhibitors, (SUGEN, USA); XL 784, (Exelixis, USA); XL 647, (Exelixis, USA); MAb, alpha5beta3 integrin, second generation, (Applied Molecular Evolution, USA and MedImmune, USA); gene therapy, retinopathy, (Oxford BioMedica, UK); enzastaurin hydrochloride (USAN), (Lilly, USA); CEP 7055, (Cephalon, USA and Sanofi-Synthelabo, France); BC 1, (Genoa Institute of Cancer Research, Italy); angiogenesis inhibitor, (Alchemia, Australia); VEGF antagonist, (Regeneron, USA); rBPI 21 and BPI-derived antiangiogenic, (XOMA, USA); PI 88, (Progen, Australia); cilengitide (pINN), (Merck KGaA, German; Munich Technical University, Germany, Scripps Clinic and Research Foundation, USA); cetuximab (INN), (Aventis, France); AVE 8062, (Ajinomoto, Japan); AS 1404, (Cancer Research Laboratory, New Zealand); SG 292, (Telios, USA); Endostatin, (Boston Childrens Hospital, USA); ATN 161, (Attenuon, USA); ANGIOSTATIN, (Boston Childrens Hospital, USA); 2-methoxyestradiol, (Boston Childrens Hospital, USA); ZD 6474, (AstraZeneca, UK); ZD 6126, (Angiogene Pharmaceuticals, UK); PPI 2458, (Praecis, USA); AZD 9935, (AstraZeneca, UK); AZD 2171, (AstraZeneca, UK); vatalanib (pINN), (Novartis, Switzerland and Schering A G, Germany); tissue factor pathway inhibitors, (EntreMed, USA); pegaptanib (Pinn), (Gilead Sciences, USA); xanthorrhizol, (Yonsei University, South Korea); vaccine, gene-based, VEGF-2, (Scripps Clinic and Research Foundation, USA); SPV5.2, (Supratek, Canada); SDX 103, (University of California at San Diego, USA); PX 478, (ProlX, USA); METASTATIN, (EntreMed, USA); troponin I, (Harvard University, USA); SU 6668, (SUGEN, USA); OXI 4503, (OXiGENE, USA); o-guanidines, (Dimensional Pharmaceuticals, USA); motuporamine C, (British Columbia University, Canada); CDP 791, (Celltech Group, UK); atiprimod (pINN), (GlaxoSmithKline, UK); E 7820, (Eisai, Japan); CYC 381, (Harvard University, USA); AE 941, (Aeterna, Canada); vaccine, angiogenesis, (EntreMed, USA); urokinase plasminogen activator inhibitor, (Dendreon, USA); oglufanide (pINN), (Melmotte, USA); HIF-lalfa inhibitors, (Xenova, UK); CEP 5214, (Cephalon, USA); BAY RES 2622, (Bayer, Germany); Angiocidin, (InKine, USA); A6, (Angstrom, USA); KR 31372, (Korea Research Institute of Chemical Technology, South Korea); GW 2286, (GlaxoSmithKline, UK); EHT 0101, (ExonHit, France); CP 868596, (Pfizer, USA); CP 564959, (OSI, USA); CP 547632, (Pfizer, USA); 786034, (GlaxoSmithKline, UK); KRN 633, (Kirin Brewery, Japan); drug delivery system, intraocular, 2-methoxyestradiol, (EntreMed, USA); anginex, (Maastricht University, Netherlands, and Minnesota University, USA); ABT 510, (Abbott, USA); AAL 993, (Novartis, Switzerland); VEGI, (ProteomTech, USA); tumor necrosis factor-alpha inhibitors, (National Institute on Aging, USA); SU 11248, (Pfizer, USA and SUGEN USA); ABT 518, (Abbott, USA); YH16, (Yantai Rongchang, China); S-3APG, (Boston Childrens Hospital, USA and EntreMed, USA); MAb, KDR, (ImClone Systems, USA); MAb, alpha5 beta1, (Protein Design, USA); KDR kinase inhibitor, (Celltech Group, UK, and Johnson & Johnson, USA); GFB 116, (South Florida University, USA and Yale University, USA); CS 706, (Sankyo, Japan); combretastatin A4 prodrug, (Arizona State University, USA); chondroitinase AC, (IBEX, Canada); BAY RES 2690, (Bayer, Germany); AGM 1470, (Harvard University, USA, Takeda, Japan, and TAP, USA); AG 13925, (Agouron, USA); Tetrathiomolybdate, (University of Michigan, USA); GCS 100, (Wayne State University, USA) CV 247, (Ivy Medical, UK); CKD 732, (Chong Kun Dang, South Korea); MAb, vascular endothelium growth factor, (Xenova, UK); irsogladine (INN), (Nippon Shinyaku, Japan); RG 13577, (Aventis, France); WX 360, (Wilex, Germany); squalamine (pINN), (Genaera, USA); RPI 4610, (Sirna, USA); cancer therapy, (Marinova, Australia); heparanase inhibitors, (InSight, Israel); KL 3106, (Kolon, South Korea); Honokiol, (Emory University, USA); ZK CDK, (Schering A G, Germany); ZK Angio, (Schering A G, Germany); ZK 229561, (Novartis, Switzerland, and Schering A G, Germany); XMP 300, (XOMA, USA); VGA 1102, (Taisho, Japan); VEGF receptor modulators, (Pharmacopeia, USA); VE-cadherin-2 antagonists, (ImClone Systems, USA); Vasostatin, (National Institutes of Health, USA); vaccine, Flk-1, (ImClone Systems, USA); TZ 93, (Tsumura, Japan); TumStatin, (Beth Israel Hospital, USA); truncated soluble FLT I (vascular endothelial growth factor receptor 1), (Merck & Co, USA); Tie-2 ligands, (Regeneron, USA); and, thrombospondin 1 inhibitor, (Allegheny Health, Education and Research Foundation, USA).

Alternatively, the present compounds also may be used in co-therapies with other anti-neoplastic agents, such as VEGF antagonists, other kinase inhibitors including p38 inhibitors, KDR inhibitors, EGF inhibitors and CDK inhibitors, TNF inhibitors, metallomatrix proteases inhibitors (MMP), COX-2 inhibitors including celecoxib, NSAID's, or $\alpha_v\beta_3$ inhibitors.

D. Dosage and Mode of Administration

The presently disclosed pharmaceutical compositions can be administered using a variety of methods known in the art depending on the subject and the particular disease, disorder, or condition being treated. The administering can be carried out by, for example, intravenous infusion; injection by intravenous, intraperitoneal, intracerebral, intramuscular, intraocular, intraarterial or intralesional routes; or topical application.

More particularly, as described herein, the presently disclosed compounds can be administered to a subject for therapy by any suitable route of administration, including orally, nasally, transmucosally, rectally, intravaginally, parenterally, including intramuscular, subcutaneous, intramedullary injections, as well as intrathecal, direct intraventricular, intravenous, intra-articullar, intra-sternal, intra-synovial, intra-hepatic, intralesional, intracranial, intraperitoneal, intranasal, or intraocular injections, intracisternally, topically, as by powders, ointments or drops, including buccally and sublingually, transdermally, through an inhalation spray, or other modes of delivery known in the art.

For intracerebral use, the compounds can be administered continuously by infusion into the fluid reservoirs of the CNS, although bolus injection may be acceptable. The presently disclosed compounds can be administered into the ventricles of the brain or otherwise introduced into the CNS or spinal fluid. Administration can be performed by use of an indwelling catheter and a continuous administration means such as a pump, or it can be administered by implantation, e.g., intracerebral implantation of a sustained-release vehicle. More specifically, the presently disclosed compounds can be injected through chronically implanted cannulas or chronically infused with the help of osmotic minipumps. Subcutaneous pumps are available that deliver proteins through a small tubing to the cerebral ventricles. Highly sophisticated pumps can be refilled through the skin and their delivery rate can be set without surgical intervention.

The presently disclosed pharmaceutical compositions can be manufactured in a manner known in the art, e.g., by means of conventional mixing, dissolving, granulating, dragee-making, levitating, emulsifying, encapsulating, entrapping or lyophilizing processes.

More particularly, pharmaceutical compositions for oral use can be obtained through combination of active compounds with a solid excipient, optionally grinding a resulting mixture, and processing the mixture of granules, after adding suitable auxiliaries, if desired, to obtain tablets or dragee cores. Suitable excipients include, but are not limited to, carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethyl cellulose; and gums including arabic and tragacanth; and proteins, such as gelatin and collagen; and polyvinylpyrrolidone (PVP:povidone). If desired, disintegrating or solubilizing agents, such as cross-linked polyvinyl pyrrolidone, agar, alginic acid, or a salt thereof, such as sodium alginate, also can be added to the compositions.

Dragee cores are provided with suitable coatings, such as concentrated sugar solutions, which also can contain gum arabic, talc, polyvinylpyrrolidone, carbopol gel, polyethylene glycol (PEG), and/or titanium dioxide, lacquer solutions, and suitable organic solvents or solvent mixtures. Dyestuffs or pigments can be added to the tablets or dragee coatings for product identification or to characterize the quantity of active compound, e.g., dosage, or different combinations of active compound doses.

Pharmaceutical compositions suitable for oral administration include push-fit capsules made of gelatin, as well as soft, sealed capsules made of gelatin and a coating, e.g., a plasticizer, such as glycerol or sorbitol. The push-fit capsules can contain active ingredients admixed with a filler or binder, such as lactose or starches, lubricants, such as talc or magnesium stearate, and, optionally, stabilizers. In soft capsules, the active compounds can be dissolved or suspended in suitable liquids, such as fatty oils, liquid paraffin, or liquid polyethylene glycols (PEGs), with or without stabilizers. Stabilizers can be added as warranted.

In some embodiments, the presently disclosed pharmaceutical compositions can be administered by rechargeable or biodegradable devices. For example, a variety of slow-release polymeric devices have been developed and tested in vivo for the controlled delivery of drugs, including proteinacious biopharmaceuticals. Suitable examples of sustained release preparations include semipermeable polymer matrices in the form of shaped articles, e.g., films or microcapsules. Sustained release matrices include polyesters, hydrogels, polylactides,[92,93] copolymers of L-glutamic acid and gamma ethyl-L-glutamate,[13] poly(2-hydroxyethyl-methacrylate),[14,15] ethylene vinyl acetate[14,15] or poly-D-(−)-3-hydroxybutyric acid.[47] Sustained release compositions also include liposomally entrapped compounds, which can be prepared by methods known per se.[16,17,48,49,50] Ordinarily, the liposomes are of the small (about 200-800 Angstroms) unilamelar type in which the lipid content is greater than about 30 mol % cholesterol, the selected proportion being adjusted for the optimal therapy. Such materials can comprise an implant, for example, for sustained release of the presently disclosed compounds, which, in some embodiments, can be implanted at a particular, pre-determined target site.

Pharmaceutical compositions for parenteral administration include aqueous solutions of active compounds. For injection, the presently disclosed pharmaceutical compositions can be formulated in aqueous solutions, for example, in some embodiments, in physiologically compatible buffers, such as Hank's solution, Ringer' solution, or physiologically buffered saline. Aqueous injection suspensions can contain substances that increase the viscosity of the suspension, such as sodium carboxymethyl cellulose, sorbitol, or dextran. Additionally, suspensions of the active compounds or vehicles include fatty oils, such as sesame oil, or synthetic fatty acid esters, such as ethyl oleate or triglycerides, or liposomes. Optionally, the suspension also can contain suitable stabilizers or agents that increase the solubility of the compounds to allow for the preparation of highly concentrated solutions.

For nasal or transmucosal administration generally, penetrants appropriate to the particular barrier to be permeated are used in the formulation. Such penetrants are generally known in the art.

For inhalation delivery, the agents of the disclosure also can be formulated by methods known to those of skill in the art, and may include, for example, but not limited to, examples of solubilizing, diluting, or dispersing substances such as, saline, preservatives, such as benzyl alcohol, absorption promoters, and fluorocarbons. Additional ingredients can be added to compositions for topical administration, as long as such ingredients are pharmaceutically acceptable and not deleterious to the epithelial cells or their function. Further, such additional ingredients should not adversely affect the epithelial penetration efficiency of the composition, and should not cause deterioration in the stability of the composition. For example, fragrances, opacifiers, antioxidants, gelling agents, stabilizers, surfactants, emollients, coloring agents, preservatives, buffering agents, and the like can be present. The pH of the presently disclosed topical composition can be adjusted to a physiologically acceptable range of from about 6.0 to about 9.0 by adding buffering agents thereto such that the composition is physiologically compatible with a subject's skin.

In other embodiments, the pharmaceutical composition can be a lyophilized powder, optionally including additives, such as 1 mM-50 mM histidine, 0.1%-2% sucrose, 2%-7% mannitol at a pH range of 4.5 to 5.5 that is combined with buffer prior to use.

The presently disclosed subject matter also includes the use of a compound of Formulae (I-IV) in the manufacture of a medicament for treating cancer. Regardless of the route of administration selected, the presently disclosed compounds, which may be used in a suitable hydrated form, and/or the pharmaceutical compositions are formulated into pharmaceutically acceptable dosage forms such as described below or by other conventional methods known to those of skill in the art.

Actual dosage levels of the active ingredients in the presently disclosed pharmaceutical compositions can be varied so as to obtain an amount of the active ingredient that is effective to achieve the desired therapeutic response for a particular subject, composition, route of administration, and disease, disorder, or condition without being toxic to the subject. The selected dosage level will depend on a variety of factors including the activity of the particular compound employed, or salt thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of Formulae (I-IV) employed in the pharmaceutical composition at levels lower than that required to achieve the desired therapeutic effect and gradually increase the dosage until the desired effect is achieved. Accordingly, the dosage range for administration will be adjusted by the physician as necessary. It will be appreciated that an amount of a compound required for achieving the desired biological response, e.g., anti-cancer activity, may be different from the amount of compound effective for another purpose.

In general, a suitable daily dose of a compound of Formulae (I-IV) will be that amount of the compound that is the lowest dose effective to produce a therapeutic effect. Such an effective dose will generally depend upon the factors described above. Generally, doses of the compounds of Formulae (I-IV) will range from about 15 0.0001 to about 1000 mg per kilogram of body weight of the subject per day. In certain embodiments, the dosage is between about 1 μg/kg and about 500 mg/kg, more preferably between about 0.01 mg/kg and about 50 mg/kg. For example, in certain embodiments, a dose can be about 1, 5, 10, 15, 20, or 40 mg/kg/day.

If desired, the effective daily dose of the active compound can be administered as two, three, four, five, six or more sub-doses administered separately at appropriate intervals throughout the day, optionally, in unit dosage forms.

E. Kits or Pharmaceutical Systems

The presently disclosed compounds and compositions can be assembled into kits or pharmaceutical systems for use in treating or preventing diseases, disorders, or conditions related to cancer. In some embodiments, the presently disclosed kits or pharmaceutical systems include a compound of Formulae (I-IV), or pharmaceutically acceptable salts thereof. In particular embodiments, the compounds of Formulae (I-IV), or a pharmaceutically acceptable salt thereof, are in unit dosage form. In further embodiments, the compound of Formulae (I-IV), or a pharmaceutically acceptable salt, can be present together with a pharmaceutically acceptable solvent, carrier, excipient, or the like, as described herein.

In some embodiments, the presently disclosed kits comprise one or more containers, including, but not limited to a vial, tube, ampule, bottle and the like, for containing the compound. The one or more containers also can be carried within a suitable carrier, such as a box, carton, tube or the like. Such containers can be made of plastic, glass, laminated paper, metal foil, or other materials suitable for holding medicaments.

In some embodiments, the container can hold a composition that is by itself or when combined with another composition effective for treating or preventing the condition and may have a sterile access port (for example the container may be an intravenous solution bag or a vial having a stopper pierceable by a hypodermic injection needle). Alternatively, or additionally, the article of manufacture may further include a second (or third) container including a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The presently disclosed kits or pharmaceutical systems also can include associated instructions for using the compounds for treating or preventing a disease, disorder, or condition related to cancer. In some embodiments, the instructions include one or more of the following: a description of the active compound; a dosage schedule and administration for treating or preventing a disease, disorder, or condition related to cancer; precautions; warnings; indications; counter-indications; overdosage information; adverse reactions; animal pharmacology; clinical studies; and references. The instructions can be printed directly on a container (when present), as a label applied to the container, as a separate sheet, pamphlet, card, or folder supplied in or with the container.

F. Chemical Definitions

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

While the following terms in relation to compounds of Formulae (I-IV) are believed to be well understood by one of ordinary skill in the art, the following definitions are set forth to facilitate explanation of the presently disclosed subject matter. These definitions are intended to supplement and illustrate, not preclude, the definitions that would be apparent to one of ordinary skill in the art upon review of the present disclosure.

The terms substituted, whether preceded by the term "optionally" or not, and substituent, as used herein, refer to the ability, as appreciated by one skilled in this art, to change one functional group for another functional group provided that the valency of all atoms is maintained. When more than one position in any given structure may be substituted with more than one substituent selected from a specified group, the substituent may be either the same or different at every position. The substituents also may be further substituted (e.g., an aryl group substituent may have another substituent off it, such as another aryl group, which is further substituted, for example, with fluorine at one or more positions).

Where substituent groups or linking groups are specified by their conventional chemical formulae, written from left to right, they equally encompass the chemically identical substituents that would result from writing the structure from right to left, e.g., $—CH_2O—$ is equivalent to $—OCH_2—$; —C(═O)O— is equivalent to —OC(═O)—; —OC(═O)NR— is equivalent to —NRC(═O)O—, and the like.

When the term "independently selected" is used, the substituents being referred to (e.g., R groups, such as groups $R_1$, $R_2$, and the like, or variables, such as "m" and "n"), can be identical or different. For example, both $R_1$ and $R_2$ can be substituted alkyls, or $R_1$ can be hydrogen and $R_2$ can be a substituted alkyl, and the like.

The terms "a," "an," or "a(n)," when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

A named "R" or group will generally have the structure that is recognized in the art as corresponding to a group having that name, unless specified otherwise herein. For the purposes of illustration, certain representative "R" groups as set forth above are defined below.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term hydrocarbon, as used herein, refers to any chemical group comprising hydrogen and carbon. The hydrocarbon may be substituted or unsubstituted. As would be known to one skilled in this art, all valencies must be satisfied in making any substitutions. The hydrocarbon may be unsaturated, saturated, branched, unbranched, cyclic, polycyclic, or heterocyclic. Illustrative hydrocarbons are further defined herein below and include, for example, methyl, ethyl, n-propyl, iso-propyl, cyclopropyl, allyl, vinyl, n-butyl, tert-butyl, ethynyl, cyclohexyl, methoxy, diethylamino, and the like.

The term "alkyl," by itself or as part of another substituent, means, unless otherwise stated, a straight (i.e., unbranched) or branched chain, acyclic or cyclic hydrocarbon group, or combination thereof, which may be fully saturated, mono- or polyunsaturated and can include di- and multivalent groups, having the number of carbon atoms designated (i.e., $C_1$-$C_{10}$ means one to ten carbons). In particular embodiments, the term "alkyl" refers to $C_{1-20}$ inclusive, linear (i.e., "straight-chain"), branched, or cyclic, saturated or at least partially and in some cases fully unsaturated (i.e., alkenyl and alkynyl)hydrocarbon radicals derived from a hydrocarbon moiety containing between one and twenty carbon atoms by removal of a single hydrogen atom.

Representative saturated hydrocarbon groups include, but are not limited to, methyl, ethyl, n-propyl, isopropyl, n-butyl, isobutyl, sec-butyl, tert-butyl, n-pentyl, sec-pentyl, isopentyl, neopentyl, n-hexyl, sec-hexyl, n-heptyl, n-octyl, n-decyl, n-undecyl, dodecyl, cyclohexyl, (cyclohexyl)methyl, cyclopropylmethyl, and homologs and isomers thereof.

"Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "heteroalkyl," by itself or in combination with another term, means, unless otherwise stated, a stable straight or branched chain, or cyclic hydrocarbon group, or combinations thereof, consisting of at least one carbon atoms and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, $—CH_2—CH_2—O—CH_3$, $—CH_2—CH_2—NH—CH_3$, $—CH_2—CH_2—N(CH_3)—CH_3$, $—CH_2—S—CH_2—CH_3$, $—CH_2—CH_{25}—S(O)—CH_3$, $—CH_2—CH_2—S(O)_2—$ $CH_3$, —CH═CH—O—$CH_3$, —Si$(CH_3)_3$, —$CH_2$—CH═N—$OCH_3$, —CH═CH—N$(CH_3)$—$CH_3$, —O—$CH_3$, —O—$CH_2$—$CH_3$, and —CN. Up to two or three heteroatoms may be consecutive, such as, for example, —$CH_2$—NH—$OCH_3$ and —$CH_2$—O—Si$(CH_3)_3$.

As described above, heteroalkyl groups, as used herein, include those groups that are attached to the remainder of the molecule through a heteroatom, such as —C(O)R', —C(O)NR', —NR'R", —OR', —SR, and/or —$SO_2$R'. Where "heteroalkyl" is recited, followed by recitations of specific heteroalkyl groups, such as —NR'R or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl, and fused ring systems, such as dihydro- and tetrahydronaphthalene, and the like.

The term "cycloalkylalkyl," as used herein, refers to a cycloalkyl group as defined hereinabove, which is attached to the parent molecular moiety through an alkyl group, also as defined above. Examples of cycloalkylalkyl groups include cyclopropylmethyl and cyclopentylethyl.

The terms "cycloheteroalkyl" or "heterocycloalkyl" refer to a non-aromatic ring system, unsaturated or partially unsaturated ring system, such as a 3- to 10-member substituted or unsubstituted cycloalkyl ring system, including one or more heteroatoms, which can be the same or different, and are selected from the group consisting of nitrogen (N), oxygen (O), sulfur (S), phosphorus (P), and silicon (Si), and optionally can include one or more double bonds.

The cycloheteroalkyl ring can be optionally fused to or otherwise attached to other cycloheteroalkyl rings and/or non-aromatic or aromatic hydrocarbon rings.

Heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocylic refers to a non-aromatic 5-, 6-, or 7-membered ring or a polycyclic group wherein at least one ring atom is a heteroatom selected from O, S, and N (wherein the nitrogen and sulfur heteroatoms may be optionally oxidized), including, but not limited to, a bi- or tri-cyclic group, comprising fused six-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Representative cycloheteroalkyl ring systems include, but are not limited to pyrrolidinyl, pyrrolinyl, imidazolidinyl, imidazolinyl, pyrazolidinyl, pyrazolinyl, piperidyl, piperazinyl, indolinyl, quinuclidinyl, morpholinyl, thiomorpholinyl, thiadiazinanyl, tetrahydrofuranyl, and the like. Cycloheteroalkyl rings also can be fused to an aromatic ring, for example to form a fused cycloheteroalkyl/aryl fused ring system, such as a benzo[d][1,3]dioxole system.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "cycloalkylene" and "heterocycloalkylene" refer to the divalent derivatives of cycloalkyl and heterocycloalkyl, respectively.

An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Alkyl groups which are limited to hydrocarbon groups are termed "homoalkyl."

More particularly, the term "alkenyl" as used herein refers to a monovalent group derived from a C1-20 inclusive straight or branched hydrocarbon moiety having at least one carbon-carbon double bond by the removal of a single hydrogen atom. Alkenyl groups include, for example, ethenyl (i.e., vinyl), propenyl, butenyl, 1-methyl-2-buten-1-yl, pentenyl, hexenyl, octenyl, and butadienyl.

The term "cycloalkenyl" as used herein refers to a cyclic hydrocarbon containing at least one carbon-carbon double bond. Examples of cycloalkenyl groups include cyclopropenyl, cyclobutenyl, cyclopentenyl, cyclopentadiene, cyclohexenyl, 1,3-cyclohexadiene, cycloheptenyl, cycloheptatrienyl, and cyclooctenyl.

The term "alkynyl" as used herein refers to a monovalent group derived from a straight or branched C1-20 hydrocarbon of a designed number of carbon atoms containing at least one carbon-carbon triple bond. Examples of "alkynyl" include ethynyl, 2-propynyl(propargyl), 1-propynyl, pentynyl, hexynyl, heptynyl, and allenyl groups, and the like.

The term "alkylene" by itself or a part of another substituent refers to a straight or branched bivalent aliphatic hydrocarbon group derived from an alkyl group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—$CH_2$—); ethylene (—$CH_2$—$CH_2$—); propylene (—$(CH_2)_3$—); cyclohexylene (—$C_6H_{10}$—); —CH═CH—CH═CH—; —CH═CH—$CH_2$—; —$CH_2CH_2CH_2CH_2$—, $—CH_2CH{=}CHCH_2—$, $—CH_2CsCCH_2—$, $—CH_2CH_2CH(CH_2CH_2CH_3)CH_2—$, $—(CH_2)_q—N(R)—(CH_2)_r—$, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl ($—O—CH_2—O—$); and ethylenedioxyl ($—O—(CH_2)_2—O—$). An alkylene group can have about 2 to about 3 carbon atoms and can further have 6-20 carbons. Typically, an alkyl (or alkylene) group will have from 1 to 24 carbon atoms, with those groups having 10 or fewer carbon atoms being some embodiments of the present disclosure. A "lower alkyl" or "lower alkylene" is a shorter chain alkyl or alkylene group, generally having eight or fewer carbon atoms.

The term "heteroalkylene" by itself or as part of another substituent means a divalent group derived from heteroalkyl, as exemplified, but not limited by, $—CH_2—CH_2—S—CH_2—CH_2—$ and $—CH_2—S—CH_2—CH_2—NH—CH_2—$. For heteroalkylene groups, heteroatoms can also occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC(O)—.

The term "aryl" means, unless otherwise stated, an aromatic hydrocarbon substituent that can be a single ring or multiple rings (such as from 1 to 3 rings), which are fused together or linked covalently. The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and quinolyl. Substituents for each of above noted aryl and heteroaryl ring systems are selected from the group of acceptable substituents described below. The terms "arylene" and "heteroarylene" refer to the divalent forms of aryl and heteroaryl, respectively.

For brevity, the term "aryl" when used in combination with other terms (e.g., aryloxo, arylthioxo, arylalkyl) includes both aryl and heteroaryl rings as defined above. Thus, the terms "arylalkyl" and "heteroarylalkyl" are meant to include those groups in which an aryl or heteroaryl group is attached to an alkyl group (e.g., benzyl, phenethyl, pyridylmethyl, furylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). However, the term "haloaryl," as used herein is meant to cover only aryls substituted with one or more halogens.

Where a heteroalkyl, heterocycloalkyl, or heteroaryl includes a specific number of members (e.g. "3 to 7 membered"), the term "member" refers to a carbon or heteroatom.

Further, a structure represented generally by the formula:

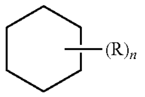

as used herein refers to a ring structure, for example, but not limited to a 3-carbon, a 4-carbon, a 5-carbon, a 6-carbon, a 7-carbon, and the like, aliphatic and/or aromatic cyclic compound, including a saturated ring structure, a partially saturated ring structure, and an unsaturated ring structure, comprising a substituent R group, wherein the R group can be present or absent, and when present, one or more R groups can each be substituted on one or more available carbon atoms of the ring structure. The presence or absence of the R group and number of R groups is determined by the value of the variable "n," which is an integer generally having a value ranging from 0 to the number of carbon atoms on the ring available for substitution. Each R group, if more than one, is substituted on an available carbon of the ring structure rather than on another R group. For example, the structure above where n is 0 to 2 would comprise compound groups including, but not limited to:

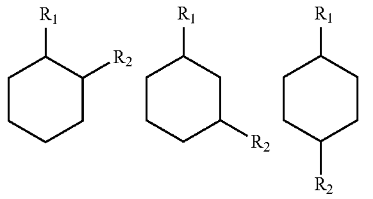

and the like.

A dashed line representing a bond in a cyclic ring structure indicates that the bond can be either present or absent in the ring. That is, a dashed line representing a bond in a cyclic ring structure indicates that the ring structure is selected from the group consisting of a saturated ring structure, a partially saturated ring structure, and an unsaturated ring structure.

The symbol (  ) denotes the point of attachment of a moiety to the remainder of the molecule.

When a named atom of an aromatic ring or a heterocyclic aromatic ring is defined as being "absent," the named atom is replaced by a direct bond.

Each of above terms (e.g., "alkyl," "heteroalkyl," "cycloalkyl, and "heterocycloalkyl", "aryl," "heteroaryl," "phosphonate," and "sulfonate" as well as their divalent derivatives) are meant to include both substituted and unsubstituted forms of the indicated group. Optional substituents for each type of group are provided below.

Substituents for alkyl, heteroalkyl, cycloalkyl, heterocycloalkyl monovalent and divalent derivative groups (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R', —C(O)R', $—CO_2R'$, —C(O)NR'R", —OC(O)NR'R", —NR"C(O)R', —NR'—C(O)NR"R'", —NR"C(O)OR', —NR—C(NR'R")=NR'", —S(O)R', $—S(O)_2R'$, $—S(O)_2NR'R"$, $—NRSO_2R'$, —CN and $—NO_2$ in a number ranging from zero to (2 m'+1), where m' is the total number of carbon atoms in such groups. R', R", R"' and R"" each may independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. As used herein, an "alkoxy" group is an alkyl attached to the remainder of the molecule through a divalent oxygen. When a compound of the disclosure includes more than one R group, for example, each of the R groups is independently selected as are each R', R", R"' and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., $—CF_3$ and $—CH_2CF_3$) and acyl (e.g., $—C(O)CH_3$, $—C(O)CF_3$, $—C(O)CH_2OCH_3$, and the like).

Similar to the substituents described for alkyl groups above, exemplary substituents for aryl and heteroaryl groups (as well as their divalent derivatives) are varied and are selected from, for example: halogen, —OR', —NR'R", —SR', -halogen, —SiR'R"R"', —OC(O)R', —C(O)R', $—CO_2R'$, —C(O)NR'R", —OC(O)NR'R", —NR"C(O)R', —NR'—C(O)NR"R"', —NR"C(O)OR', —NR—C(NR'R"R"')=NR"", —NR—C(NR'R")=NR"'—S(O)R', $—S(O)_2R'$, $—S(O)_2NR'R"$, $—NRSO_2R'$, —CN and $—NO_2$, —R', $—N_3$, $—CH(Ph)_2$, fluoro($C_1$-$C_4$)alkoxo, and fluoro($C_1$-$C_4$)alkyl, in a number ranging from zero to the total number of open valences on aromatic ring system; and where R', R", R"' and R"" may be independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the disclosure includes more than one R group, for example, each of the R groups is independently selected as are each R', R", R"' and R"" groups when more than one of these groups is present.

Two of the substituents on adjacent atoms of aryl or heteroaryl ring may optionally form a ring of the formula -T-C(O)— $(CRR')_q$—U—, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula $-A-(CH_2)_r—B—$, wherein A and B are independently —CRR'—, —O—, —NR—, —S—, —S(O)—, $—S(O)_2—$, $—S(O)_2NR'—$ or a single bond, and r is an integer of from 1 to 4.

One of the single bonds of the new ring so formed may optionally be replaced with a double bond. Alternatively, two of the substituents on adjacent atoms of aryl or heteroaryl ring may optionally be replaced with a substituent of the formula $—(CRR')_s—X'—(C"R"')_d—$, where s and d are independently integers of from 0 to 3, and X' is —O—, —NR'—, —S—, —S(O)—, $—S(O)_2—$, or $—S(O)_2NR'—$. The substituents R, R', R" and R"' may be independently selected from hydrogen, substituted or unsubstituted alkyl, substituted or unsubstituted cycloalkyl, substituted or unsubstituted heterocycloalkyl, substituted or unsubstituted aryl, and substituted or As used herein, the term "acyl" refers to an organic acid group wherein the —OH of the carboxyl group has been replaced with another substituent and has the general formula RC(=O)—, wherein R is an alkyl, alkenyl, alkynyl, aryl, carbocylic, heterocyclic, or aromatic heterocyclic group as defined herein. As such, the term "acyl" specifically includes arylacyl groups, such as an acetylfuran and a phenacyl group. Specific examples of acyl groups include acetyl and benzoyl.

The terms "alkoxyl" or "alkoxy" are used interchangeably herein and refer to a saturated (i.e., alkyl-O—) or unsaturated (i.e., alkenyl-O— and alkynyl-O—) group attached to the parent molecular moiety through an oxygen atom, wherein the terms "alkyl," "alkenyl," and "alkynyl" are as previously described and can include C1-20 inclusive, linear, branched, or cyclic, saturated or unsaturated oxo-hydrocarbon chains, including, for example, methoxyl, ethoxyl, propoxyl, isopropoxyl, n-butoxyl, sec-butoxyl, t-butoxyl, and n-pentoxyl, neopentoxyl, n-hexoxyl, and the like.

The term "alkoxyalkyl" as used herein refers to an alkyl-O-alkyl ether, for example, a methoxyethyl or an ethoxymethyl group.

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl. "Alkoxycarbonyl" refers to an alkyl-O—CO— group. Exemplary alkoxycarbonyl groups include methoxycarbonyl, ethoxycarbonyl, butyloxycarbonyl, and t-butyloxycarbonyl.

"Aryloxycarbonyl" refers to an aryl-O—CO— group. Exemplary aryloxycarbonyl groups include phenoxy- and naphthoxy-carbonyl. "Aralkoxycarbonyl" refers to an aralkyl-O—CO— group. An exemplary aralkoxycarbonyl group is benzyloxycarbonyl.

"Carbamoyl" refers to an amide group of the formula $—CONH_2$.

"Alkylcarbamoyl" refers to a R'RN—CO— group wherein one of R and R' is hydrogen and the other of R and R' is alkyl and/or substituted alkyl as previously described.

"Dialkylcarbamoyl" refers to a R'RN—CO— group wherein each of R and R' is independently alkyl and/or substituted alkyl as previously described.

The term carbonyldioxyl, as used herein, refers to a carbonate group of the formula —O—CO—OR.

"Acyloxyl" refers to an acyl-O— group wherein acyl is as previously described. The term "amino" refers to the —NH2 group and also refers to a nitrogen containing group as is known in the art derived from ammonia by the replacement of one or more hydrogen radicals by organic radicals. For example, the terms "acylamino" and "alkylamino" refer to specific N-substituted organic radicals with acyl and alkyl substituent groups respectively.

An "aminoalkyl" as used herein refers to an amino group covalently bound to an alkylene linker. More particularly, the terms alkylamino, dialkylamino, and trialkylamino as used herein refer to one, two, or three, respectively, alkyl groups, as previously defined, attached to the parent molecular moiety through a nitrogen atom. The term alkylamino refers to a group having the structure —NHR' wherein R' is an alkyl group, as previously defined; whereas the term dialkylamino refers to a group having the structure —NR'R", wherein R' and R" are each independently selected from the group consisting of alkyl groups. The term trialkylamino refers to a group having the structure —NR'R"R'", wherein R', R", and R'" are each independently selected from the group consisting of alkyl groups. Additionally, R', R", and/or R'" taken together may optionally be $—(CH_2)_k—$ where k is an integer from 2 to 6. Examples include, but are not limited to, methylamino, dimethylamino, ethylamino, diethylamino, diethylaminocarbonyl, methylethylamino, iso-propylamino, piperidino, trimethylamino, and propylamino.

The amino group is —NR'R", wherein R' and R" are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

The terms alkylthioether and thioalkoxyl refer to a saturated (i.e., alkyl-S—) or unsaturated (i.e., alkenyl-S— and alkynyl-S—) group attached to the parent molecular moiety through a sulfur atom. Examples of thioalkoxyl moieties include, but are not limited to, methylthio, ethylthio, propylthio, isopropylthio, n-butylthio, and the like.

“Acylamino” refers to an acyl-NH— group wherein acyl is as previously described.

“Aroylamino” refers to an aroyl-NH— group wherein aroyl is as previously described.

The term “carbonyl” refers to the —(C═O)— group.

The term “carboxyl” refers to the —COOH group. Such groups also are referred to herein as a “carboxylic acid” moiety.

The terms “halo,” “halide,” or “halogen” as used herein refer to fluoro, chloro, bromo, and iodo groups. Additionally, terms such as “haloalkyl,” are meant to include monohaloalkyl and polyhaloalkyl. For example, the term “halo($C_1$-$C_4$)alkyl” is mean to include, but not be limited to, trifluoromethyl, 2,2,2-trifluoroethyl, 4-chlorobutyl, 3-bromopropyl, and the like.

The term “hydroxyl” refers to the —OH group.

The term “hydroxyalkyl” refers to an alkyl group substituted with an —OH group.

The term “mercapto” refers to the —SH group.

The term “oxo” as used herein means an oxygen atom that is double bonded to a carbon atom or to another element.

The term “nitro” refers to the $—NO_2$ group.

The term “thio” refers to a compound described previously herein wherein a carbon or oxygen atom is replaced by a sulfur atom.

The term “sulfate” refers to the $—SO_4$ group.

The term “thiohydroxyl” or “thiol”, as used herein, refers to a group of the formula —SH.

The term “ureido” refers to a urea group of the formula —NH—CO—NH2. Unless otherwise explicitly defined, a “substituent group,” as used herein, includes a functional group selected from one or more of the following moieties, which are defined herein: (A) —OH, —NH2, —SH, —CN, $—CF_3$, $—NO_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from: (i) oxo, —OH, $—NH_2$, —SH, —CN, $—CF_3$, $—NO_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from: (a) oxo, —OH, $—NH_2$, —SH, —CN, $—CF_3$, $—NO_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from oxo, —OH, $—NH_2$, —SH, —CN, $—CF_3$, $—NO_2$, halogen, unsubstituted alkyl, unsubstituted heteroalkyl, unsubstituted cycloalkyl, unsubstituted heterocycloalkyl, unsubstituted aryl, and unsubstituted heteroaryl.

A “lower substituent” or “lower substituent group,” as used herein means a group selected from all of the substituents described hereinabove for a “substituent group,” wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted C5-C7 cycloalkyl, and each substituted or unsubstituted heterocycloalkyl is a substituted or unsubstituted 5 to 7 membered heterocycloalkyl.

A “size-limited substituent” or “size-limited substituent group,” as used herein means a group selected from all of the substituents described above for a “substituent group,” wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, and each substituted or unsubstituted heterocycloalkyl is a substituted or unsubstituted 4 to 8 membered heterocycloalkyl.

Throughout the specification and claims, a given chemical formula or name shall encompass all tautomers, congeners, and optical- and stereoisomers, as well as racemic mixtures where such isomers and mixtures exist.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those which are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefenic bonds or other centers of geometric asymmetry, and unless specified otherwise, it is intended that the compounds include both E and Z geometric isomers.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

It will be apparent to one skilled in the art that certain compounds of this disclosure may exist in tautomeric forms, all such tautomeric forms of the compounds being within the scope of the disclosure. The term "tautomer," as used herein, refers to one of two or more structural isomers which exist in equilibrium and which are readily converted from one isomeric form to another.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by 13C- or I4C-enriched carbon are within the scope of this disclosure.

The compounds of the present disclosure may also contain unnatural proportions of atomic isotopes at one or more of atoms that constitute such compounds. For example, the compounds may be radiolabeled with radioactive isotopes, such as for example tritium ($^{3}H$), iodine-125 ($^{125}I$) or carbon-14 ($^{14}C$). All isotopic variations of the compounds of the present disclosure, whether radioactive or not, are encompassed within the scope of the present disclosure.

The term "protecting group" refers to chemical moieties that block some or all reactive moieties of a compound and prevent such moieties from participating in chemical reactions until the protective group is removed, for example, those moieties listed and described in Greene et al.[18] It may be advantageous, where different protecting groups are employed, that each (different) protective group be removable by a different means. Protective groups that are cleaved under totally disparate reaction conditions allow differential removal of such protecting groups. For example, protective groups can be removed by acid, base, and hydrogenolysis. Groups such as trityl, dimethoxytrityl, acetal and tert-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, without limitation, methyl, ethyl, and acetyl in the presence of amines blocked with acid labile groups such as tert-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be blocked with oxidatively-removable protective groups such as 2,4-dimethoxybenzyl, while co-existing amino groups may be blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a palladium(O)-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typical blocking/protecting groups include, but are not limited to the following moieties:

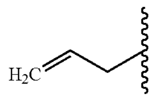
allyl

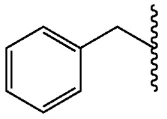
Bn

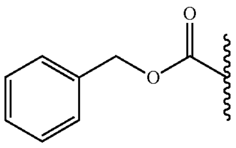
Cbz

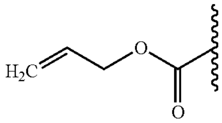
Alloc

Me

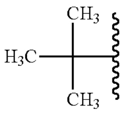
t-butyl

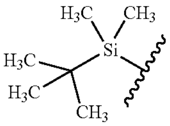
TBDMS

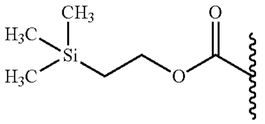
Teoc

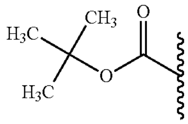
Boc

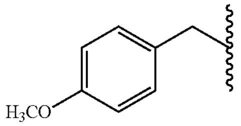
pMB

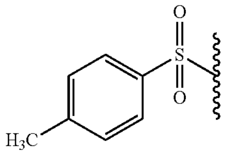
tosyl

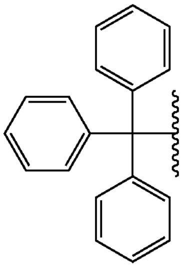
trityl

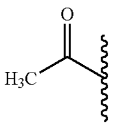
acetyl

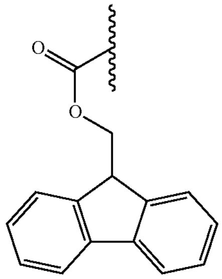
Fmoc

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range.

Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments±50%, in some embodiments±20%, in some embodiments±10%, in some embodiments±5%, in some embodiments±1%, in some embodiments±0.5%, and in some embodiments±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following examples have been included to provide guidance to one of ordinary skill in the art for practicing representative embodiments of the presently disclosed subject matter. In light of the present disclosure and the general level of skill in the art, those of skill can appreciate that the following examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Summary

A structure-based computational search of a large commercial library was performed targeting a binding pocket on the urokinase receptor (uPAR). The top ranking candidates identified by this search were tested experimentally for uPAR binding. Two compounds, namely (3R)-4-cyclohexyl-3-(hexahydrobenzo[d][1,3]dioxol-5-yl)-N-((hexahydrobenzo[d][1,3]dioxol-5-yl)methyl)butan-1-aminium (IPR-1) and 4-(4-((3,5-dimethylcyclohexyl)carbamoyl)-2-(4-isopropylcyclohexyl)pyrazolidin-3-yl)piperidin-1-ium (IPR-69) with micromolar inhibition were discovered. Synthesis of these compounds afforded a concentration-dependent study that revealed inhibition of breast MDA-MB-231 invasion, migration and adhesion with IC50 near 30 μM. Both compounds exhibited greater potency in blocking angiogenesis in a tube formation assay with an $IC_{50}$ of 3 μM. The compounds also showed impairment of matrix metalloproteinase (MMP-9) activity in a gelatin zymography assay suggesting direct involvement in blocking degradation of the ECM. An MTT assay showed that IPR-9 and IPR-69 inhibited cell growth with $IC_{50}$ of 6 μM and 18 μM, respectively. Flow cytometry analysis revealed that the compounds induced apoptosis of MDA-MB-231 cells. A series of biochemical experiments that include DNA binding, inhibition of cytochrome P450 (CYP2C9), and blockage of hERG potassium channel revealed lead-like properties for IPR-69, but not IPR-9, which was a potent inhibitor of CYP2C9. IPR-69 administered orally reached peak concentration of nearly 40 μM with a half-life of about 2 hours. The efficacy of IPR-69 on invasion and metastasis was assessed in vivo using NOD-SCID mice inoculated with TMD-231 in their mammary fat pads. These cells are a variant of the MDA-MB-231 parental line and readily metastasize to the lungs. The cohort of treated mice showed a 20% reduction in tumor volumes and less extensive metastasis to the lungs compared with untreated mice. The suitable pharmacokinetic properties of IPR-69 and the encouraging preliminary results in metastasis make it an ideal starting point to design next generation compounds to block tumor invasion and metastasis.

Example 2

Materials and Methods

Fluorescence Polarization Assay. The fluorescence polarization assay used fluorescent AE147-FAM peptide. uPAR was titrated against the fluorescent AE147-FAM peptide and data were fit to a sigmoidal dose-dependent curve as the FP value increases to determine the Kd of binding using Sigmaplot (Systat Software Inc., CA). Inhibitor screens were carried out in triplicates using 500 nM uPAR, 100 nM AE147-FAM, and inhibitor concentrations ranging from 0.78 μM to 100 μM in 50 μL volumes in black BD Falcon 384-well microplate. The compounds were serially diluted in DMSO then diluted in to 0.01% Triton X-100 in 1×PBS buffer ensuring a final concentration of 2% DMSO (a concentration that did not affect peptide binding to uPAR). Polarized fluorescence intensities were measured immediately following addition of inhibitors to the protein-peptide mix at room temperature on an EnVision® Multilabel Plate Readers (PerkinElmer) with excitation and emission wavelengths of 485 nm and 530 nm, respectively.

Proliferation Assay. The procedure consisted of culturing cells at 37° C. in 10% FBS-DMEM medium containing various amounts of compound. 5 mM compound stock in 100% DMSO was 1:50 diluted in medium, filtered, and serially diluted in 96-well plate. Then seeded cells were incubated for 3 days. Viable cells were quantified by MTT assay at absorbance of 570 and 630 nm.

Invasion and Migration Assays. These assays were performed using BD BioCoat Matrigel Invasion Chamber (Cat. 354480, BD Biosciences, Bedford, Mass.). The undersurface of the inserts was coated with 30 μg/mL of fibronectin (Sigma, F2006) in PBS at 4° C. overnight. The inserts were washed with PBS once. Then, 0.5 mL of serum-free medium was separately added to the upper and lower chambers to equilibrate the Matrigel invasion chambers at 37° C., 5% $CO_2$ for 2 hours. After starvated with serumfree DMEM or 4 hours, subconfluent MDA-MB-231 cells were trypsinized and resuspended in 0.1% FBS DMEM. $5\times10^4$ cells in 500 μL of 0.1% FBS DMEM containing various compounds or 1.0% DMSO (as control) were added to the upper chambers.

500 μL of 10% FBS DMEM containing the same concentration of the same compound or DMSO were added to the lower chambers. We incubated the invasion chambers for 3 hours at 37° C., 5% $CO_2$. Non-invaded cells were removed from the upper chamber with a cotton swab. The invaded cells were fixed with 100% methanol and then stained with Hematoxylin Stain Harris Modified Method (Fisher, SH30-500D). The filters were washed with water 3 times. Filters were air dried and the invaded cells were counted in ten randomly selected microscopic fields (×200 magnification). The experiment was performed in triplicate per group and shown by mean±SE.

Gelatin Zymography. MDA-MB-231 cells were treated with different concentrations of uPAR compounds in serum free medium for 24 h, the conditioned medium were collected, concentrated by Amicon Ultra centrifugal filter units (Millipore, #UFC500324), proteins were normalized and electrophoresed on sodium dodecyl sulfate (SDS)-polyacrylamide gels (10%) containing 1 mg/mL gelatin. After electrophoresis, the gel was washed twice in 50 mM Tris-HCl (pH 7.6) containing 5 mM $CaCl_2$ and 2.5% Triton X-100 for 30 minutes at room temperature and incubated in buffer that contained 50 mM Tris-HCl (pH 7.6), 200 mM NaCl, 10 mM $CaCl_2$ at 37° C. for 36 h. Then, the gels were stained with 0.05% Coomassie brilliant blue (CBB) and destained with 30% methanol in 10% acetic acid. Areas of gelatinolytic degradation appeared as transparent bands on the blue stained background of the gel. Data were quantified using Image J.

Adhesion Assay. Quantitative cell adhesion assays were carried out in nontissue culture treated 96-well microtiter plates (Evergreen Scientific, Los Angeles, Calif.) which were coated with 15 μg/mL fibronectin (Sigma) for 1 h at room temperature. Fibronectin coated and uncoated control wells were blocked for 1 h with 3% heat denatured bovine serum albumin (BSA) at 37° C. Cells were split one day prior to the experiment to achieve a subconfluent culture. Briefly, MDA-MB-231 cells were collected with trypsin, quenched with soybean trypsin inhibitor (Calbiochem), washed twice with serum-free medium, and 2×104 cells in 100 μL serum-free medium containing various compounds were added to each well, quadruplicate per group and incubated for 90 min at 37° C. The wells were washed and the number of adherent cells was quantified by crystal violet staining at 570 nm.[19,20] The results were shown by means±SE.

Angiogenesis Assay. Matrigel assays were performed as previously described with minor modifications.[21] Early-passage (2-3) cord blood-derived endothelial cells were seeded onto 96-well tissue culture plates coated with 40 μL Matrigel (BD Biosciences) at a cell density of 7500 cells per well. Cells were observed every 2 hours by visual microscopy with an inverted microscope at 40× magnification for capillary-like formation. The percentage of the tube formation to the vehicle control group was calculated for each compound treated group.

Cloning, Expression and Purification of uPAR. uPAR was successfully cloned, expressed and purified. From 1 L of culture, nearly 12 mg of protein was expressed, which will be sufficient to conduct the experiments disclosed herein. Briefly, a truncated, soluble form of human uPAR (suPAR, amino acids 1-283) was expressed in stably transfected *Drosophila* S2 cells using the *Drosophila* Expression System (Invitrogen). suPAR was obtained by a two-step purification process. The conditioned culture medium was filtered (0.45 μm) and loaded onto a DEAE Sephadex column equilibrated with 20 mM Tris (pH 7.4). The protein was eluted with a gradient of 0-1 M NaCl in 20 mM Tris (pH 7.4). suPAR containing fractions were then pooled, concentrated, and filtered prior to RP-HPLC using a semi-preparative (10×25 cm) C8 column. A 1 mL aliquot of the concentrated protein was loaded onto the column at initial gradient conditions of 95% eluent A and 5% eluent B, where eluent A was 0.1% TFA/100% H2O and eluent B was 70:30 acetonitrile/0.00085 MeCN/$H_2O$/TFA. The protein elutes using a gradient of 5% eluent A to 95% eluent B over 46 minutes at a flow rate of 4 mL/min. Under these conditions, the protein eluted as a single sharp peak (tR=29 min). SDS page analysis of the uPAR containing fractions showed a single band at the expected mass of 60 kDa. Surface plasmon resonance confirmed that the purified uPAR was capable of binding to uPA. The identity of the 60 kDa band was established by immunoblot (not shown).

Apoptosis Assay. MDA-MB-231 cells were cultured in DMEM medium supplemented with 10% FBS, 100 IU/mL penicillin and 50 μg/mL streptomycin in a humidified atmosphere containing 5% $CO_2$ at 37° C. and grew to 80-90% confluence in P-60 mm plates, then treated with various amounts of compounds or 1% DMSO (as control) for different time points. Collected the supernatants and washed the cells with 1×PBS twice and collected. The cells were detached by using cellstripper (Mediatech Inc, VA), and washed twice with cold 1× PBS and resuspended in 1× binding buffer (Cat. PNN1001, Invitrogen Corporation, Camarillo, Calif.) at a concentration of $1\times10^6$ cells/mL. Transferred 100 μL of the solution ($1\times10^5$ cells) to a 5 mL culture tube. Added 5 μL of Recombinant Human Annexin V FITC conjugate (Cat. ANNEXINV01, Invitrogen) and 5 μL of propidium iodide solution (Cat. P4864, Sigma-Aldrich, St. Louis, Mo.). Gently vortexed the cells and incubated for 15 min at room (25° C.) in the dark. Added 400 μL of 1× binding buffer to each tube. Analyzed by flow cytometry (FACScan).

Immunoblots. MDA-MB-231 cells treated with 100 μM of compound(s)/1% DMSO for 30 min. Harvested cell lysates in RIPA buffer supplemented with protease inhibitors and phosphatase inhibitors. Under non-reducing condition equal amounts of protein were loaded per lane and separated in 4-12% NuPAGE gel (Invitrogen) at 200 V for 60 minutes, then transferred to Nitrocellulose membrane at 30 V for one hour using XCell II blot module. IB: First antibody Phosph-p44/42 MAPK (Thr202/Tyr204) (D13.14.4E) rabbit mAb (#4370, Cell Signaling Technology, Inc., Danvers, Mass.) 1:2000 or P44/42 MAP Kinase (137F5) rabbit mAb (#4695, Cell Signaling Technology, Inc., Danvers, Mass.) 1:500 in 5% non-fat milk-TBST at 4° C. overnight. Secondary antibody: goat anti-rabbit IgG HRP 1:3000 in 5% non-fat milk-TBST at room for 1 hour. The protein bands were visualized using Immobilon Western Chemiluminescent HRP Substrate (WBKLS0100, Millipore, Billerica, Mass.). Fibronectin (Sigma, F2006) 30 Cg/mL coated in 6-well plates overnight. MDA-MB-231serum-starved for 4 hours and then seeded in FN coated 6-well plates and treated with 5,10, 20 and 40 μM compound(s)/1% DMSO for 30 min, cells were lysated in RIPA buffer supplemented with protease inhibitors and phosphatase inhibitors. Then IB with phospho-p44/42 MAPK (Thr202/Tyr204), p44/42 MAPK; phospho-FAK (Tyr397), FAK; phospho-Src family (Tyr416), Src, respectively.

Pharmacokinetics of the Leads in Rodents. A method to quantify IPR-69 in plasma was developed using HPLC-MS/MS (API 3200; Applied Biosystems). A 20 μL plasma sample was extracted with methyl tertiary butyl ether (MTBE) under neutral conditions (0.1 M phosphate buffer pH=7.4) using temazepam as the internal standard. The extract is evaporated, reconstituted with mobile phase and injected into the HPLC. The HPLC column is a C-8 50×4.6 mm 5-μm column and separation of UPR and temazepam occurred by a linear gradient mobile phase starting with acetonitrile:0.1% formic acid (10:90) and changing to 80:20. The m/z Q1 and Q3 settings on the API 3200 for UPR and temazepam are 418/297 and 301/255, respectively. The lower limit of quantification of IPR-69 is 1 ng/mL using 20 μL of plasma. A standard response curve of IPR-69 was created with concentrations that varied from 1 ng/mL to 1000 ng/mL using 300 ng/mL of temazepam for each sample. To determine drug concentrations of the lead inhibitors in the pharmacological models, the PK properties of the compounds in mice must be characterized. The PK of IPR-69 was determined in NOD/SCID mice following a single dose given PO. The study design used 3 mice per time point. Blood was collected at time intervals from 0 to 24 hours after dosing (8 time points), quantified by the procedure described above. Pharmacokinetic parameters for IPR-69 including area under the curve (AUC), area under the moment curve (AUMC), and $t_{1/2}$ were estimated using non-compartmental methods with Excel®. The maximum plasma concentration ($C_{max}$) and time of $C_{max}$ ($t_{max}$) were obtained from the data. The AUC from zero to infinity ($AUC_{0-\infty}$) was estimated from the $AUC_{0-t}$ (time zero to the last quantifiable concentration $C_{last}$) and the AUC from $C_{last}$ to infinity, $C_{last}/k_{el}$, where $k_{el}$ is the rate constant of elimination. The $AUMC_{0-\infty}$ was estimated by an analogous manner. The systemic clearance (Cl/F, where F=bioavailability) of IPR-69 was calculated from the dose and $AUC_{0-\infty}$.

Mouse Xenograft Studies. NOD/SCID mice were obtained from the on-site breeding colony maintained by the In Vivo Therapeutics Core at the Indiana University Simon Cancer Center (IUSM, Indianapolis, Ind.) and maintained in pathogen-free conditions within the laboratory animal resources center (LARC) at the Indiana University School of Medicine according to an approved protocol by the Institutional animal care and use committee (IACUC) committee. TMD-231 cells ($1\times10^6$) were be injected into the mammary fat pads (m.f.p.) of 4-6 week old mice.

These cells have been shown previously to develop primary tumors and metastasize efficiently to the lungs when the primary tumors have been removed.[22]

For metastasis studies, m.f.p. tumors were allowed to grow to approximately 100 $mm^3$ mice. Mice were assigned to treatment group based on average tumor size/weight. Following a recovery period of two days, mice received treatment of investigational drug (n=15) or a PBS solvent control (n=15). After four weeks mice were euthanized, the lungs were resected, fixed in formalin solution, sectioned, and stained with hematoxylin and eosin (H&E) for analysis. The number and size of metastasis in two to five fields per sample were calculated and a score of 4+ was given to a sample with highest metastasis index and relative metastasis in other samples are calculated (i.e., 1+, 2+, 3+) by a sample-blinded pathologist. Tumor volume were be calculated as Length*Width$^2$/2 in millimeters.

Example 3

Structure-based Virtual Screening by Docking Compounds to uPAR

Analysis of the three dimensional structure of uPAR revealed a hydrophobic pocket that accommodates the growth-factor domain (GFD) of its serine proteinase ligand uPA (PDB ID: 2FD6). The 300,000 compounds in the ChemDiv library were docked into the pocket using the computer program AutoDock4. The resulting complexes were scored with several scoring functions that include ChemScore;[22,23] AutoDock,[24] and DOCK.[25]

The top ranking 200 compounds for each scoring function were visualized, and clustered by chemical similarity. About 50 compounds were selected among the top compounds from each scoring function. A total of 210 compounds were acquired from ChemDiv for biochemical evaluation.

Example 4

Biochemical Assessment of Compound Binding to uPAR

The design of a fluorescent probe was guided by the three-dimensional structure of uPAR in complex with peptide AE147.[27] As this peptide binds at the same site that is occupied by the growth factor-like domain of uPA, it provides the basis for the development of a competition assay to assess binding to this site. Flurescein was introduced to the N-terminus of AE147. The resulting peptide, AE147-FAM, binds to uPAR with high affinity with an estimated $K_D$ of 120 nM, and show similar potency to the EGF-like domain of uPA (FIG. 1A).[27] Increasing concentrations of suPAR protein were titrated against the fluorescent GFD-FAM peptide.

All 210 compounds were screened at initial concentration of 50 μM for displacement of AE147-FAM peptide. Eleven compounds gave polarization readings that were five times that of the standard deviation of the control peptide (FIG. 1B). Secondary concentration-dependent study for these eleven compounds was performed. Among them, two compounds, IPR-1 and IPR-69 of Formulae (XIV) and (V) below, respectively, showed concentration-dependent inhibition (FIG. 1C):

Formula (XIV)

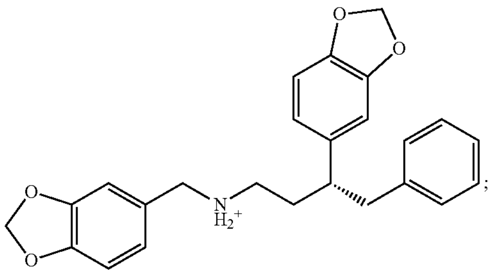

; and

Formula (XV)

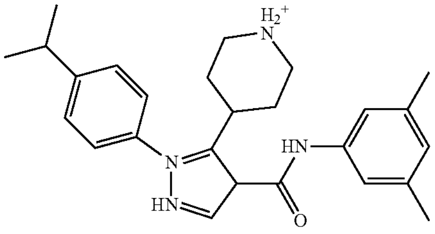

The resulting inhibition curves were used to determine an inhibition constant, $K_i$, for each. The $K_i$ value for (3R)-4-cyclohexyl-3-(hexahydrobenzo[d][1,3]dioxol-5-yl)-N-((hexahydrobenzo[d][1,3]dioxol-5-yl)methyl)butan-1-aminium (IPR-1) was 18 μM, while the $K_i$ value for 4-(4-((3,5-dimethylcyclohexyl)carbamoyl)-2-(4-isopropylcyclohexyl)pyrazolidin-3-yl)piperidin-1-ium (IPR-69) was 30 μM (FIG. 1C).

Example 5

Cellular Assays to Probe Effect on Metastasis

Whether the two active compounds affected invasion, adhesion and migration in cell culture in a concentration-dependent study was tested (FIGS. 2A, 2B). For invasion, the Transwell (or Boyden) chamber assay was used.[28] The assay uses a chamber with two compartments that are separated by a microporous membrane known as Matrigel consisting of components of the ECM such as collagen, laminin and fibronectin.[28]

Invasive tumor cells degrade the Matrigel and migrate through the membrane to the lower compartment. Instead of IPR-1, a more soluble analog (IPR-9) was tested. IPR-9 had an inhibition constant (20 μM) similar to that of IPR-1. Both IPR-9 and IPR-69 substantially impaired MDA-MB-231 invasion (FIGS. 2A, 2B) with $IC_{50}$ of 30 μM for both IPR-9 and IPR-69. To assess whether compounds inhibit cell migration, the same Boyden chamber apparatus is used except that the porous membrane is not coated with the Matrigel layer. FIGS. 2A and 2B show the effect of representative presently disclosed compounds on MDA-MB-231 metastasis. Percent inhibition of invasion, migration, and adhesion of MDA-MB-231 by compounds that bind to uPAR. IPR-9 and IPR-69 also significantly block migration of MDA-MB-231 across the membrane (FIG. 2A). The $IC_{50}$ values (43 μM for IPR-9 and 40 μM for IPR-69) were somewhat larger than the values observed for invasion (FIGS. 2A, 2B).

The effect of compounds on cell attachment (adhesion) to wells pre-coated with fibronectin was evaluated using an assay we have described previously.[29]

Similar assays have evaluated extensively uPAR-mediated cell attachment to ECM components mediated by integrin.[30-32] Both IPR-9 and IPR-69 inhibited adhesion in a concentration dependent manner with $IC_{50}$ values of 45 μM (FIGS. 2A, 2B).

Example 6

Angiogenesis

The formation of new blood vessels from pre-existing ones is known as angiogenesis, which is vital for tumor growth, invasion, and metastasis. The effect of IPR-9 and IPR-69 on angiogenesis was assessed in human umbilical vein endothelial cells (HUVEC) in a Matrigel-based tube formation assay.[33]

FIGS. 3A, 3B, 3C, 3D show the effect of IPR-69 and IPR-9 tube formation in matrigel by HUVEC cells. Both compounds inhibited tube formation in Matrigel in a concentration-dependent manner (FIGS. 3A, 3B, 3C, 3D). As illustrated from the images in FIGS. 3A, 3B, 3C, 3D, less tube formation is observed with increasing concentration of compound for both IPR-9 and IPR-69. The extent of tube formation is quantified as shown by the histogram plots in FIGS. 3B, 3D and afforded an estimation of $IC_{50}$.

Interestingly, both IPR-9 and IPR-69 showed greater potency in blocking angiogenesis by nearly an order of magnitude ($IC_{50}$=3 μM) in comparison with invasion.

Example 7

Effect on Cell Proliferation and Mechanism of Cell Killing

An MTT assay revealed that IPR-9 and IPR-69 inhibited cell proliferation with $IC_{50}$ of 6 and 17 μM, respectively (FIGS. 4A and 4C). FIGS. 4A-4D show inhibition of MDA-MB-231 proliferation and mechanism of cell killing. To gain insight into the mechanism by which these compounds are inhibiting growth, a flow cytometry analysis with annexin V-FITC and PI staining was performed. The level of apoptotic cells in MDA-MB-231 was assessed by the percentage of Annexin V-positive/PI-negative cells present after exposure of MDAMB-231 cells to increasing concentration of IPR-69 for 24 h (FIG. 4B). At a concentration of 50 μM, IPR-69 induced significant apoptosis as evidenced by a 51% and 21% increase in apoptotic cells (Annexin V positive/PI-negative) and necrotic cells (Annexin V-positive/PI-positive), respectively. A similar analysis for IPR-9 indicated that the compound promoted cell death via both necrosis and apoptosis as illustrated in FIG. 4D. At a concentration of 50 μM, 26% of cells were necrotic (Annexin V positive/PI-positive), a 22% increase over control. 46% of cells were apoptotic (Annexin V positive/PInegative), compared with 4% of control.

Example 8

IPR-69 and IPR-9 Block MMP-9 Activity in MDA-MB-231 Cells

To degrade collagen within the ECM, malignant cells unleash a series of extracelullar proteases known as matrix metalloproteinases (MMPs). Inhibition of MMP activity with small molecules has been a cornerstone of efforts to develop drugs that block tumor invasion and metastasis.[34] The gelatinases (MMP-2 and MMP-9) in particular have been strongly associated with invasion and metastasis. Whether IPR-9 and IPR-69 impaired MMP-9 (gelatinase B) activity was accessed. When exposed to IPR-69 and IPR-9 at increasing concentration, MDA-MB-231 cells showed a concentration-dependent reduction in MMP-9 activity (FIGS. 5A, 5B, 5C, 5D). FIGS. 5A, 5B, 5C, 5D show the effect of representative presently disclosed compounds on ECM degradation.

$IC_{50}$ for inhibition of MMP-9 activity by IPR-9 and IPR-69 were estimated at 25 μM, which corresponded well with the $IC_{50}$ for inhibition of invasion that were observed from the Boyden chamber study. At 50 μM, IPR-69 nearly completely abrogated MMP-9 activity with 93% inhibition of MMP-9 activity.

Example 9

Cell Signaling

In light of the previously reported role of uPAR in signaling, the effect of IPR-1, IPR-9 and IPR-69 on signaling was studied by Western blot analysis. Following exposure of the compounds at a concentration of 100 μM to MDA-MB-231 cells for 30 minutes, immunoblotting revealed significant impairment of MAPK phosphorylation by IPR-1 and IPR-9 (FIG. 6A). IPR-69 also abrogated phosphorylation, but the effects were weaker than IPR-9 and its parent compound (FIG. 6A). A concentration-dependent study was subsequently carried out for IPR-1 (FIG. 6B). The results confirmed that the compound completely abrogated phosphorylation of MAPK, with an $IC_{50}$ estimated at approximately 20 μM. The effect of the compound also was studied in two other signaling pathways including FAK and Src. FAK is constitutively associated with β-integrin subunits of integrin receptors. The compound did not show any significant effect on FAK phosphorylation compared with DMSO. Even less effect was observed on phosphorylation of Src, which is upstream of MAPK (FIG. 6B). This observation suggests that IPR-1 is unlikely to impair integrin signaling. The effect of the compounds on MAPK and the lack of effect on FAK and Src signaling suggest that the compounds are not promiscuous and their effects on metastasis can be attributed to the targeting of specific signaling pathways.

Example 10

Synthesis of IPR-9 and IPR-69

Overview. As shown in Scheme 1, the synthesis of N-1 substituted pyrazole IPR-69 followed the route developed by scientists at Abbott Laboratories. The pyrazole core was prepared by condensation of 1,3-dicarbonyl enol ethers with a variety of hydrazines. The yield was good to excellent in all cases.[35] Thus, commercially available N-Boc isonipecotic acid 1 was converted to known β-keto ester 3 through a simple two-step sequence (condensation of Meldrum's acid followed by ethanolysis).[36]

Alternatively, condensation of the acid chloride of 1 with potassium ethyl malonate in the presence of a magnesium chloride-triethylamine base system also gave 3.[37] With the requisite β-keto ester 4 in hand, the formation of pyrazole core was explored with commercially available 4-isopropyl phenylhydrazine. The amide bond formation followed by the removal of NBoc gave the desired N-1 substituted pyrazole IPR-69.

Scheme 1

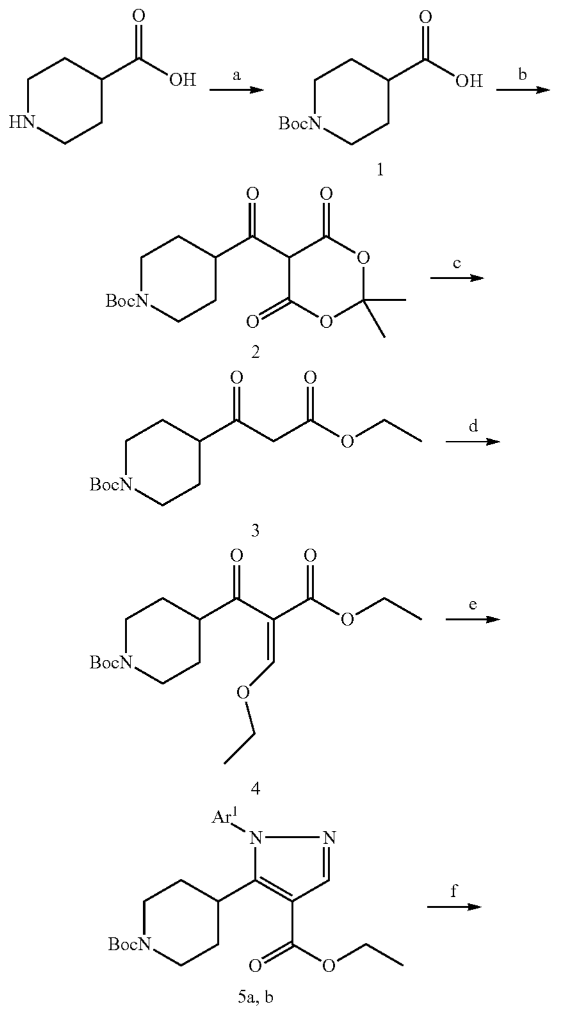

1

2

3

4

5a, b

-continued

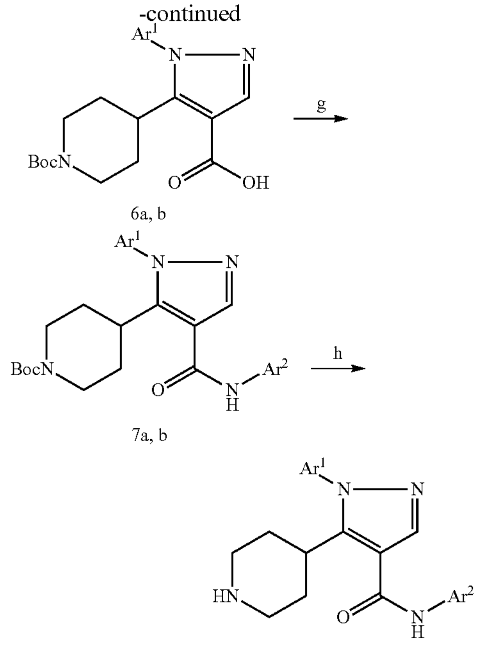

6a, b 7a, b 8a, b a: $Ar^1$ = 4-isopropylphenyl
b: $Ar^1$ = 3,4-dimethylphenyl
7-8a, b: $Ar^2$ = 3,5-dimethylphenyl (IPR-69/IPR-81)
9a: $Ar^2$ = 2-aminophenethylalcohol (IPR-616)
10a: $Ar^2$ = 2-amino-3-methylbenzylalcohol (IPR-617)
11a: $Ar^2$ = 3'-aminoacetanilide (IPR-618)
12a: $Ar^2$ = 3-aminophenol (IPR-619)
13a: $Ar^2$ = 4-amino-2,5-dimethylphenol ((IPR-620)
14a: $Ar^2$ = 2-aminobenzylalcohol (IPR-621)
15a: $Ar^2$ = 2'-aminoacetanilide (IPR-622)
16a: $Ar^2$ = 8-aminoquinoline (IPR-623)
17b: $Ar^2$ = 3-methoxy-5-trifluoromethylbenzyl (IPR-735)
18b: $Ar^2$ = 5-methoxy-2-methylbenzyl (IPR-736)
19b: $Ar^2$ = 2-benzyloxy (IPR-737)
20b: $Ar^2$ = 3-methylbenzyl (IPR-738)
21b: $Ar^2$ = 2-(ρ-tolyl)ethyl (IPR-739)
22b: $Ar^2$ = 3-fluorophenethyl (IPR-740)
23b: $Ar^2$ = 2-fluorophenethyl (IPR-741)
24b: $Ar^2$ = 4-fluorophenethyl (IPR-743)
25b: $Ar^2$ = 4-isopropylbenzyl (IPR-744)
26b: $Ar^2$ = 4-propylbenzyl (IPR-745)
27b: $Ar^2$ = 4-tert-butylbenzyl (IPR-746)
28b: $Ar^2$ = 5-chloro-2-methoxybenzyl (IPR-747)
29b: $Ar^2$ = 4-methoxy-2-methylbenzyl (IPR-748)
30b: $Ar^2$ = 2,4-dimethylbenzyl (IPR-749)

Reagents and Conditions for synthesis of compounds in Scheme 1: (a) $K_2CO_3$, di-tert-butyl-di-carbonate, THF:$H_2O$, 0° C.; (b) DMAP, DCC, 2,2-dimethyl-1,3-dioxane-4,6-dione, DCM, 0° C.; (c) ethanol, reflux; (d) triethylorthoformate, acetic anhydride, reflux; (e) ethanol, 4-isopropyl phenyl hydrazine, reflux; (f) 2.0 M NaOH (aq), ethanol, 70° C.; (g) DMAP, DCC, 3,5-dimethylaniline, DCM, 0° C.; and (h) trifluoroacetic acid:DCM, 0° C.

The synthesis of a secondary benzyl amine IPR-9 (Formula (XV)), as shown in Scheme 2 below, used 1,4-conjugate addition and reductive amination. Thus, Knoevenagel condensation between commercially available phenylacetaldehyde and diethyl malonate using a catalytic amount of piperidine and acetic acid in refluxing toluene gave 8, then subjected to the conjugate addition conditions developed by Bosch, where excess of CuCl promoted an efficient conjugate addition of Grignard reagents. With the desired Michael adduct 9 to aldehyde 12 was achieved by a sequence of conventional functional group manipulation; hydrolysis, decarboxylation, reduction, and oxidation. The reductive amination between aldehyde 12 and commercially available 4-(dimethylamino)benzylamine dihydrochloride gave the desired secondary amine IPR-9 as a racemate.

Scheme 2

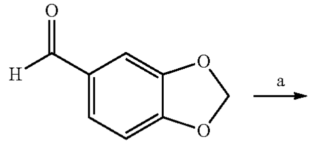

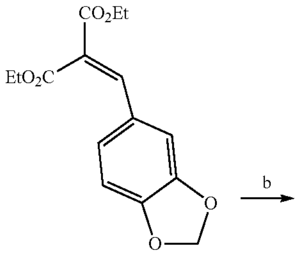

8

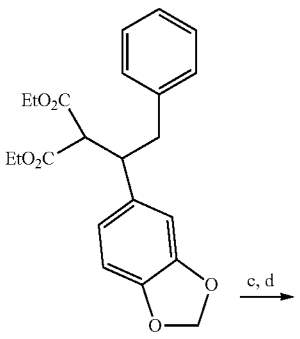

9

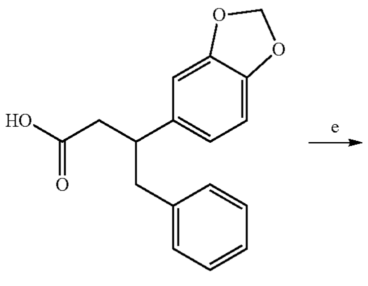

10

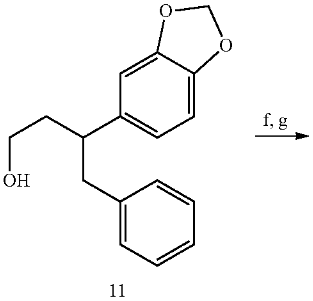

11

-continued

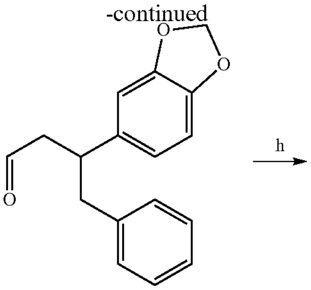

12

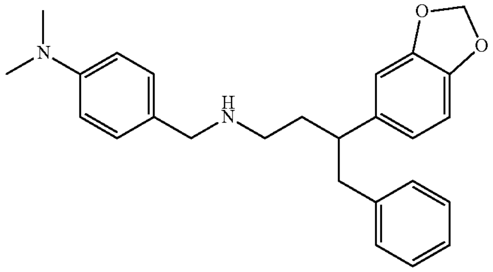

IPR-9
Formula (XV)

Reagents and conditions for synthesis of compounds in Scheme 2: cat. Piperidine/AcOH toluene, reflux, diethyl malonate; (b) BnMgCl, CuCl, −78° C. to r.t.; (c) 10% KOH MeOH:$H_2O$ (1:1) r.t.; (d) p-xylene, reflux; (e) $LiAlH_4$, THF 0° C. to r.t.; (f) $Et_3N$, DMSO, $SO_3Py$, DCM, 0° C.; (g) 4-(aminomethyl)-N,N-dimethylaniline hydrochloride; and (h) $Na(ACO)_3BH$, THF, r.t.

Methods and Material. All chemicals were purchased from either Aldrich oir Acros and used as received. Column chromatography was carried out with silica gel (25-63 μm). Mass spectra were measured on an Agilent 6520 Accurate Mass Q-TOF instrument 1H NMR spectra were recorded in $CDCl_3$ or Methano-d4 on a Bruker 500 MHz spectrometer. Chemical shifts are reported using residual CDC13 or MeOH as internal references.

1-(tert-butoxycarbonyl)piperidine-4-carboxylic acid (1)—To a stirred solution of isonipecotic acid (77.4 mmol, 10.0 g) and potassium carbonate (154.8 mmol, 21.4 g) in water (150 mL) at 0° C., was added dropwise a solution of di-t-butyldicarbonate (77.4 mmol, 16.9 g) in THF (150 mL). The reaction mixture was gradually warmed to r.t. and stirred overnight. The solvents were evaporated and the residue was dissolved in DCM. DCM layer was washed with 1N HCl (3×100 mL), water, dried over sodium sulfate, and concentrated in vacuo to give pure 1 (13.03 g, 75%) as a white powder. $^1H$ NMR (500 MHz, $CDCl_3$) δ 4.02 (br s, 2H), 2.85 (t, J=11.5 Hz, 2H), 2.49 (m, 1H), 1.90 (d, J=11.5 Hz, 2H), 1.65 (m, 2H), 1.45 (s, 9H); $^{13}C$ NMR (125 MHz, $CDCl_3$) δ 180.1, 154.7, 79.7, 40.7, 28.3, 27.6. MS calculated for $C_{11}H_{18}NO_4$ $(M-H)^-$ 228.1241, found 228.1240.

tert-butyl-4-(2,2-dimethyl-4,6-dioxo-1,3-dioxane-5-carbonyl)piperidine-1-carboxylate (2)—To a stirred solution of 1 (56.8 mmol, 13.03 g) and DMAP (5.68 mmol, 694 mg) in DCM (10 mL) at 0° C., were added DCC (62.5 mmol, 12.9 g) and 2,2-dimethyl-1,3-dioxane-4,6-dione (62.5 mmol, 9.00 g) sequentially. The reaction mixture was gradually warmed to r.t. and stirred overnight. Reaction was filtered and washed with DCM. The resultant orange solution was concentrated in vacuo. Product was used directly without isolation.

tert-butyl-4-(3-ethoxy-3-oxopropanoyl)piperidine-1-carboxylate (3)—To 2, was added abs. ethanol (200 mL) and the solution was refluxed for 48 h. The solution was concentrated in vacuo and purified by flash chromatography (DCM) to give 3 as a reddish oil (14.36 g, 85%). $^1$H NMR (500 MHz, $CDCl_3$) δ 12.09 (s, 0.14H, enol OH), 4.89 (s, 0.14H enol C—H), 4.13 (q, J=7 Hz, 2H), 4.10-3.96 (m, 2H), 3.42 (s, 2H), 2.81-2.67 (m, 2H), 2.62-2.52 (m, 1H), 1.85-1.71 (m, 2H), 1.55-1.43 (m, 2H), 1.39 (s, 9H), 1.21 (t, J=7 Hz, 3H); $^{13}$C NMR (125 MHz, $CDCl_3$) δ 204.0, 180.2 (enol), 172.7 (enol), 167.0, 154.4, 87.52, 79.51, 61.3, 48.5, 47.1, 28.2, 27.1, 13.9; Rf=0.2 (DCM). HRMS calculated for $C_{15}H_{26}NO_5$ $(M+H)^+$ 300.1805, found 300.1808.

(E,Z)-tert-butyl-4-(3-ethoxy-2-(ethoxycarbonyl)acryloyl) piperidine-1-carboxylate (4)—Under argon, 3 (47.9 mmol, 14.36 g), triethyl orthoformate (143.7 mmol, 24 mL), and acetic anhydride (95.8, 9 mL) were mixed and refluxed at 100° C. for 48 h. Low-boiling impurities were evaporated off and the crude product was purified by flash chromatography (DCM) to give 4, as a yellow-colored oil (14.92 g, 88%). Rf=0.22 (1% MeOH/DCM). $^1$H NMR (500 MHz, $CDCl_3$) δ 7.59 (s, 0.54 H, minor), 7.52 (s, 1H, major), 4.24 (q, J=7.1 Hz, 2H), 4.21-4.09 (m, 7H), 4.08-3.92 (m, 4H), 3.09-3.01 (m, 0.58H, minor), 2.95-2.87 (m, 1H, major), 2.83-2.67 (m, 4H), 1.85-1.67 (m, 4H), 1.58-1.47 (m, 4H), 1.41 (s, 19H), 1.37-1.26 (m, 9H), 1.23 (t, J=7.1 Hz, 6H); $^{13}$C NMR (125 MHz, $CDCl_3$) δ major isomer: 201.7, 165.7, 165.3, 162.3, 154.61, 112.6, 79.3. 72.2, 60.5, 48.0, 45.4, 28.3, 27.2, 15.2, 14.2; minor isomer 199.6, 165.2, 154.59, 112.9, 72.7, 60.7, 28.0, 15.1, 14.1. MS calculated for $C_{18}H_{30}NO_6$ $(M+H)^+$ 356.2068, found 356.2067.

tert-butyl-4-(4-(ethoxycarbonyl)-1-(4-isopropylphenyl)-1H-pyrazol-5-yl)piperidine-1-carboxylate (5)—Free hydrazine was prepared from HCl salt by washing with sat. sodium bicarbonate solution and extracting with DCM. DCM was removed in vacuo. To a stirred solution of free 4-isopropyl phenyl hydrazine (21.7 mmol, 3.26 g) in abs. ethanol (100 mL), was added 4 (19.7 mmol, 7.00 g) in abs. ethanol (100 mL). The reaction was refluxed at 100° C. for 48 h. Ethanol was removed in vacuo and the crude reddish-brown residue was purified by flash chromatography (1% MeOH/DCM) to give 5 (6.27 g, 72%) as a reddish-brown oil. Rf=0.22 (1% MeOH/DCM) $^1$H NMR (500 MHz, $CDCl_3$) δ 8.00 (s, 1H), 7.33 (d, J=10 Hz, 2H), 7.22 (d, J=10 Hz, 2H), 4.29 (q, J=7.1 Hz, 2H), 4.13-4.01 (m, 2H), 3.14-3.05 (m, 1H), 3.03-2.94 (m, 1H), 2.66-2.51 (m, 2H), 2.31-2.20 (m, 2H), 1.50-1.30 (m, 2H), 1.43 (s, 9H), 1.35 (t, J=7 Hz, 3H), 1.28 (d, J=7 Hz, 6H); $^{13}$C NMR (125 MHz, $CDCl_3$) δ 163.2, 154.7, 150.3, 149.6, 142.8, 137.0, 127.3, 126.3, 112.0, 79.3, 60.0, 47.2, 35.1, 33.8, 28.4, 27.2, 23.8, 14.3.

5-(1-(tert-butoxycarbonyl)piperidin-4-yl)-1-(4-isopropylphenyl)-1H-pyrazole-4-carboxylic acid (6)—To a stirred solution of 5 (14.2 mmol, 6.27 g) in 95% ethanol (35 mL), was added a 2.0 M NaOH solution (35 mL). The reaction mixture was refluxed at 70° C. for 20 h. Ethanol was removed in vacuo and the resulting solid was acidified to pH 2 at 0° C. using 1M HCl. The reddish-brown solid was filtered off and washed with cold water to give 6 (3.98 g, 68%). $^1$H NMR (500 MHz, $CDCl_3$) δ 8.07 (s, 1H), 7.40-7.20 (m, 4H), 4.32-3.98 (m, 2H), 3.14 (app t, J=12 Hz, 1H), 3.05-2.94 (m, 1H), 2.71-2.52 (m, 2H), 2.37-2.20 (m, 2H), 1.65-1.52 (m, 3H), 1.47 (s, 9H), 1.31 (d, J=7 Hz, 6H); $^{13}$C NMR (125 MHz, $CDCl_3$) δ 168.2, 154.8, 150.6, 150.4, 143.5, 136.8, 127.3, 126.3, 111.1, 79.5, 35.1, 33.8, 28.5, 28.4, 27.3, 23.8. HRMS calculated for $C_{23}H_{32}N_3O_4$ $(M+H)^+$ 414.2387, found 414.2385.

tert-butyl-4-(4-((3,5-dimethylphenyl)carbamoyl)-1-(4-isopropylphenyl)-1Hpyrazol-5-yl)piperidine-1-carboxylate (7)—To a stirred solution of 6 (3.05 mmol, 1.26 g) and DMAP (0.30 mmol, 37 mg) in DCM (10 mL) at 0° C., was added DCC (3.35 mmol, 691 mg) and 3,5-dimethyl aniline (3.35 mmol, 483 mg) sequentially. The reaction was gradually warmed to r.t., and ran for 48 h. DCM was removed in vacuo and the crude mixture was purified by flash chromatography (30% EA/Hex) to give 7 (745 mg, 47%) as a brownish solid. $^1$H NMR (500 MHz, $CDCl_3$) δ 7.85 (s, 1H), 7.69 (s, 1H), 7.33 (d, J=8.3 Hz, 2H), 7.24 (d, J=8.3 Hz, 2H), 7.20 (s, 1H), 6.76 (s, 1H), 4.25-3.97 (m, 2H), 3.16 (app t, J=12 Hz, 1H), 3.00 (app p, J=7 10 Hz, 1H), 2.71-2.48 (m, 2H), 2.30 (s, 6H), 2.26-2.17 (m, 2H), 1.67-1.56 (m, 2H), 1.42 (s, 9H), 1.29 (d, J=7 Hz, 6H). $^{13}$C NMR (125 MHz, $CDCl_3$) δ 161.6, 154.8, 150.42, 148.9, 138.8, 138.5, 137.7, 137.2, 127.3, 126.5, 126.1, 117.9, 115.9, 79.3, 35.1, 33.9, 30.3, 29.4, 28.4, 23.9, 21.4; Rf=0.33 (30% EA/Hex). MS calculated for $C_{31}H_{39}N_4O_3$ $(M-H)^-$ 515.3028, found 515.3030.

N-(3,5-dimethylphenyl)-1-(4-isopropylphenyl)-5-(piperidin-4-yl)-1H-pyrazole-4-carboxamide (IPR-69)—To a stirred solution of 7 (1.44 mmol, 745 mg) in DCM (5 mL) at 0° C., was added TFA (5 mL). The reaction mixture was warmed to r.t. and stirred for 1 h. The solvents were removed in vacuo. The organic residue was re-dissolved in DCM. The organic layer was washed with sat. sodium bicarbonate, 20 brine, and dried over $MgSO_4$. The solvent was removed in vacuo to yield 8 (590 mg, 98%) as a brown solid. $^1$H NMR (500 MHz, $CDCl_3$) δ 7.86 (s, 1H), 7.49 (s, 1H), 7.38 (d, J=8.3 Hz, 2H), 7.25 (d, J=8.3 Hz, 2H), 6.79 (s, 1H), 3.34-3.27 (m, 2H), 3.26-3.19 (m, 1H), 3.09-2.95 (m, 1H), 2.72 (app t, J=13.2 Hz, 2H), 2.46 (qd, J=13, 9.7, 3.7 Hz, 2H), 2.32 (s, 6H), 1.74 (d, J=15 Hz, 2H), 1.32 (d, J=7 Hz, 6H); $^{13}$C NMR (125 MHz, $CDCl_3$) δ 161.8, 150.3, 149.1, 138.73, 138.69, 137.8, 137.0, 127.4, 126.2, 126.1, 118.0, 115.8, 46.2, 34.9, 33.9, 30.2, 23.8, 21.4. MS calculated for $C_{26}H_{33}N_4O$ $(M+H)^+$ 417.2649, found 417.2646.

5-(1-(tert-butoxycarbonyl)piperidin-4-yl)-1-(4-isopropylphenyl)-1H-pyrazole-4 carboxylic acid (6)—To a stirred solution of 5 (14.2 mmol, 6.27 g) in 95% ethanol (35 mL) was added a 2.0 M NaOH solution (35 mL). The reaction mixture was refluxed at 70° C. for 20 h. Ethanol was removed in vacuo and the resulting solid was acidified to pH 2 at 0° C. using 1M HCl. The light brown solid was filtered off and washed with cold water to give 6 (3.98 g, 68%). $^1$H NMR (500 MHz, $CDCl_3$) δ 8.07 (s, 1H), 7.40-7.20 (m, 4H), 4.32-3.98 (m, 2H), 3.14 (app t, J=12 Hz, 1H), 3.05-2.94 (m, 1H), 2.71-2.52 (m, 2H), 2.37-2.20 (m, 2H), 1.65-1.52 (m, 3H), 1.47 (s, 9H), 1.31 (d, J=7 Hz, 6H); $^{13}$C NMR (125 MHz, $CDCl_3$) δ 168.2, 154.8, 150.6, 150.4, 143.5, 136.8, 127.3, 126.3, 111.1, 79.5, 35.1, 33.8, 28.5, 28.4, 27.3, 23.8. HRMS calculated for $C_{23}H_{32}N_3O_4$ $(M+H)^+$ 414.2387, found 414.2385.

tert-butyl-4-(4-((3,5-dimethylphenyl)carbamoyl)-1-(4-isopropylphenyl)-1Hpyrazol-5-yl)piperidine-1-carboxylate (7)—To a stirred solution of 6 (3.05 mmol, 1.26 g) and DMAP (0.30 mmol, 37 mg) in DCM (10 mL) at 0° C. was added DCC (3.35 mmol, 691 mg) and 3,5-dimethyl aniline (3.35 mmol, 483 mg) sequentially. The reaction was gradually warmed to r.t., and ran for 48 h. DCM was removed in vacuo and the crude mixture was purified by flash chromatography (30% EA/Hex) to give 7 (745 mg, 47%) as a brownish solid. $^1$H NMR (500 MHz, $CDCl_3$) δ 7.85 (s, 1H), 7.69 (s, 1H), 7.33 (d, J=8.3 Hz, 2H), 7.24 (d, J=8.3 Hz, 2H), 7.20 (s, 1H), 6.76 (s, 1H), 4.25-3.97 (m, 2H), 3.16 (app t, J=12 Hz, 1H), 3.00 (app p, J=7 Hz, 1H), 2.71-2.48 (m, 2H), 2.30 (s, 6H), 2.26-2.17 (m, 2H), 1.67-1.56 (m, 2H), 1.42 (s, 9H), 1.29 (d, J=7 Hz, 6H). $^{13}C$ NMR (125 MHz, $CDCl_3$) δ 161.6, 154.8, 150.42, 148.9, 138.8, 138.5, 137.7, 137.2, 127.3, 126.5, 126.1, 117.9, 115.9, 79.3, 35.1, 33.9, 30.3, 29.4, 28.4, 23.9, 21.4; Rf=0.33 (30% EA/Hex). HRMS calculated for $C_{31}H_{39}N_4O_3(M-H)^-$ 515.3028, found 515.3030.

N-(3,5-dimethylphenyl)-1-(4-isopropylphenyl)-5-(piperidin-4-yl)-1H-pyrazole-4-carboxamide (IPR-69)—To a stirred solution of 7 (1.44 mmol, 745 mg) in DCM (2 mL) at 0° C., was added DCM:TFA (1:1) (3 mL). The reaction mixture was warmed to r.t. and stirred for 1 h. The solvents were removed in vacuo. The organic residue was redissolved in DCM. The organic layer was washed with saturated sodium bicarbonate, and dried over MgSO4. The solvent was removed in vacuo to yield IPR-69 (590 mg, 98%) as an off-white solid. $^1H$ NMR (500 MHz, $CDCl_3$) δ 7.86 (s, 1H), 7.49 (s, 1H), 7.38 (d, J=8.3 Hz, 2H), 7.25 (d, J=8.3 Hz, 2H), 6.79 (s, 1H), 3.34-3.27 (m, 2H), 3.26-3.19 (m, 1H), 3.09-2.95 (m, 1H), 2.72 (app t, J=13.2 Hz, 2H), 2.46 (qd, J=13, 9.7, 3.7 Hz, 2H), 2.32 (s, 6H), 1.74 (d, J=15 Hz, 2H), 1.32 (d, J=7 Hz, 6H); $^{13}C$ NMR (125 MHz, $CDCl_3$) δ 161.8, 150.3, 149.1, 138.73, 138.69, 137.8, 137.0, 127.4, 126.2, 126.1, 118.0, 115.8, 46.2, 34.9, 33.9, 30.2, 23.8, 21.4. MS calculated for $C_{26}H_{33}N_4O$ $(M+H)^+$ 417.2649, found 417.2646.

diethyl 2-(benzo[d][1,3]dioxol-5-ylmethylene)malonate (8)—To a solution of diethyl malonate (31.2 mmol, 5.0 g) and piperonal (37.4, 5.61 g) in toluene (80 mL), was added piperidine (3.12 mmol, 0.308 mL) followed by acetic acid (3.12 mmol, 0.179 mL). The reaction was refluxed at 150° C. under Dean-Stark conditions for 24 h. The reaction mixture was purified by flash chromatography (20% EA/Hex) to give an inseparable mixture of 8 and aldehyde (3.83 g, 42%) as a clear oil. TLC Rf=0.31 (20% EA/Hex). $^1H$ NMR showed 8 constituted 86% of the mixture (3.29 g, 36%). $^1H$ NMR (500 MHz, $CDCl_3$) δ 7.61 (s, 1H), 7.01-6.98 (m, 1H), 6.96-6.94 (m, 1H), 6.82-6.78 (m, 1H), 6.00 (s, 2H), 4.36 (q, J=7.1 Hz, 2H), 4.28 (q, J=7.1 Hz, 2H), 1.32 (2t, J=7.2 Hz, 6H); $^{13}C$ NMR (126 MHz, $CDCl_3$) δ 190.2, 166.9, 164.2, 149.8, 148.2, 141.6, 128.5, 126.9, 126.1, 124.0, 108.5, 108.3, 108.3, 106.8, 102.0, 101.6, 61.6, 61.4, 14.1, 13.8. HRMS calculated for $C_{15}H_{17}O_6$ $(M+H)^+$ 293.1020, found 293.1025.

(+) Diethyl 2-(1-(benzo[d][1,3]dioxol-5-yl)-2-phenylethyl)malonate (9)—Under argon, 8 (9.61 mmol, 2.81 g) in dry $Et_2O$ (30 mL) was added slowly via cannula to a suspension of CuCl (0.481 mmol, 48 mg) and benzyl magnesium chloride (11.5 mmol, 5.75 mL) at −78° C. The mixture was stirred while gradually raising the temperature to r.t. overnight. Sat. NH4Cl was added. The aqueous layer was extracted with $Et_2O$ (3×). The combined organic extracts were washed with brine and dried over $MgSO_4$. The crude residue was purified by flash chromatography (10% EA/Hex) to give 9 (2.26 g, 98%) as a yellowish oil. The product was directly used for the following step without further purification. MS calculated for $C_{22}H_{25}O_6$ $(M+H)^+$ 385.1646. found 385.1654

(+) 3-(benzo[d][1,3]dioxol-5-yl)-4-phenylbutanoic acid (10)—To a stirred solution of 9 (5.37 mmol, 2.06 g) in MeOH/H2O (1:1, 40 mL) was added a 10% KOH solution (40 mL) in one portion. The reaction mixture was stirred at r.t. for 24 h. MeOH was removed in vacuo and the water layer was acidified to pH 2 with 6N HCl at 0° C. The precipitate was collected by vacuum filtration. The crude solid was dissolved in p-xylene (30 mL) and refluxed overnight at 170° C. The crude mixture was purified by flash chromatography (10% EA/Hex) to yield 10 (1.42 g, 93%) as a white solid. TLC Rf=0.17 (10% EA/Hex). $^1H$ NMR (500 MHz, $CDCl_3$) δ 7.28-7.14 (m, 3H), 7.09-7.03 (m, 2H), 6.73-6.65 (m, 2H), 6.61-6.55 (m, 1H), 5.92 (s, 2H), 3.38-3.28 (m, 1H), 2.91-2.82 (m, 2H), 2.70-2.54 (m, 2H); $^{13}C$ NMR (125 MHz, $CDCl_3$) δ 177.1, 147.6, 146.2, 139.3, 137.0, 129.2, 128.3, 126.3, 120.6, 108.2, 107.7, 100.9, 43.4, 43.1, 39.9. MS calculated for $C_{17}H_{17}O_4$ $(M+H)^+$ 285.1121, found 285.1116.

(+) 3-(benzo[d][1,3]dioxol-5-yl)-4-phenylbutan-1-ol (11)—10 (4.9 mmol, 1.39 g) in dry THF (50 mL) was added dropwise to a slurry of lithium aluminum hydride (9.8 mmol, 372 mg) in dry THF (30 mL) at 0° C. over 30 min. The reaction mixture was stirred and gradually warmed to r.t. over 4 h. The reaction was cooled again to 0° C. and water was added until evolution of gas ceased. The resultant slurry was filtered over Celite washing with $Et_2O$. THF was removed in vacuo. The crude residue was purified by flash chromatography (30% EA/Hex) to yield 11 (1.14 g, 86%) as a clear oil. TLC Rf=0.27 (30% EA/Hex) $^1H$ NMR (500 MHz, $CDCl_3$) δ 7.25-7.10 (m, 3H), 7.08-7.03 (m, 2H), 6.74-6.66 (m, 2H), 6.59-6.54 (m, 1H), 5.92 (s, 2H), 3.55-3.47 (m, 1H), 3.46-3.38 (m, 1H), 2.99-2.90 (m, 1H), 2.89-2.82 (m, 2H), 1.98-1.88 (m, 1H), 1.85-1.73 (m, 1H); $^{13}C$ NMR (125 MHz, $CDCl_3$) δ 147.6, 145.8, 140.2, 138.1, 129.1, 128.1, 125.9, 120.8, 108.0, 107.6, 100.7, 60.9, 44.1, 43.9, 38.3. MS calculated for $C_{17}H_{19}O_3$ $(M+H)^+$ 271.1329, found 271.1326.

(+) 3-(benzo[d][1,3]dioxol-5-yl)-4-phenylbutanal (12)—To a stirred solution of 11 (4.04 mmol, 1.09 g), triethylamine (20.2 mmol, 2.8 mL), and DMSO (109 mmol, 7.7 mL) in DCM (20 mL), at 0° C., was added $SO_3$.Py (20.2 mmol, 3.21 g) portionwise over 5 min. The reaction mixture was stirred for 2 h and subsequently warmed to r.t. Excess sodium bicarbonate was then added and the mixture stirred until all remaining $SO_3$.Py was consumed. The organic solution was diluted with DCM, washed with brine, dried over MgSO4, and solvent was removed in vacuo. The crude residue was purified by flash chromatography (20% $Et_2O$/Hex) to give 12 (871 mg, 80%) as a yellowish oil. TLC Rf=0.24 (20% Et2O/Hex). $^1H$ NMR (500 MHz, $CDCl_3$) δ 9.59 (s, 1H), 7.29-7.15 (m, 3H), 7.09-7.03 (2H), 6.73-6.65 (m, 2H), 6.63-6.56 (m, 1H), 5.92 (s, 2H), 3.47-3.37 (m, 1H), 2.95-2.80 (m, 2H), 2.70 (d, J=8.1 Hz, 2H); $^{13}C$ NMR (125 MHz, $CDCl_3$) δ 201.5, 147.8, 146.2, 139.2, 137.0, 129.1, 128.3, 126.3, 120.6, 108.2, 107.6, 100.9, 49.1, 43.4, 41.8. MS calculated for $C_{17}H_{15}O_3$ $(M-H)^-$ 267.1027, found 267.1030.

4-(((3-(benzo[d][1,3]dioxol-5-yl)-4-phenylbutyl)amino)methyl)-N,Ndimethylaniline (IPR-1)—Under argon a flask was charged with 12 (36 mg, 0.13 mmol), THF (2 mL), and 4-(dimethylamino)benzylamine dihydrochloride (58 mg, 0.26 mmol). $Na(AcO)_3BH$ (55 mg, 0.26 mmol) was added with stirring at r.t. After 20 h, 1M NaOH (2 mL) was added. The mixture was extracted with Et2O (3×10 mL). The extract was dried over $MgSO_4$ and solvent removed in vacuo. The crude material was purified by column chromatography (2%-5% (10% NH4OH/MeOH)/DCM) to give IPR-1 (13 mg, 25%) as a colorless oil. TLC Rf=0.18 (5% (10% NH4OH/MeOH/DCM). $^1H$ NMR (500 MHz, $CDCl_3$) δ 7.24-7.10 (m, 5H), 7.05-6.98 (m, 2H), 6.70-6.62 (m, 4H), 6.55-6.48 (m, 1H), 5.90 (d, J=5 Hz, 2H), 3.69-3.52 (m, 2H), 2.91 (s, 6H), 2.82 (s, 3H), 2.53-2.45 (m, 2H), 2.00-1.77 (m, 2H); $^{13}C$ NMR (125 MHz, $CDCl_3$) δ 150.0, 147.5, 145.7, 140.1, 138.0, 129.5, 129.1, 128.0, 125.8, 120.8, 112.5, 108.0, 107.6, 100.7, 52.5, 46.4, 45.6, 43.9, 40.6, 34.8; MS calculated for $C_{26}H_{31}N_2O_2$ $(M+H)^+$ 403.2380, found 403.2385.

Example 11

In Vitro Studies for Insights into PK Properties of IPR-69

Inhibition of the hERG channel is undesirable. Checking for hERG blockage is an integral step in the drug discovery cycle. The presently disclosed method is well-suited for high-throughput measurements based on fluorescence polarization (FP) as implemented in the Predictor Assay by Invitrogen (Carlsbad, Calif.). This assay is based on the principle that a fluorescent tracer upon binding to the hERG channel will induce an increase in the FP signal that will diminish when an inhibitor displaces the interaction between the tracer and the hERG channel. Data generated with this assay were shown to correlate well with patch-clamp assays measurements.[38]

FP measurements for IPR-1 and IPR-69 were performed using an EnVision (PerkinElmer) plate reader at an excitation of 540 nm and emission at 573 nm. As shown in FIG. 7A, IPR-1 and its derivative blocked the channel at all three concentrations considered (1, 10 and 25 μM). In fact, these two compounds showed even greater potency than the well-known channel blocker E-4031.[39] IPR-69, on the other hand, exhibited lower levels of hERG blockage. At the highest concentration of 25 μM, which is near its biological activity in tumor cells, 60% blockage is detected.

Another source of toxicity for drugs is cytochrome P450s (CYPs) inhibition. CYPs detoxify harmful compounds and catalyze key reactions in the formation of endogenous compounds such as hormones and steroids.[40] Studies have shown that 90% of drugs are metabolized by at least one of the seven known CYP isoforms (CYP-1A2, 2C9, 2C18, 2C19, 2D6, 2E1 and 3A4). CYP metabolism was measured using a fluorescence-based assay designed by Cohen et al.,[41] recently implemented by Invitrogen (Carlsbad, Calif.).

Compounds IPR-1, IPR-9 and IPR-69 were evaluated for inhibition of CYP2C9. As a positive control, the CYP2C9 inhibitor sulphaphenazole inhibited the metabolism of the fluorescent substrate by approximately 69% at 5 μM (FIG. 7B). IPR-1 and IPR-9 showed little inhibition at 1 μM, but more significant inhibition at concentrations that are comparable to their biological activity. At 25 μM, these compounds inhibit the enzyme by nearly 80%, comparable to the levels seen for sulphaphenazole, suggesting potential toxicity in vivo. IPR-69, on the other hand revealed little inhibition of CYP2C9 (FIG. 7B). Even at 25 μM, only 20% inhibition is detected, comparable to what is observed for FDA approved drugs.[42]

Finally, DNA binding by these three compounds was assessed. DNA binding is often a reflection of non-specificity, which can lead to adverse side effects. The well-established Fluorescent Intercalator Displacement assay by Tse et al.[43] that measures displacement of ethidium bromide, a known intercalator of DNA was used. In this assay, ethidium bromide (EB) bound to the salmon sperm DNA. DNA binding was not strongly affected at the three concentrations of IPR-1, IPR-9, and IPR-69 that were tested. IPR-1 and IPR-9 showed 30% displacement of ethidium bromide, while IPR-69 showed less than 10% displacement at 25 μM (FIG. 7C).

Example 12

In Vivo PK Study of IPR-69

Compound IPR-69 was administered to mice via a single oral gavage of 50 mg/kg using a formulation of 0.5% (w/v) of methylcellulose and 0.1% of tween-20. Blood (20 μL) was taken from the mice at their tails at time intervals of 1, 2, 4, 12, 24, 36, and 48 hours (two time points from each of 22 mice post injection.[44] Blood plasma samples were prepared by (centrifugation) for quantification and HPLC MS/MS analysis. IPR-69 was quantified as shown in FIG. 7D and the resulting in vivo PK parameters are provided in FIG. 7E. IPR-69 was detected in plasma at a maximum level of 40 μM at approximately 5 hours after administration. A half-life was estimated at 2 hours. These parameters suggest that IPR-69 possesses suitable drug-like properties in vivo and sets the stage for further optimization of the potency of the compound.

Example 13

Role of IPR-69 in MDA-MB-231 Metastasis In Vivo

The effect of IPR-69 in blocking metastasis and growth in cell culture, along with its favorable in vivo pharmacokinetic properties prompted evaluation of its effect on metastasis in vivo. TMD-231 cells were inoculated into the mammary fat pad of female NOD/SCID mice. Dosing was initiated at day 18 post implantation. Animals were randomized and treated with vehicle or with IPR-69 by daily oral gavage at a dose of 150 mg/kg (n=11). Tumor volumes were determined by caliper measurements on a twice weekly basis, and calculated according to the formula (α2×β)/2, where α is the shorter and β is the longer of the two dimensions. Tumor volumes were determined by caliper measurements on a weekly basis. The study was conducted over a period of 68 days. The primary tumor in both control and treated mice grew substantially over the course of the study. Tumor volumes reached nearly 965 $mm^3$ for untreated mice. For treated mice, tumor volumes reached an average of 779 $mm^3$ at the end of the study, a 20% reduction (FIG. 8A). Once the tumor volume reached 30 $mm^3$ to 50 $mm^3$, animals were randomized and treated with vehicle alone as control or 150 mg/kg IPR-69 three times a week for 10 weeks by oral gavage. Tumor volumes were determined by caliper measurements obtained weekly. Over the course of the study, several mice were sacrificed to determine whether breast tumor cells had metastasized to the lungs. At the end of the study, control and experimental animals were sacrificed and organs (lungs) were removed and evaluated for the presence of tumors. The number and size of metastasis in two to five fields per sample were calculated. A score of 4+ was given to a sample with highest metastasis index and relative metastasis in other samples are calculated (i.e., 1+, 2+, 3+) by a sample-blinded pathologist. Briefly, percentage of staining was categorized as "0" if there was no nuclear/cytoplasmic expression, "1" for up to 10% positive tumor nuclei/cells, "2" for 11-20% and until a maximum score of "10". Intensity was scored as "1+," "2+," and "3+" for weak, moderate and strong staining respectively. In the untreated mice, 9 out of 11 mice had metastatic foci in the lungs (Score=0). In contrast, only 3 out of 11 treated mice showed signs of metastatic lesions. The extent of metastasis in treated versus untreated also was different. Fewer of the treated mice developed substantial metastasis with a score >2. For example, 5 of the untreated mice exhibited increased metastatic lesions (score >2), compared with only 3 of the treated mice (FIG. 8B). Finally, more of the untreated mice developed metastatic lesions with a score of 4 or greater (FIG. 8B). An illustration of the extent of metastasis to the lungs is shown in FIG. 8C with H&E staining images for control and treated mice.

Example 14

Discussion

Throughout the metastatic process, malignant cells unleash a series of proteases that systematically degrade components of the ECM, not only to eventually gain access to the vasculature (extravasation), but also following attachment to new sites to create new colonies (intravasation). When a distant colony is established during metastasis, a constant supply of nutrients is needed to sustain the level of growth required for the tumor to establish itself and begin the process of metastasis anew. This process, known as angiogenesis, also requires the contribution of proteases. The urokinase receptor (uPAR) plays an important role in these processes, not only by anchoring proteases at the cell surface, but also by engaging other receptors at the cell surface. Using virtual screening, a chemical library of nearly 300,000 molecules was screened for compounds that bind to uPAR. Active compounds were identified by computation and were then shown experimentally to bind directly to uPAR. Cellular studies revealed that two of these compounds, IPR-9 and IPR-69, blocked invasion, migration, adhesion of MDA-MB-231 breast cancer cells in cell culture. Both these compounds also impaired angiogenesis in a tube formation assays using HUVECs with an $IC_{50}$ nearly an order of magnitude better ($IC_{50}$=3 μM) than those observed in the invasion studies. Gel zymography analysis revealed that the compounds impaired MMP-9 activity in a concentration-dependent manner with $IC_{50}$ that are comparable to those measured in the invasion studies. This observation was encouraging, since previous studies have shown that uPA promotes degradation of the ECM through activation of MMP-9 activity. IPR-9 and IPR-69 inhibited MDA-MB-231 proliferation ($IC_{50}$=6 μM and 17 μM, respectively), and subsequent flow cytometry analysis with annexin V staining revealed that both induced apoptosis, while IPR-9 also caused significant necrosis. Signaling studies showed that both compounds impaired MAPK phosphorylation, but IPR-1 was more potent. IPR-1 did not show any effect on FAK and Src signaling, suggesting that these compounds are unlikely affecting integrin-mediated signaling. Past studies have shown that uPAR can enhance signaling through integrins. The lack of effect of IPR-1 on integrin signaling suggests that the uPA binding site is unlikely contributing to integrin signaling and that other sites on the receptor, such as the vitronectin binding site, are responsible for interaction with integrins. A series of biochemical assays that included DNA binding, cytochrome P450 inhibition, and hERG $K^+$ channel blockage provided insight into the drug-likeness properties of the compounds. IPR-69 exhibited the most favorable properties, showing no DNA binding, little inhibition of CYP2C9, and lower levels of hERG channel blockage. In contrast, IPR-1 and its derivative IPR-9, showed significant impairment of CYP2C9 activity and even greater hERG $K^+$ channel blockage than the well-known channel blocker E-4031. These results suggested a focus on IPR-69 and assess is PK properties in vivo. The compound was orally bioavailable, reaching concentrations of up to 40 μM with half-life of approximately 2 hours when administered. The compound was well tolerated at doses as high as 150 mg/kg. These promising results prompted efficacy studies to evaluate its anti-metastatic effect in vivo using a triple-negative TMD-231 (MDA-MB-231 variant) implanted in breast mammary fat pads. It was interesting that treated mice developed primary tumors that were on average 20% lower in size than untreated mice. In addition, the treated mice showed less metastasis to the lungs when compared with the untreated group. It is likely that some of the anti-cancer effects of IPR-69 are enhanced by off targets. Given the effects of IPR-69 on invasion and angiogenesis, the possibility that the compound may bind and inhibit MMP-9 or VEGFR2, key mediators of invasion and angiogenesis was explored. The compound was docked to the active site of MMP-9 and VEGFR2 (PDB codes 1GKC and 3EWH, respectively) using the Vina docking program. The resulting complexes along with the complex of IPR-69 bound to uPAR were scored with the X-score scoring function, which we have recently shown to perform best in rank-ordering complexes. The resulting scores were −9.2, −9.7, and −9.7 for uPAR, MMP-9 and VEGFR2, respectively. While conclusive evidence will have to be obtained from biochemical studies, the similarity of these scores suggests that either MMP-9 or VEGFR2 may also be targets of the compound. Cancer is a systems biology disease that involves multiple signaling pathways and compounds with polypharmacology that target more than one pathway may lead to cancer therapeutics with greater efficacy. Therefore, off-targets that enhance the anticancer properties of a compound may be welcome, as long as they do not cause undue toxicity. IPR-69 seems to be well tolerated even at concentrations of 150 mg/kg and caused little toxicity, suggesting that off-targets are unlikely causing toxicity. The promising PK properties and the encouraging effects on tumor growth and metastasis in vivo suggest IPR-69 as an excellent platform upon which to develop derivatives with greater efficacy in vivo.

Example 15

$IC_{50}$ Values of Compounds

TABLE 1

| Compounds | $IC_{50}$ (μM) | $K_i$ (μM) |
|---|---|---|
| IPR-008 | 33.6 | 10.2 |
| IPR-009 | 24.4 | 7.4 |
| IPR-021 | 58.7 | 17.9 |
| IPR-022 | 24.2 | 7.3 |
| IPR-89 | 33 | 10.04 |
| IPR-108 | 42 | 12.8 |
| IPR-361 | 47 | 14.3 |
| IPR-380 | 18 | 5.4 |
| IPR-737 | 30 | 9.12 |
| IPR-949 | 9.8 | 2.9 |
| IPR-968 | 34 | 10.3 |

Example 16

Representative Derivatives

Scheme 3

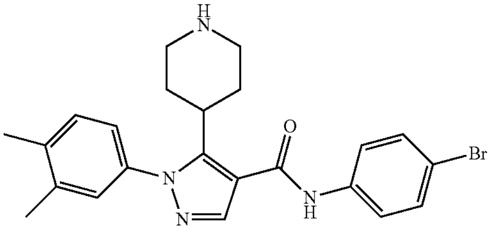

IPR-82

-continued
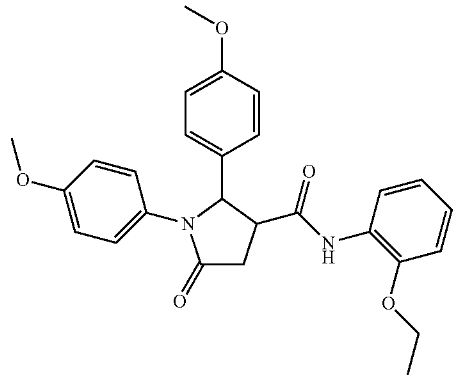
IPR-99
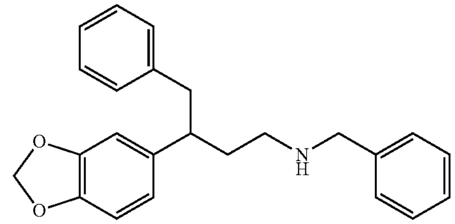
IPR-21
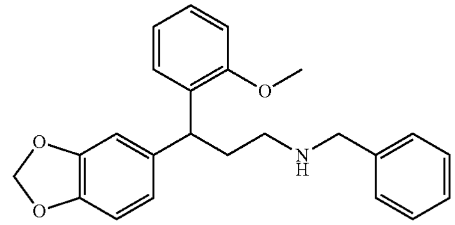
IPR-22
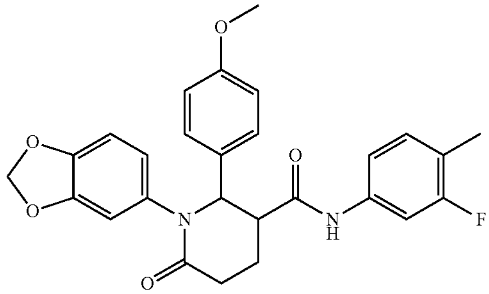
IPR-105
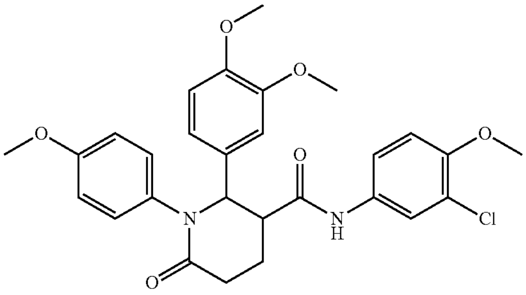
IPR-108
-continued
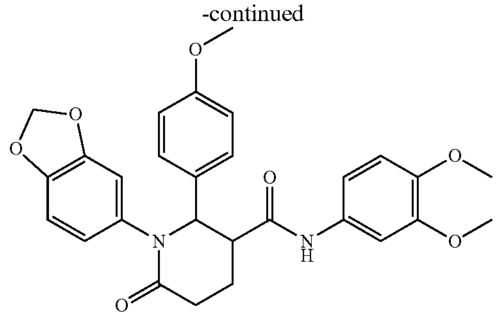
Example 17
Synthesis of Compounds 34, 35, 36a
Scheme 4
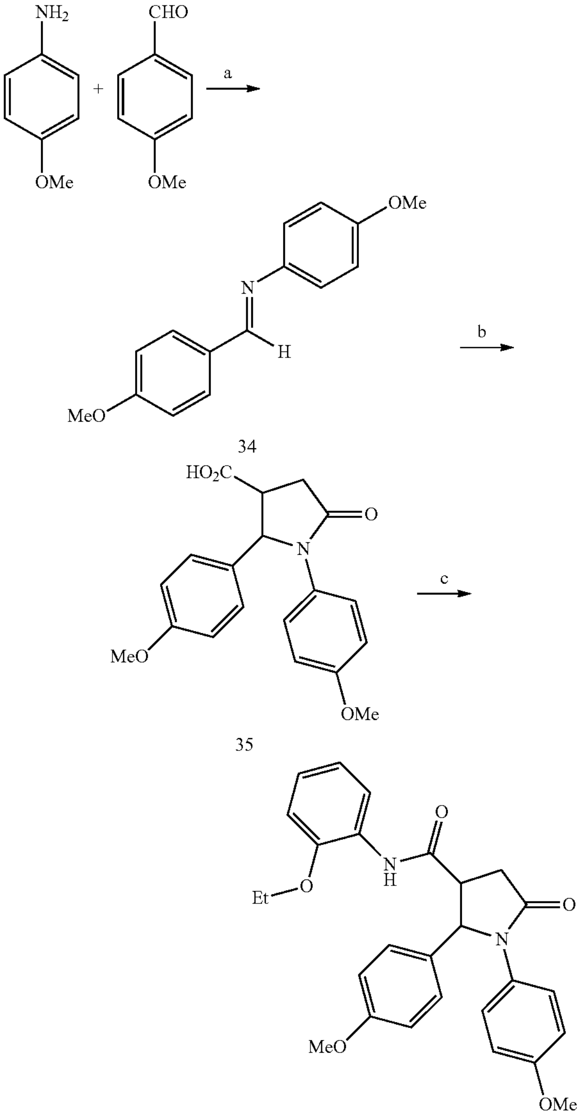
34
35
36a Reagents and conditions in Scheme 4: a) anhydrous $MgSO_4$, DCM, r.t. b) succinic anhydride, xylenes, reflux c) DMAP, DCC, o-phenetidine, DCM, 0° C. to r.t.

Example 18

Synthesis of Compounds 31, 32, 33a

Scheme 5

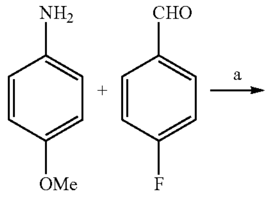

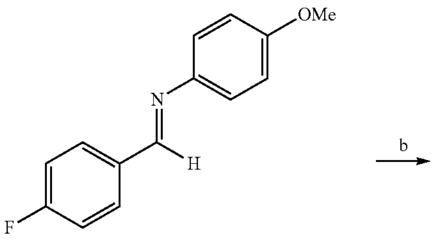

31

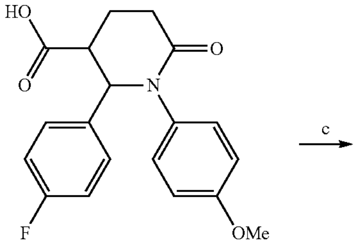

32

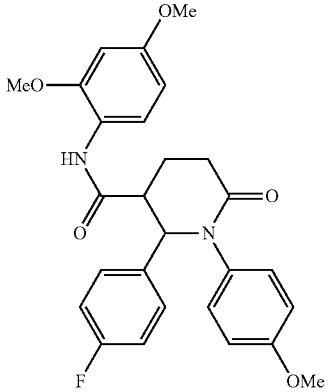

33a

Reagents and conditions in Scheme 5: a) anhydrous $MgSO_4$, DCM, r.t. b) glutaric anhydride, xylenes, reflux c) EDC, HOBT, 2,4-dimethoxyaniline, DCM, 0° C. to r.t.

Example 19

Synthesis of IPR-993 from IPR-69

Scheme 6

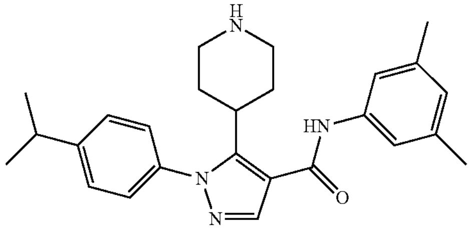

IPR-69

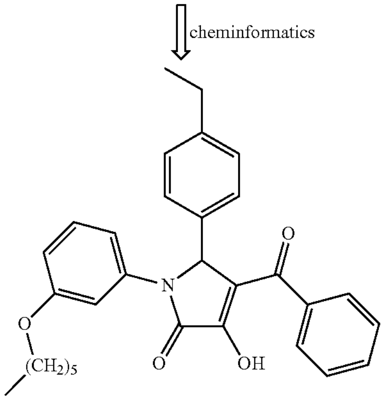

IPR-993

Example 20

Effect of Compounds on Cell Inhibition, Viability, and Invasion

Cellular assays were used to characterize compounds that are derivatives of IPR-1, IPR-69, IPR-99 and IPR-108. Fluorescence polarization for 393 compounds was performed. Compounds were screened against uPAR and AE147-10 FAM peptide at 50 μM (FIGS. 9A, 9B). An MTT assay was performed in MDA-MB-231 cells using 50 μM of each compound (FIGS. 10A; IPR-69/81 derivatives: left cluster; IPR-84/108 derivatives: middle cluster; IPR-99 derivatives: right cluster, 10B). Some of these compounds were further tested for the ability to inhibit cell invasion and cell migration in MDA-MB-231 cells (FIGS. 11A, 11B).

Example 21

Effect of IPR-737

Some of the compounds of the presently disclosed subject matter were tested in a MTT assay using a human pancreas carcinoma cell line PANC-1 (FIG. 12A). The results from this assay showed inhibition of cell viability for some of the compounds (FIG. 12B). One of these compounds, IPR-737, was further tested in a MTT assay using MDA-MB-231, AsPC-1 (human pancreas adenocarcinoma cell line), and PANC-1 cells. The results of this assay showed that IPR-737 inhibited cell proliferation in the breast cancer cells as well as in the pancreatic cancer cell lines (FIGS. 12A, 12B).

FIGS. 13A, 13B, 13C, 13D show the inhibition of cell invasion by some of the compounds of the presently disclosed subject matter in MDA-MB-231 cells (FIG. 13A). The IPR-737 compound was further tested in a MMP-9 zymography assay in MDA-MB-231 cells (FIG. 13C). IPR-737 demonstrated impairment of matrix metalloproteinase (MMP-9) activity in the gelatin zymography assay suggesting direct involvement in blocking degradation of the ECM. Testing of the IPR-737 compound in a MDA-MB-231 adhesion assay showed that the IPR-737 compound was capable of inhibiting breast cancer cells (FIG. 13B). At a concentration of 50 μM, the IPR-737 compound was significantly more active in this assay than the IPR-81 and IPR-69 compounds. A cell migration assay demonstrated that the IPR-737 compound was capable of inhibiting cell migration as compared to the control (FIG. 13D).

FIG. 14 illustrates the results from a MMP-9 zymography assay in MDA-MB-231 cells. Increasing concentrations of the IPR-737 compound resulted in increasing inhibition of MMP-9. The IPR-69 compound showed some inhibition of MMP-9 in this assay and the IPR-81 compound showed significantly more inhibition.

FIGS. 15A, 15B, 15C, 15D, 15E show the effect of different concentrations of a compound of the presently disclosed subject matter in MDA-MB-231 cells with different types of the urokinase receptor. This illustrates that different kinds of urokinase receptors are affected by the compounds of the presently disclosed subject matter.

Example 22

Effect of IPR-993

Some of the compounds of the presently disclosed subject matter were tested in a uPAR microtiter binding assay (ELISA) in which uPAR antibody was used. The IPR derivatives were tested in concentrations from 100 μM to 0.41 μM in 1×PBS with 0.01% Triton in duplicates. 75 nM of uPAR was added to each assay. Most of the compounds showed a significant inhibition in the assay (FIG. 16).

IPR-993 was tested in a PANC-1 invasion assay and showed inhibition of activity with increasing concentrations of compound (FIGS. 17A, 17B). IPR-993 showed little decrease in cell viability in the PANC-1 invasion assay (FIG. 18).

IPR-993 was further tested in a MDA-MB-231 invasion assay and showed inhibition of activity with increasing concentrations of compound (FIGS. 19A, 19B). A MTT assay using either MDA-MB-231 cells or PANC-1 cells showed that the IPR-993 compound inhibited cell viability with both breast cancer cells and pancreatic cancer cells (FIGS. 20A, 20B). These results show that IPR-993 is active in different kinds of cancer cell lines.

IPR-993 did not appear to demonstrate impairment of MMP-9 activity in a gelatin zymography assay suggesting that there may not be direct involvement of IPR-993 in blocking degradation of the ECM (FIGS. 21A, 21B).

IPR-993 showed some activity in a MDA-MB-231 adhesion assay suggesting that the IPR-993 compound is capable of inhibiting cell adhesion (FIG. 22).

In light of the previously reported role of uPAR in signaling, the effect of IPR-993, IPR-737, IPR-81 and IPR-69 on signaling was studied by Western blot analysis (FIG. 23). A concentration-dependent study was carried out for IPR-737. There did not seem to be much of an effect of the compounds on different signaling molecules in this assay.

REFERENCES

1. Sporn, M. B. The war on cancer. *Lancet* 1996, 347, 1377-81.
2. Wei, Y.; Lukashev, M.; Simon, D. I.; Bodary, S. C.; Rosenberg, S.; Doyle, M. V.; Chapman, H. A. Regulation of integrin function by the urokinase receptor. *Science* 1996, 273, 1551-1555.
3. Kiyan, J.; Kiyan, R.; Haller, H.; Dumler, I. Urokinase-induced signaling in human vascular smooth muscle cells is mediated by PDGFR-beta. *Embo J* 2005, 24, 1787-97.
4. Liu, D.; Aguirre Ghiso, J.; Estrada, Y.; Ossowski, L. EGFR is a transducer of the urokinase receptor initiated signal that is required for in vivo growth of a human carcinoma. *Cancer Cell* 2002, 1, 445-57.
5. Shapiro, R. L.; Duquette, J. G.; Nunes, I.; Roses, D. F.; Harris, M. N.; Wilson, E. L.; Rifkin, D. B. Urokinase-type plasminogen activator-deficient mice are predisposed to staphylococcal botryomycosis, pleuritis, and effacement of lymphoid follicles. *Am J Pathol* 1997, 150, 359-69.
6. Kirchheimer, J. C.; Wojta, J.; Christ, G.; Binder, B. R. Proliferation of a human epidermal tumor cell line stimulated by urokinase. *Faseb J* 1987, 1, 125-8.
7. Kirchheimer, J. C.; Wojta, J.; Christ, G.; Binder, B. R. Functional inhibition of endogenously produced urokinase decreases cell proliferation in a human melanoma cell line. *Proc Natl Acad Sci USA* 1989, 86, 5424-8.
8. Andreasen, P. A.; Kjoller, L.; Christensen, L.; Duffy, M. J. The urokinase-type plasminogen activator system in cancer metastasis: A review. *International Journal of Cancer* 1997, 72, 1-22.
9. Mignatti, P.; Rifkin, D. B. Plasminogen activators and matrix metalloproteinases in angiogenesis. *Enzyme Protein* 1996, 49, 117-37.
10. Rabbani, S. A.; Mazar, A. P. The role of the plasminogen activation system in angiogenesis and metastasis. *Surg Oncol Clin N Am* 2001, 10, 393-415, x.
11. Kim, J.; Yu, W.; Kovalski, K.; Ossowski, L. Requirement for specific proteases in cancer cell intravasation as revealed by a novel semiquantitative PCR-based assay. *Cell* 1998, 94, 353-62.
12. Berge. S. M.; Bighley, L. D.; Monkhouse, D. C. Pharmaceutical Salts. *J Pharm Sci* 1977, 66, 1-19.
13. Sidman, K. R.; Steber, W. D.; Schwope, A. D.; Schnaper, G. R. Control release of macromolecules and pharmaceuticals from synthetic polypeptides based on glutamic acid *Biopolymers* 1983, 22, 547-56.
14. Langer, R; Brem, H; Tapper, D. Biocompatibility of polymeric delivery systems for macromolecules. *J Biomed Mater Res* 1981, 15, 267-77.
15. Langer, R. Controlled release of macromolecules. *Chem Tech* 1982, 12, 98-105.
16. Eppstein, D. A.; Marsh, Y. V.; van der Pas, M.; Felgner, P. L.; Schreiber, A. B. Biological activity of liposome-encapsulated murine interferon gamma is mediated by a cell membrane receptor. *Proc Natl Acad Sci USA* 1985, 82, 3688-92.
17. Hwang, K. J.; Luk, K. F.; Beaumier, P. L. Hepatic uptake and degradation of unilamellar sphingomyelin/cholesterol liposomes: a kinetic study. *Proc Natl Acad Sci USA* 1980, 77, 4030-34.
18. Greene, T. W.; Wuts, P. G. M. Protective Groups in Organic Synthesis, 3rd ed. John Wiley & Sons 1999.
19. Dorfleutner, A.; Stehlik, C.; Zhang, J.; Gallick, G. E.; Flynn, D. C. AFAP-110 is required for actin stress fiber formation and cell adhesion in MDA-MB-231 breast cancer cells. *J Cell Physiol* 2007, 213, 740-749.
20. Chavakis, T.; Kanse, S. M.; Lupu, F.; Hammes, H. P.; Muller-Esterl, W.; Pixley, R. A.; Colman, R. W.; Preissner, K. T. Different mechanisms define the antiadhesive function of high molecular weight kininogen in integrin- and urokinase receptor dependent interactions. *Blood* 2000, 96, 514-22.

21. Ingram, D. A.; Mead, L. E.; Tanaka, H.; Meade, V.; Fenoglio, A.; Morten, K.; Pollok, K.; Ferkowicz, M. J.; Gilley, D.; Yoder, M. C. Identification of a novel hierarchy of endothelial progenitor cells using human peripheral and umbilical cord blood. *Blood* 2004, 104, 2752-60.
22. Hochreiter, A. E.; Xiao, H.; Goldblatt, E. M.; Gryaznov, S. M.; Miller, K. D.; Badve, S.; Sledge, G. W.; Herbert, B. S. Telomerase template antagonist GRN163L disrupts telomere maintenance, tumor growth, and metastasis of breast cancer. *Clin Cancer Res* 2006, 12, 3184-92.
23. Eldridge, M. D.; Murray, C. W.; Auton, T. R.; Paolini, G. V.; Mee, R. P. Empirical scoring functions: I. The development of a fast empirical scoring function to estimate the binding affinity of ligands in receptor complexes. *J Comput Aided Mol Des* 1997, 11, 425-45.
24. Jones, G.; Willett, P.; Glen, R. C.; Leach, A. R.; Taylor, R. Development and validation of a genetic algorithm for flexible docking. *J Mol Biol* 1997, 267, 727-48.
25. Huey, R.; Morris, G. M.; Olson, A. J.; Goodsell, D. S. A semiempirical free energy force field with charge-based desolvation. *Journal of Computational Chemistry* 2007, 28, 1145-1152.
26. Huang, N.; Kalyanaraman, C.; Irwin, J. J.; Jacobson, M. P. Physics-based scoring of protein-ligand complexes: enrichment of known inhibitors in large-scale virtual screening. *J Chem Inf Model* 2006, 46, 243-53.
27. Huai, Q.; Zhou, A.; Lin, L.; Mazar, A. P.; Parry, G. C.; Callahan, J.; Shaw, D. E.; Furie, B.; Furie, B. C.; Huang, M. Crystal structures of two human vitronectin, urokinase and urokinase receptor complexes. *Nat Struct Mol Biol* 2008, 15, 422-3.
28. Chen, H. C. Boyden chamber assay. *Methods Mol Biol* 2005, 294, 15-22.
29. Khanna, M.; Chelladurai, B.; Gavini, A.; Li, L.; Shao, M.; Courtney, D.; Turchi, J. J.; Matei, D.; Meroueh, S. Targeting ovarian tumor cell adhesion mediated by tissue transglutaminase. *Mol Cancer Ther* 2011, 10, 626-36.
30. Simon, D. I.; Wei, Y.; Zhang, L.; Rao, N. K.; Xu, H.; Chen, Z. P.; Liu, Q. M.; Rosenberg, S.; Chapman, H. A. Identification of a urokinase receptor-integrin interaction site—Promiscuous regulator of integrin function. *Journal of Biological Chemistry* 2000, 275, 10228-10234.
31. Wei, Y.; Eble, J. A.; Wang, Z. M.; Kreidberg, J. A.; Chapman, H. A. Urokinase receptors promote beta 1 integrin function through interactions with integrin alpha 3 beta 1. *Molecular Biology of the Cell* 2001, 12, 2975-2986.
32. Wei, Y.; Tang, C. H.; Kim, Y.; Robillard, L.; Zhang, F.; Kugler, M. C.; Chapman, H. A. Urokinase receptors are required for alpha 5 beta 1 integrin-mediated signaling in tumor cells. *J Biol Chem* 2007, 282, 3929-39.
33. Folkman, J. Angiogenesis in Cancer, Vascular, Rheumatoid and Other Disease. *Nature Medicine* 1995, 1, 27-31.
34. Brown, S.; Meroueh, S. O.; Fridman, R.; Mobashery, S. Quest for selectivity in inhibition of matrix metalloproteinases. *Curr Top Med Chem* 2004, 4, 1227-38.
35. Wang, A. X.; Xie, Q.; Lane, B.; Mollison, K. W.; Hsieh, G. C.; Marsh, K.; Sheets, M. P.; Luly, J. R.; Coghlan, M. J. Synthesis and immunosuppressant activity of pyrazole carboxamides. *Bioorg Med Chem Lett* 1998, 8, 2787-92.
36. Bashford, K. E.; Burton, M. B.; Cameron, S.; Cooper, A. L.; Hogg, R. D.; Kane, P. D.; MacManus, D. A.; Matrunola, C. A.; Moody, C. J.; Robertson, A. A. B.; Warne, M. R. The Bohlmann-Rahtz route to functionalised pyridine scaffolds and their use in library synthesis. *Tetrahedron Letters* 2003, 44, 1627-1629.
37. Clay, R. J.; Collom, T. A.; Karrick, G. L.; Wemple, J. A Safe, Economical Method for the Preparation of Beta-Oxo Esters. *Synthesis-Stuttgart* 1993, 290-292.
38. Piper, D. R.; Duff, S. R.; Eliason, H. C.; Frazee, W. J.; Frey, E. A.; Fuerstenau-Sharp, M.; Jachec, C.; Marks, B. D.; Pollok, B. A.; Shekhani, M. S.; Thompson, D. V.; Whitney, P.; Vogel, K. W.; Hess, S. D. Development of the predictor HERG fluorescence polarization assay using a membrane protein enrichment approach. *Assay Drug Dev Technol* 2008, 6, 213-23.
39. Kim, I.; Boyle, K. M.; Carroll, J. L. Postnatal development of E-4031-sensitive potassium current in rat carotid chemoreceptor cells. *J Appl Physiol* 2005, 98, 1469-77.
40. Guengerich, F. P. Common and uncommon cytochrome P450 reactions related to metabolism and chemical toxicity. *Chem Res Toxicol* 2001, 14, 611-50.
41. Cohen, L. H.; Remley, M. J.; Raunig, D.; Vaz, A. D. In vitro drug interactions of cytochrome p450: an evaluation of fluorogenic to conventional substrates. *Drug Metab Dispos* 2003, 31, 1005-15.
42. Li, L.; Li, J.; Khanna, M.; Jo, I.; Baird, J. P.; Meroueh, S. O. Docking to Erlotinib Off-Targets Leads to Inhibitors of Lung Cancer Cell Proliferation with Suitable Pharmacokinetics. *ACS Med. Chem. Lett.* 2010, 1, 229-233.
43. Tse, W. C.; Boger, D. L. A fluorescent intercalator displacement assay for establishing DNA binding selectivity and affinity. *Curr Protoc Nucleic Acid Chem* 2005, Chapter 8, Unit 8 5.
44. Bateman, K. P.; Castonguay, G.; Xu, L.; Rowland, S.; Nicoll-Griffith, D. A.; Kelly, N.; Chan, C. C. Reduction of animal usage by serial bleeding of mice for pharmacokinetic studies: application of robotic sample preparation and fast liquid chromatography-mass spectrometry. *J Chromatogr B Biomed Sci Appl* 2001, 754, 245-51.
45. Cairns, R. A.; Khokha, R.; Hill, R. P. Molecular mechanisms of tumor invasion and metastasis: an integrated view. *Curr Mol Med* 2003, 3, 659-71.
46. Zuiderweg, E. R.; Fesik, S. W. Heteronuclear three-dimensional NMR spectroscopy of the inflammatory protein C5a. *Biochemistry* 1989, 28, 2387-91.
47. EP 133,988A.
48. U.S. Pat. No. 4,485,045.
49. U.S. Pat. No. 4,544,545.
50. EP 102,324A.
51. U.S. Pat. No. 6,258,812
52. US 2003/0105091
53. WO 01/37820
54. U.S. Pat. No. 6,235,764
55. WO 01/32651
56. U.S. Pat. No. 6,630,500
57. U.S. Pat. No. 6,515,004
58. U.S. Pat. No. 6,713,485
59. U.S. Pat. No. 5,521,184
60. U.S. Pat. No. 5,770,599
61. U.S. Pat. No. 5,747,498
62. WO 02/68406
63. WO 02/66470
64. WO 02/55501
65. WO 04/05279
66. WO 04/07481
67. WO 04/07458
68. WO 04/09784
69. WO 02/59110
70. WO 99/45009
71. WO 00/59509

72. WO 99/61422
73. U.S. Pat. No. 5,990,141
74. WO 00/12089
75. WO 00/02871
76. U.S. Patent Application Publication No. 2003/0162712
77. U.S. Pat. No. 6,413,932
78. Wiley, U.S. Pat. No. 6,727,225
79. Fanslow et al., U.S. Patent Application Publication No. 2002/0042368
80. U.S. Pat. No. 5,981,245
81. U.S. Pat. No. 5,728,813
82. U.S. Pat. No. 5,969,110
83. U.S. Pat. No. 6,596,852
84. U.S. Pat. No. 6,232,447
85. U.S. Pat. No. 6,057,124 and patent family members thereof.
86. Merck KGaA, Germany, EPO 770622
87. Celgene, USA, U.S. Pat. No. 5,712,291
88. Arriva, USA, U.S. Pat. No. 5,892,112
89. Pfizer, USA, U.S. Pat. No. 5,792,783
90. Fujisawa, Japan, JP 02233610
91. RepliGen, USA, EP 407122
92. U.S. Pat. No. 3,773,919
93. EP 58,481

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Although the foregoing subject matter has been described in some detail by way of illustration and example for purposes of clarity of understanding, it will be understood by those skilled in the art that certain changes and modifications can be practiced within the scope of the appended claims.

While the present invention has been disclosed with references to certain embodiments, numerous modification, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A method for inhibiting binding of urokinase-type plasminogen activator to a urokinase receptor in a subject comprising administering to the subject a therapeutically effective amount of a composition comprising a compound of Formula (I), (II), (III), or (IV):

Formula (I)

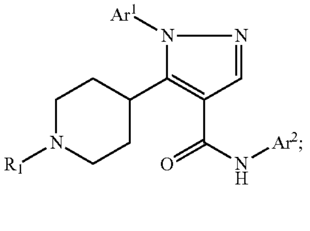

-continued

Formula (II)

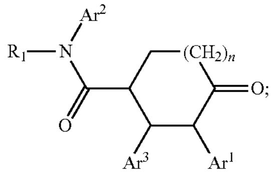

Formula (III)

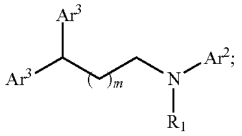

Formula (IV)

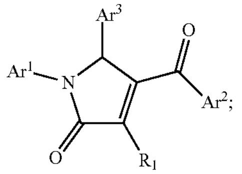

or a pharmaceutically acceptable salt of Formula (I), (II), (III), or (IV);

wherein:

n is an integer selected from the group consisting of 0 and 1;

m is an integer selected from the group consisting of 1, 2, 3, 4, 5, 6, 7, and 8;

$Ar^1$, $Ar^2$, and $Ar^3$ are each independently selected from the group consisting of substituted or unsubstituted cycloalkyl, substituted or unsubstituted cycloheteroalkyl, substituted or unsubstituted aryl, substituted or unsubstituted arylalkyl, substituted or unsubstituted heteroarylalkyl, and substituted or unsubstituted fused ring cycloalkyl or cycloheteroalkyl systems, substituted or unsubstituted fused ring aryl or heteroaryl systems, and substituted or unsubstituted fused ring cycloalkyl or cycloheteroalkyl/aryl or heteroaryl systems; each $R_1$ is independently selected from the group consisting of H, alkyl, cycloalkyl, and hydroxyl;

wherein the compound binds to a urokinase receptor (uPAR); and wherein the subject has cancer.

2. The method of claim 1, wherein the compound is a compound of Formula (I) or a pharmaceutically acceptable salt of Formula (I), wherein $Ar^1$ is selected from the group consisting of 4-isopropylphenyl and 3,4-dimethylphenyl; and $Ar^2$ is selected from the group consisting of 3,5-dimethylphenyl; 2-aminophenethylalcohol; 2-amino-3-methylbenzylalcohol; 3'-aminoacetanilide; 3-aminophenol; 4-amino-2,5-dimethylphenol; 2-aminobenzylalcohol; 2'-aminoacetanilide; 8-aminoquinoline; 3-methoxy-5-trifluoromethylbenzyl; 5-methoxy-2-methylbenzyl; 2-benzyloxy; 3-methylbenzyl; 2-(p-tolyl)ethyl; 3-fluorophenethyl; 2-fluorophenethyl; 4-fluorophenethyl; 4-isopropylbenzyl; 4-propylbenzyl; 4-tert-butylbenzyl; 4-bromophenylbenzyl; 5-chloro-2-methoxybenzyl; 4-methoxy-2-methylbenzyl; and 2,4-dimethylbenzyl.

3. The method of claim 2, wherein the compound of Formula (I) has the following structure:

Formula (V)

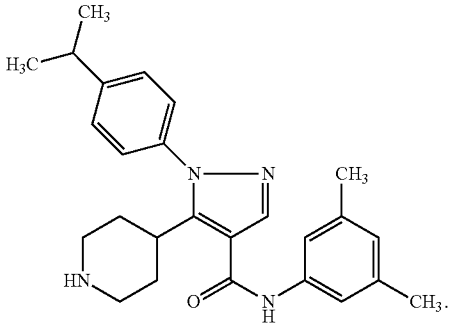

4. The method of claim 1, wherein the compound is a compound of Formula (II) and:

n=0;

$Ar^1$ is 4-methoxyphenyl;

$Ar^2$ is 2-ethoxylphenyl; and $Ar^3$ is 4-methoxyphenyl.

5. The method of claim 4, wherein the compound has the following structure:

Formula (VI)

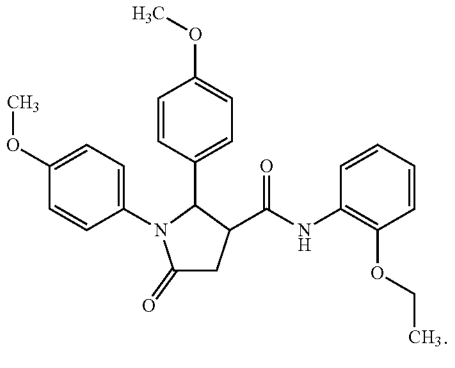

6. The method of claim 1, wherein the compound is a compound of Formula (II) and;

n=1;

$Ar^1$ is selected from the group consisting of benzo[d][1,3]dioxol-5-yl, 3-chloro-4-methoxyphenyl, and 4-methoxyphenyl;

$Ar^2$ is selected from the group consisting of 3,4-dimethoxyphenyl, 3-fluoro-4-methylphenyl, and 2,4-dimethoxyphenyl; and $Ar^3$ is 4-methoxyphenyl and 4-fluorophenyl.

7. The method of claim 6, wherein the compound of Formula (II) is selected from the group consisting of:

Formula (VII)

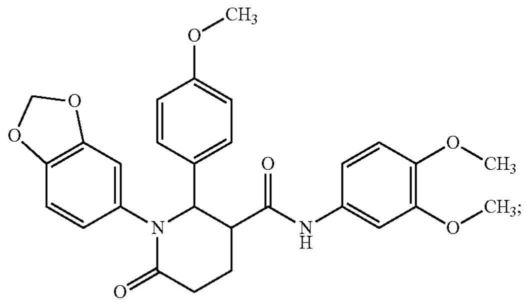

Formula (VIII)

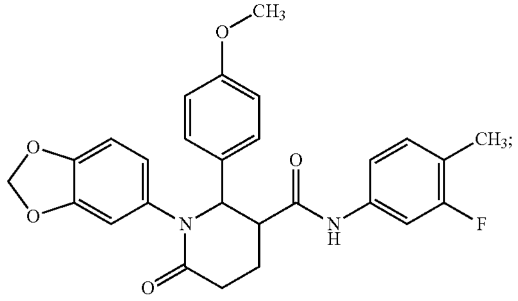

Formula (XI)

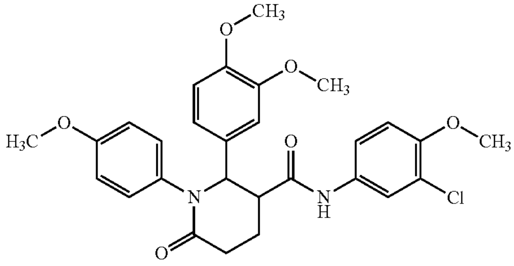

and

Formula (X)

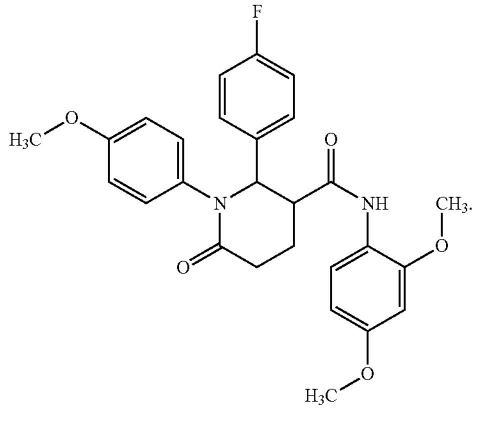

8. The method of claim 1, wherein the compound is a compound of Formula (III) and:

$Ar^1$ is benzo[d][1,3]dioxol-5-yl;

$Ar^2$ is benzyl; and $Ar^3$ is selected from the group consisting of benzyl and 2-methoxyphenyl.

9. The method of claim 8, wherein the compound of Formula (III) is selected from the group consisting of:

Formula (XI)

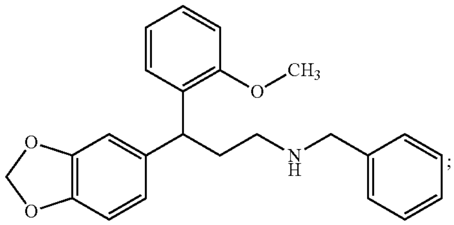

; and

Formula (XII)

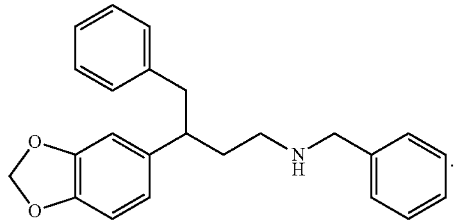

10. The method of claim 1, wherein the compound is a compound of Formula (IV) and has the following structure:

Formula (XIII)

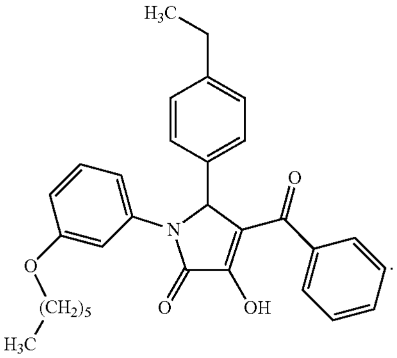

11. The method of claim 1, wherein the cancer comprises breast cancer.

12. The method of claim 1, wherein the cancer comprises pancreatic cancer.

13. A method for treating a cancer in a subject, the method comprising administering to the subject a therapeutically effective amount of a composition comprising a compound of Formula (I):

Formula (I)

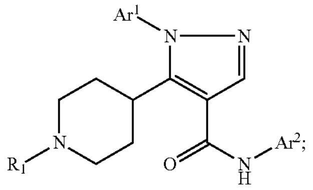

or a pharmaceutically acceptable salt thereof, wherein:

$Ar^1$ is selected from the group consisting of 4-isopropylphenyl and 3,4-dimethylphenyl; and $Ar^2$ is selected from the group consisting of 3,5-dimethylphenyl; 2-aminophenethylalcohol; 2-amino-3-methylbenzylalcohol; 3'-aminoacetanilide; 3-aminophenol; 4-amino-2,5-dimethylphenol; 2-aminobenzylalcohol; 2'-aminoacetanilide; 8-aminoquinoline; 3-methoxy-5-trifluoromethylbenzyl; 5-methoxy-2-methylbenzyl; 2-benzyloxy; 3-methylbenzyl; 2-(p-tolyl)ethyl; 3-fluorophenethyl; 2-fluorophenethyl; 4-fluorophenethyl; 4-isopropylbenzyl; 4-propylbenzyl; 4-tert-butylbenzyl; 4-bromophenylbenzyl; 5-chloro-2-methoxybenzyl; 4-methoxy-2-methylbenzyl; and 2,4-dimethylbenzyl; and wherein the compound of Formula (I) or the pharmaceutically acceptable salt thereof binds to a urokinase receptor (uPAR); and wherein the cancer is selected from the group consisting of: breast cancer and pancreatic cancer.

14. The method of claim 13, wherein the therapeutically effective amount of the composition inhibits invasion and/or metastasis of the cancer in the subject.

15. The method of claim 1, wherein the compound has the following structure:

Formula (XIV)

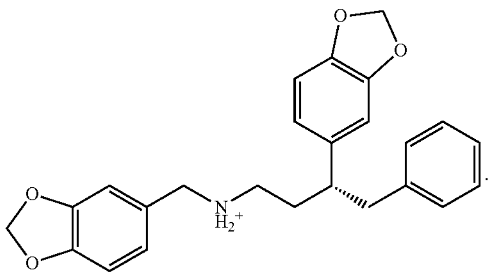

IPR-1

16. The method of claim 1, wherein the compound has the following structure:

Formula (XV)

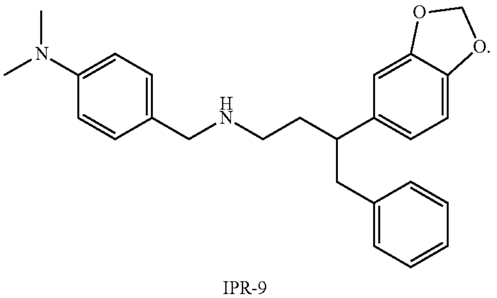

IPR-9

17. The method of claim 1, wherein the therapeutically effective amount of the composition is administered to the subject in combination with an additional anti-angiogenic agent to the subject.

18. The method of claim 13, the compound has the following structure:

Formula (V)

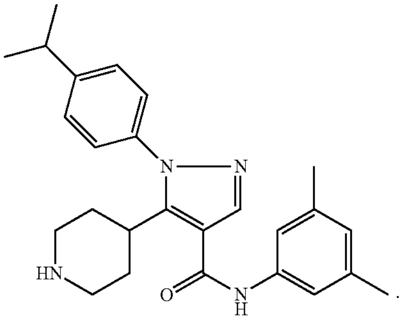

IPR-69

19. The method of claim 13, the compound has the following structure:

Formula (XIII)

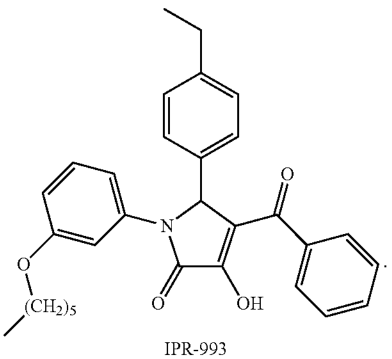

IPR-993

20. The method of claim 13, wherein the therapeutically effective amount of the composition is administered to the subject orally.

21. The method of claim 13, wherein the therapeutically effective amount of the composition is administered to the subject in combination with an additional anti-angiogenic agent to the subject.

22. The method of claim 13, wherein the therapeutically effective amount of the compound is administered to the subject at a daily dose of about 150 mg/kg.

23. The method of claim 13, wherein the therapeutically effective amount of the compound is administered to the subject at a daily dose of about 50 mg/kg.

24. The method of claim 13, wherein the compound is administered to the subject in a formulation comprising 0.5% (w/v) of methylcellulose and 0.1% of tween-20.

25. The method of claim 13, wherein the subject has breast cancer.

* * * * *